United States Patent [19]

Bauer et al.

[11] Patent Number: 5,639,871

[45] Date of Patent: *Jun. 17, 1997

[54] DETECTION OF HUMAN PAPILLOMAVIRUS BY THE POLYMERASE CHAIN REACTION

[75] Inventors: Heidi M. Bauer, San Francisco; Patti E. Gravitt; Catherine E. Greer, both of Oakland; Chaka C. Impraim, Danville, all of Calif.; M. Michele Manos, Baltimore, Md.; Robert M. Resnick, Oakland; Tracy Yi Zhang, Albany, both of Calif.

[73] Assignee: Roche Molecular Systems, Inc., Branchburg, N.J.

[*] Notice: The term of this patent shall not extend beyond the expiration date of Pat. No. 5,527,898.

[21] Appl. No.: 457,648

[22] Filed: Jun. 1, 1995

Related U.S. Application Data

[63] Continuation of Ser. No. 126,452, Sep. 24, 1993, abandoned, which is a continuation-in-part of Ser. No. 50,743, Apr. 20, 1993, Pat. No. 5,447,839, which is a continuation of Ser. No. 613,142, filed as PCT/US89/03747, Sep. 9, 1989, abandoned, which is a continuation-in-part of Ser. No. 322,550, Mar. 10, 1989, Pat. No. 5,182,377, which is a continuation-in-part of Ser. No. 243,486, Sep. 9, 1988, abandoned.

[51] Int. Cl.$^6$ .......................... C07H 21/02; C07H 21/04; C12P 19/34; C12Q 1/70

[52] U.S. Cl. .................. 536/24.31; 435/5; 435/6; 435/91.2; 536/22.1; 536/23.1; 536/24.3; 536/24.32; 536/24.33; 536/24.5

[58] Field of Search ........................ 435/5, 6, 912; 536/22.1, 23.1, 24.3, 24.31, 24.32, 24.33, 24.5

[56] References Cited

U.S. PATENT DOCUMENTS

| | | | |
|---|---|---|---|
| 4,849,332 | 7/1989 | Lorincz | 435/5 |
| 4,908,306 | 3/1990 | Lorincz | 435/5 |
| 5,057,411 | 10/1991 | Lancaster et al. | 435/6 |
| 5,187,090 | 2/1993 | de Villiers et al. | 435/235 |
| 5,283,171 | 2/1994 | Manos et al. | 435/5 |
| 5,527,898 | 6/1996 | Bauer et al. | 536/24.3 |

FOREIGN PATENT DOCUMENTS

| | | |
|---|---|---|
| 9211369 | 7/1992 | WIPO. |
| 9300435 | 1/1993 | WIPO. |

OTHER PUBLICATIONS

Seedorf et al., 1985, "Human Papillomavirus Type 16 DNA Sequence" Virology 145:181–185.

Cole and Streeck, 1986, "Genome Organization and Nucleotide Sequence of Human Papillomavirus Type 33, Which is Associated With Cervical Cancer" J. Virology 58(3):991–995.

Dartmann et al., 1986, "The Nucleotide Sequence and Genome Organization of Human Papilloma Virus Type 11" Virology 151:124–130.

Cole and Danos, 1987, "Nucleotide Sequence and Comparative Analysis of the Human Papillomavirus Type 18 Genome" J. Mol. Biol. 193:599–608.

Shibata et al., 1988, "Detection of Human Papilloma Virus in Paraffin–Embedded Tissue Using the Polymerase Chain Reaction" J. Exp. Med. 167:225–230.

Goldsborough et al., 1989, "Nucleotide Sequence of Human Papillomavirus Type 31: A Cervical Neoplasia–Associated Virus" Virology 171:306–311.

Resnick et al., 1990, "Detection and Typing of Human Papillomavirus in Archival Cervical Cancer Specimens by DNA Amplification With Consensus Primers" J. Natl. Cancer Institute 82(18):1477–1484.

Bauer et al., "Diagnostic Molecular Pathology a Practical Approach", vol. 2, Chapter 6, entitled Determination of Genital Human Papillomavirus Infection by Consensus PCR Amplification pp. 131–152, Ed. C.S. Herrington and J. O'McGee, 1992.

Ostrow et al., 1984, "Molecular Cloning and Characterization of a Unique Type of Human Papillomavirus from an Immune Deficient Patient" J. Invest. Dermatology 82:362–366.

Lorincz et al., 1987, "A New Type of Papillomavirus Associated With Cancer of the Uterine Cervix" Virology 159:187–190.

Hirsch–Behnam et al., 1990, "A Comparative Sequence Analysis of Two Human Papillomavirus (HPV) Types 2a and 57" Virus Research 18:81–98.

Kirii et al., 1991, "Human Papillomavirus Type 58 DNA Sequence" Virology 185;424–427.

Lungu et al., Aug., 1991, "Biologic Properties and Nucleotide Sequence Analysis of Human Papillomavirus Type 51" J. Virology 65:4216–4225.

Reuter et al., Oct., 1991, "Characterization of a Novel Human Papillomavirus DNA in the Cervical Carcinoma Cell Line ME180" J. Virology 65:5564–5568.

(List continued on next page.)

Primary Examiner—George C. Elliott
Assistant Examiner—Jeffrey Fredman
Attorney, Agent, or Firm—George W. Johnston; Stacey R. Sias; Douglas A. Petry

[57] ABSTRACT

The presence of human papillomavirus (HPV) in a sample can be detected and the HPV typed by a method that involves the amplification of HPV DNA sequences by the polymerase chain reaction (PCR). The primers used in the method are consensus primers that can be used to amplify a particular region of the genome of any HPV. The presence of HPV in a sample is indicated by the formation of amplified DNA. The HPV nucleic acid is detected by consensus probes that may be short oligonucleotide probes or long generic probes. The HPV is typed by the use of type-specific DNA probes specific for the amplified region of DNA.

1 Claim, No Drawings

OTHER PUBLICATIONS

Volpers and Streeck, 1991, "Genome Organization and Nucleotide Sequence of Human Papillomavirus Type 39" Virology 181:419–423.

Marich et al., 1992, "The Phylogenetic Relationship and Compelete Nucleotide Sequence of Human Papillomavirus Type 35" 186:770–776.

Philipp et al., 1992, "Human Papillomavirus Type 42: New Sequences, Conserved Genome Organization" Virology 186:331–334.

de Villiers et al., Nov., 1989, "Heterogeneity of the Human Papillomavirus Group" J. Virology 63(11):4898–4903.

Delius et al., 1993, GenBank Accession X74472 of "Human Papillomavirus Type 26 Genomic DNA".

SEQUENCE LISTING ( 1 ) GENERAL INFORMATION:

( i i i ) NUMBER OF SEQUENCES: 298

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CCAAACAGTA AGAGC                                      15

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGCTGTAGAG GGCTTAGAC                                 19

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GGTTGAAGCT ACAAAATGGG CC                           22

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTAGCGCACC TGGACAGG                                  18

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CAGGTAGTGA CTCAC                                                                                               15

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CATTTGTTGG GGTAACCAAC                                                                                          20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TAGGTCTGCA GAAAACTTTT C                                                                                        21

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TGTTTGCTGG CATAATCAAT                                                                                          20

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

TAAGTCTAAA GAAAACTTTT C                                                                                        21

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CATATGCTGG GGTAATCAGG                                                                                          20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

CAGGTCTGCA GAAAAGCTGT                                                   20

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TATTTGTTGG GGCAATCAG                                                    19

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

CTAAATCTGC AGAAAACTTT T                                            21

( 2 ) INFORMATION FOR SEQ ID NO:14:

( i ) SEQUENCE CHARACTERISTICS:
        ( A ) LENGTH: 455 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GCMCAGGGWC ATAA Y AATGG TATATGTTGG CACAATCAAT TGTTTTAAC AGTTGTAGAT     60

ACTACTCGCA GCACCAATCT Y TCTGTGTGT GCTTCTACTA CTTCTCCTAT TCCTAATGAA     120

TACACACCTA CCAGTTTTAA AGAATATGCC AGACATGTGG RGGAATTTGA TTTGCAGTTT     180

ATA Y TTCAAC TGTGTAAAAT AACWTTAACT ACAGAGGTAA TGTCATACAT TCATAATATG     240

AATACCACTA TTTTGGAGGA TTGGAATTTT GGTRTTACAC CACCTCCTAC TGCTARTTTA     300

GTTGACACAT ACCGTTTTGT TCAATCTGCT GCTGTAACTT GTCAAAAGGA CACCGCACCG     360

CCAGTTAAAC AGGACCCTTA TGACAAACTA AAGTTTTGGA CTGTAAATCT TAAGGAAAGG     420

TTTTCTGCAG ATCTTGATCA GTWTCC Y YTK GGACG     455

( 2 ) INFORMATION FOR SEQ ID NO:15:

( i ) SEQUENCE CHARACTERISTICS:
        ( A ) LENGTH: 450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| GCMCAGGGWC | ATAA Y AATGG | TATATGTTGG | GGAAATCAGC | TATTTTTAAC | TGTGGTTGAT | 60
| ACTACCCGTA | GTACTAACAT | GACTTTGTG Y | GCCACTGCAA | CATCTGGTGA | TACATATACA | 120
| GCTGCTAATT | TTAAGGAATA | TTTAAGACAT | GCTGAAGAAT | ATGATGTGCA | ATTTATATTT | 180
| CAATTGTGTR | AAATAACATT | AACTGTTGAA | GTTATGTCAT | ATATACACAA | TATGAATCCT | 240
| AACATATTAG | AGGAGTGGAA | TGTTGGTGTT | GCACCACCAC | CTTCAGGAAC | TTTAGAAGAT | 300
| AGTTATAGGT | ATGTACAATC | AGAAGCTATT | CGCTGTCAGG | CTAAGGTAAC | AACGCCAGAA | 360
| AAAAGGATC | CTTATTCAGA | CTTTTCCTTT | TGGGAGGTAA | ATTTATCTGA | AAAGTTTCT | 420
| ACTGATTTAG | GATCAGTWTC | C Y Y TKGGACG | | | | 450

( 2 ) INFORMATION FOR SEQ ID NO:16:

( i ) SEQUENCE CHARACTERISTICS:
( A ) LENGTH: 450 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

| | | | | | |
|---|---|---|---|---|---|
| GCMCAGGGWC | ATAA Y AATGG | CATATGCTGG | GGTAATCAGG | TATTTGTTAC | TGTTGTGGAT | 60
| ACTACCAGAA | GCACCAACAT | GACTATTAAT | GCAGCTAAAA | GCACATTARC | TAAATATGAT | 120
| GCCCGTGAAA | TCAATCAATA | CCTTCGCCAT | GTGGAGGAAT | ATGAACTACA | GTTTGTGTTT | 180
| CAACTTTGTA | AAATAACCTT | AACTGCAGAR | GTTATGGCAT | ATTTGCATAA | TATGAATAAT | 240
| ACTTTATTRG | ACGATTGGAA | TATTGGCTTA | TCCCCACCAG | TTGCAACTAG | CTTAGAGGAT | 300
| AAATATAGGT | ATATTAAAAG | CACAGCTRTT | ACA Y GTCAGA | GGGAACAGCC | CCCTGCAGAA | 360
| AAGCAGGATC | CCCTGGCTAA | ATATAAGTTT | TGGGAAGTTA | ATTTACAGGA | CAGCTTTTCT | 420
| GCAGACCTGG | GATCAGTWTC | C Y Y TKGGACG | | | | 450

( 2 ) INFORMATION FOR SEQ ID NO:17:

( i ) SEQUENCE CHARACTERISTICS:
( A ) LENGTH: 458 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

| | | | | | |
|---|---|---|---|---|---|
| GCMCAGGGWC | ATAA Y AATGG | TATTTGTTGG | CATAATCART | TATTTTTAAC | TGTTGTAGAT | 60
| ACTACTAGAA | GCACTAATTT | TTCTGTATGT | GTAGGTACAC | AGGCTAGTAG | CTCTACTACA | 120
| ACGTATGCCA | ACTCTAATTT | TAAGGAATAT | TTAAGACATG | CAGAAGAGTT | TGATTTACAG | 180
| TTTGTT Y TTC | AGTTATGTAA | AATTAGTTTA | ACTACTGAGG | TAATGACATA | TATACATTCT | 240
| ATGAATTCTA | CTATATTGGA | AGAGTGGAAT | TTTGGTCTTA | CCCCACCACC | GTCAGGTACT | 300
| TTAGAGGAAA | CATATAGATA | TGTAACATCA | CAKGCTATTA | GTTGCCAACG | TCCTCAACCT | 360
| CCTAAAGAAA | CAGAGGACCC | ATATGCCAAG | CTATCCTTTT | GGGATGTAGA | TCTTAAGGAA | 420
| AAGTTTTCTG | CAGAATTAGA | TCAGTWTCC Y | Y TKGGACG | | | 458

( 2 ) INFORMATION FOR SEQ ID NO:18:

( i ) SEQUENCE CHARACTERISTICS:
    ( A ) LENGTH: 452 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

| | | | | | | |
|---|---|---|---|---|---|---|
| GCMCAGGGWC | ATAA Y AATGG | TATTTGTTGG | GGCAATCAGT | TATTTGTTAC | TGTGGTAGAT | 60 |
| ACCACACGTA | GTACCAATAT | GTCTGTGTGT | GCTGCAATTG | CAAACAGTGA | TACTACATTT | 120 |
| AAAAGTAGTA | ATTTTAAAGA | GTATTTAAGA | CATGGTGAGG | AATTTGATTT | ACRATTTATA | 180 |
| TTTCAGTTAT | GCAAAATAAC | ATTATCTGCA | GACATAATGA | CATATATTCA | CAGTATGAAT | 240 |
| CCTGCTATTT | TGGAAGATTG | GAATTTTGGA | TTGACCACAC | CTCCCTCAGG | TTCTTTAGAG | 300 |
| GATACCTATA | GGTTTGTAAC | CTCACAGGCC | ATTACATGTC | AAAAARCTGC | CCCCAAAAG | 360 |
| CCCAAGGAAG | ATCCATTTAA | AGATTATGTA | TTTGGGAGG | TTAATTTAAA | AGAAAAGTTT | 420 |
| TCTGCAGATT | TAGATCAGTW | TCC Y Y TKGGA | CG | | | 452 |

( 2 ) INFORMATION FOR SEQ ID NO:19:

( i ) SEQUENCE CHARACTERISTICS:
        ( A ) LENGTH: 412 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

| | | | | | | |
|---|---|---|---|---|---|---|
| TATATGCTGG | TTTAATCAAT | TGTTTGTCAC | GGTGGTGGAT | ACCACCCGCA | GCACCAATTT | 60 |
| TACTATTAGT | GCTGCTACCA | ACACCGAATC | AGAATATAAA | CCTACCAATT | TTAAGGAATA | 120 |
| CCTAAGACAT | GTGGAGGAAT | ATGATTTGCA | GTTTATATTC | CAGTTGTGTA | AGGTCCGTCT | 180 |
| GACTCCAGAG | GTCATGTCCT | ATTTACATAC | TATGAATGAC | TCCTTATTAG | ATGAGTGGAA | 240 |
| TTTTGGTGTT | GTGCCCCCTC | CCTCCACAAG | TTTAGATGAT | ACCTATAGGT | ACTTGCAGTC | 300 |
| TCGCGCCATT | ACTTGCCAAA | AGGGGGCCGC | CGCCGCCAAG | CCTAAGGAAG | ATCCTTATGC | 360 |
| TGGCATGTCC | TTTTGGGATG | TAGATTTAAA | GGACAAGTTT | CTACTGATT | TG | 412 |

( 2 ) INFORMATION FOR SEQ ID NO:20:

( i ) SEQUENCE CHARACTERISTICS:
        ( A ) LENGTH: 415 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

| | | | | | | |
|---|---|---|---|---|---|---|
| TATTTGTTGG | CATAATCAGT | TGTTTGTTAC | TGTAGTGGAC | ACTACCCGCA | GTACTAATTT | 60 |
| AACATTATGT | GCCTCTACAC | AAAATCCTGT | GCCAAATACA | TATGATCCTA | CTAAGTTTAA | 120 |
| GCACTATAGT | AGACATGTGG | AGGAATATGA | TTTACAGTTT | ATTTTCAGT | TGTGCACTAT | 180 |
| TACTTTAACT | GCAGAGGTTA | TGTCATATAT | CCATAGTATG | AATAGTAGTA | TATTGGAAAA | 240 |
| TTGGAATTTT | GGTGTACCTC | CACCACCTAC | TACAAGTTTA | GTGGATACAT | ATCGTTTTGT | 300 |
| GCAATCCGTT | GCTGTTACCT | GTCAAAAGGA | TACTACACCT | CCAGAAAAGC | AGGATCCATA | 360 |
| TGATAAATTA | AAGTTTTGGA | CTGTTGACCT | AAAGGAAAAA | TTTTCCTCCG | ATTTG | 415 |

( 2 ) INFORMATION FOR SEQ ID NO:21:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CTGTGGTAGA TACCACACGC AGTAC                  25

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

CAGTTGTAGA TACTACTCGC AGCAC                  25

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CTGTGGTTGA TACTACCCGT AGTAC                  25

( 2 ) INFORMATION FOR SEQ ID NO:24:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

CTGTTGTGGA TACTACCAGA AGCAC                  25

( 2 ) INFORMATION FOR SEQ ID NO:25:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CTGTTGTAGA TACTACTAGA AGCAC                  25

( 2 ) INFORMATION FOR SEQ ID NO:26:

( i ) SEQUENCE CHARACTERISTICS:

( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:26:

CTGTGGTAGA TACCACACGT AGTAC     25

( 2 ) INFORMATION FOR SEQ ID NO:27:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:27:

CTGTAGTGGA CACTACCCGC AGTAC     25

( 2 ) INFORMATION FOR SEQ ID NO:28:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:28:

CTGTGGTAGA TACCACWCGC AGTAC     25

( 2 ) INFORMATION FOR SEQ ID NO:29:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:29:

GCTGACAGGT AGTAGCAGAG TT     22

( 2 ) INFORMATION FOR SEQ ID NO:30:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:30:

GCCATAACAT CTGTTGTAAG TG     22

( 2 ) INFORMATION FOR SEQ ID NO:31:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:31:

GAGTGGATGC AGATGCTG                                                     18

( 2 ) INFORMATION FOR SEQ ID NO:32:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:32:

CTAATGGTAA GGTTAGTACT GCG                                               23

( 2 ) INFORMATION FOR SEQ ID NO:33:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:33:

CAGCATCTGC ATCCACTC                                                     18

( 2 ) INFORMATION FOR SEQ ID NO:34:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:34:

ACCCAGTGCA CCAAAACC                                                     18

( 2 ) INFORMATION FOR SEQ ID NO:35:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:35:

CCAAAACCTA AAGATGATCC AT                                                22

( 2 ) INFORMATION FOR SEQ ID NO:36:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:36:

CACCAGGCCC ATATAATAAC AG                                                22

( 2 ) INFORMATION FOR SEQ ID NO:37:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:37:

TGTCAGCGCG ATGCC                  15

( 2 ) INFORMATION FOR SEQ ID NO:38:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:38:

GCAACCACAC AGTCTATGTC               20

( 2 ) INFORMATION FOR SEQ ID NO:39:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:39:

GACTCTTTCC GCAACCACAC               20

( 2 ) INFORMATION FOR SEQ ID NO:40:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:40:

CAGCATCCAC GCAGGATAG                19

( 2 ) INFORMATION FOR SEQ ID NO:41:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:41:

GAATAATGCC CCTGCAAAG                19

( 2 ) INFORMATION FOR SEQ ID NO:42:

( i ) SEQUENCE CHARACTERISTICS:

( A ) LENGTH: 20 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:42:

CAAATACAGA TATGTGCAGT                                                    20

( 2 ) INFORMATION FOR SEQ ID NO:43:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:43:

GTGCTGCTAC AACTCAGTCT                                                    20

( 2 ) INFORMATION FOR SEQ ID NO:44:

( i ) SEQUENCE CHARACTERISTICS:
         ( A ) LENGTH: 19 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:44:

CCCTGAAAAG GCAAAGCAG                                                     19

( 2 ) INFORMATION FOR SEQ ID NO:45:

( i ) SEQUENCE CHARACTERISTICS:
         ( A ) LENGTH: 21 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:45:

GCTAACCTAC TGGAGGACTG G                                                  21

( 2 ) INFORMATION FOR SEQ ID NO:46:

( i ) SEQUENCE CHARACTERISTICS:
         ( A ) LENGTH: 22 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:46:

GCACAGCTAT AACATGTCAA CG                                                 22

( 2 ) INFORMATION FOR SEQ ID NO:47:

( i ) SEQUENCE CHARACTERISTICS:
         ( A ) LENGTH: 22 base pairs
         ( B ) TYPE: nucleic acid
         ( C ) STRANDEDNESS: single
         ( D ) TOPOLOGY: linear (  i  i  ) MOLECULE TYPE: DNA (genomic)

(  x  i  ) SEQUENCE DESCRIPTION: SEQ ID NO:47:

CCTCCACATG TCTAAGGTAC TG                                                                     22

( 2 ) INFORMATION FOR SEQ ID NO:48:

(  i  ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear (  i  i  ) MOLECULE TYPE: DNA (genomic)

(  x  i  ) SEQUENCE DESCRIPTION:SEQ ID NO:48:

CAGTTAAGTA AATATGATGC ACG                                                                    23

( 2 ) INFORMATION FOR SEQ ID NO:49:

(  i  ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear (  i  i  ) MOLECULE TYPE: DNA (genomic)

(  x  i  ) SEQUENCE DESCRIPTION: SEQ ID NO:49:

ACACCSCACC GCCAGTT                                                                           17

( 2 ) INFORMATION FOR SEQ ID NO:50:

(  i  ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear (  i  i  ) MOLECULE TYPE: DNA (genomic)

(  x  i  ) SEQUENCE DESCRIPTION: SEQ ID NO:50:

TTAAACAGGA CCCTTATGAC A                                                                      21

( 2 ) INFORMATION FOR SEQ ID NO:51:

(  i  ) SEQUENCE CHARACTERISTICS:
            ( A ) LENGTH: 23 base pairs
            ( B ) TYPE: nucleic acid
            ( C ) STRANDEDNESS: single
            ( D ) TOPOLOGY: linear (  i  i  ) MOLECULE TYPE: DNA (genomic)

(  x  i  ) SEQUENCE DESCRIPTION: SEQ ID NO:51:

CCTAATGWAT ACACACCTAC CAG                                                                    23

( 2 ) INFORMATION FOR SEQ ID NO:52:

(  i  ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear (  i  i  ) MOLECULE TYPE: DNA (genomic)

(  x  i  ) SEQUENCE DESCRIPTION: SEQ ID NO:52:

CCCAAGGTAC GGAGGATCC                                                                         19

( 2 ) INFORMATION FOR SEQ ID NO:53:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

```
GATGGCTTAA ACTTTTGGAA TG                                          22
```

( 2 ) INFORMATION FOR SEQ ID NO:54:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

```
CAATCAGCAG CAATTACATG                                             20
```

( 2 ) INFORMATION FOR SEQ ID NO:55:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

```
CATGTAATTG CTGCTGATTG                                             20
```

( 2 ) INFORMATION FOR SEQ ID NO:56:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

```
TCCCCACCAG TTGCAACTAG                                             20
```

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

```
CATGTCAGAG GGAACAGCC                                              19
```

( 2 ) INFORMATION FOR SEQ ID NO:58:

( i ) SEQUENCE CHARACTERISTICS:

( A ) LENGTH: 19 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:58:

GTTGTGCCCC CTCCCTCCA 19

( 2 ) INFORMATION FOR SEQ ID NO:59:

( i ) SEQUENCE CHARACTERISTICS:
         ( A ) LENGTH: 25 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:59:

GACATTATGC ACTGAAGTAA CTAAG 25

( 2 ) INFORMATION FOR SEQ ID NO:60:

( i ) SEQUENCE CHARACTERISTICS:
         ( A ) LENGTH: 21 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:60:

GGCTAATGAA TACACAGCCT C 21

( 2 ) INFORMATION FOR SEQ ID NO:61:

( i ) SEQUENCE CHARACTERISTICS:
         ( A ) LENGTH: 19 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:61:

TCCTTCCACC AGCCTTGAT 19

( 2 ) INFORMATION FOR SEQ ID NO:62:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: DNA (genomic)

( x i ) SEQUENCE DESCRIPTION: SEQ ID NO:62:

CGCTATCTGC AGTCCCGTGC 20

( 2 ) INFORMATION FOR SEQ ID NO:63:

( i ) SEQUENCE CHARACTERISTICS:
         ( A ) LENGTH: 21 base pairs
         ( B ) TYPE: nucleic acid
         ( C ) STRANDEDNESS: single
         ( D ) TOPOLOGY: linear (i i) MOLECULE TYPE: DNA (genomic)

(x i) SEQUENCE DESCRIPTION: SEQ ID NO:63:

CTGCAGTCCC GTGCTATTAC C  21

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:64:

CTCAATCTGT TGCACAAACA  20

(2) INFORMATION FOR SEQ ID NO:65:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:65:

TAACCTTGCC CCCCTCAG  18

(2) INFORMATION FOR SEQ ID NO:66:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:66:

CATACCGCTA TCTGCAATCA G  21

(2) INFORMATION FOR SEQ ID NO:67:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:67:

CTACTACTGA ATCAGCTGTA CC  22

(2) INFORMATION FOR SEQ ID NO:68:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:68:

TTCTAMTGTW GTTSCATA YA CASHATA  27

( 2 ) INFORMATION FOR SEQ ID NO:69:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:69:

CCAATGTGTC TCCATACACA GAGTC               25

( 2 ) INFORMATION FOR SEQ ID NO:70:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:70:

CTAMTGTWGT TSCATA Y ACA SHATA             25

( 2 ) INFORMATION FOR SEQ ID NO:71:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:71:

AATGTGTCTC CATACACAGA GTC               23

( 2 ) INFORMATION FOR SEQ ID NO:72:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:72:

TAMTGTWGTT SCATA Y ACAS HATA             24

( 2 ) INFORMATION FOR SEQ ID NO:73:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:73:

ATGTGTCTCC ATACACAGAG TC               22

( 2 ) INFORMATION FOR SEQ ID NO:74:

( i ) SEQUENCE CHARACTERISTICS:

(A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:74:

CGAAGTGGAC GGACAAGAT											19

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:75:

CAAGGTGGAC AAACAAGACG											20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:76:

GAACACGTAG AGAAACCCAG											20

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:77:

CAACCGAGCA CGACAGGA											18

(2) INFORMATION FOR SEQ ID NO:78:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:78:

GAGGTCCCGA CGTAGAGAA											19

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear ( i i ) MOLECULE TYPE: DNA (genomic)

( x i ) SEQUENCE DESCRIPTION: SEQ ID NO:79:

AAATCCTGCA GAAAGACCTC 20

( 2 ) INFORMATION FOR SEQ ID NO:80:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

CCTACAGACG CCATGTTCA 19

( 2 ) INFORMATION FOR SEQ ID NO:81:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

CCTTGCAGGA CATTACAATA G 21

( 2 ) INFORMATION FOR SEQ ID NO:82:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:82:

CAGACGACCA CTACAGCAA 19

( 2 ) INFORMATION FOR SEQ ID NO:83:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:83:

GGTGCAAAAA GCACTTAACA G 21

( 2 ) INFORMATION FOR SEQ ID NO:84:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:84:

ACAGTATTGG AACTTACAG 19

( 2 ) INFORMATION FOR SEQ ID NO:85:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:85:

CAACAGTTAC TGCGACG　　　　　　　　　　　　　　　　　　　　　　　17

( 2 ) INFORMATION FOR SEQ ID NO:86:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:86:

GCAGTAAGGT ACTGCAC　　　　　　　　　　　　　　　　　　　　　　　17

( 2 ) INFORMATION FOR SEQ ID NO:87:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:87:

GACAGTATTG GAACTTACAG　　　　　　　　　　　　　　　　　　　　　20

( 2 ) INFORMATION FOR SEQ ID NO:88:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:88:

ACACCTAAAG GTCCTGTTTC　　　　　　　　　　　　　　　　　　　　　20

( 2 ) INFORMATION FOR SEQ ID NO:89:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:89:

ACACTCTGCA AATTCAGTGC　　　　　　　　　　　　　　　　　　　　　20

( 2 ) INFORMATION FOR SEQ ID NO:90:

( i ) SEQUENCE CHARACTERISTICS:

( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:90:

GTACTGCACG ACTATGT 17

( 2 ) INFORMATION FOR SEQ ID NO:91:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:91:

ACAAGACGTA TCTATTG 17

( 2 ) INFORMATION FOR SEQ ID NO:92:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:92:

GCAAGACATA GAAATAA 17

( 2 ) INFORMATION FOR SEQ ID NO:93:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:93:

ACCTTTGCAA CGATCTG 17

( 2 ) INFORMATION FOR SEQ ID NO:94:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:94:

CGACCCAATG CAAATTGGTC 20

( 2 ) INFORMATION FOR SEQ ID NO:95:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear

5,639,871

97

-continued ( i i ) MOLECULE TYPE: DNA (genomic)

( x i ) SEQUENCE DESCRIPTION: SEQ ID NO:95:

GCGACCCAAT GCAAATTGGT                                        20

( 2 ) INFORMATION FOR SEQ ID NO:96:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:96:

TGCGACCCAA TGCAAATTGG                                        20

( 2 ) INFORMATION FOR SEQ ID NO:97:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:97:

CTTGCGACCC AATGCAAATT                                        20

( 2 ) INFORMATION FOR SEQ ID NO:98:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:98:

GACCCAATGC AAATTGGTCT                                        20

( 2 ) INFORMATION FOR SEQ ID NO:99:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:99:

CATTTGCTGG AACAATCAG                                         19

( 2 ) INFORMATION FOR SEQ ID NO:100:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:100:

TAAATCTAAA GAAAATCGTT CCT                                    23

( 2 ) INFORMATION FOR SEQ ID NO:101:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:101:

GAAGAGCCAA GGACAGGTAC                                                              20

( 2 ) INFORMATION FOR SEQ ID NO:102:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:102:

CAACTTCATC CACGTTCACC                                                               20

( 2 ) INFORMATION FOR SEQ ID NO:103:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:103:

ACACAACTGT GTTCACTAGC                                                             20

( 2 ) INFORMATION FOR SEQ ID NO:104:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:104:

GAAGAGCCAA GGACAGGTAC                                                             20

( 2 ) INFORMATION FOR SEQ ID NO:105:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:105:

CAACTTCATC CACGTTCACC                                                             20

( 2 ) INFORMATION FOR SEQ ID NO:106:

( i ) SEQUENCE CHARACTERISTICS:

( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:106:

CTGTTGTTGA TACTACACGC AGTAC 25

( 2 ) INFORMATION FOR SEQ ID NO:107:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:107:

ATGGCKGA Y C CTGMAGGTAC 20

( 2 ) INFORMATION FOR SEQ ID NO:108:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:108:

ATGGCKGA Y G ATTCAGGTAC 20

( 2 ) INFORMATION FOR SEQ ID NO:109:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:109:

ATGGCKGA Y C CTTCAGGTAC 20

( 2 ) INFORMATION FOR SEQ ID NO:110:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:110:

TGTAMWGGMT GGTTTTATGT 20

( 2 ) INFORMATION FOR SEQ ID NO:111:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:111:

TGTAMWGGMT GGTTTGAGGT                                                                                           20

( 2 ) INFORMATION FOR SEQ ID NO:112:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:112:

TGTAMWGGMT GGTTTATGGT                                                                                           20

( 2 ) INFORMATION FOR SEQ ID NO:113:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:113:

GTACCTKCAG GRTCMGCCAT                                                                                           20

( 2 ) INFORMATION FOR SEQ ID NO:114:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:114:

GTACCTGAAT CRTCMGCCAT                                                                                           20

( 2 ) INFORMATION FOR SEQ ID NO:115:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:115:

GTACCTGAAG GRTCMGCCAT                                                                                           20

( 2 ) INFORMATION FOR SEQ ID NO:116:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:116:

ACATAAAACC AKCCWKTACA                                                                                           20

( 2 ) INFORMATION FOR SEQ ID NO:117:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:117:

ACCTCAAACC AKCCWKTACA                      20

( 2 ) INFORMATION FOR SEQ ID NO:118:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:118:

ACCATAAACC AKCCWKTACA                      20

( 2 ) INFORMATION FOR SEQ ID NO:119:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:119:

TCCACTTCAG WATTGCCATA                      20

( 2 ) INFORMATION FOR SEQ ID NO:120:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

TCCACTTCAG WA Y AGCCATA                    20

( 2 ) INFORMATION FOR SEQ ID NO:121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:121:

GAGCAATTAG WAGAC                           15

( 2 ) INFORMATION FOR SEQ ID NO:122:

( i ) SEQUENCE CHARACTERISTICS:

(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:122:

GAGCAATTAA RYGAC 15

(2) INFORMATION FOR SEQ ID NO:123:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:123:

CGGTTSAACC GAAAACGG 18

(2) INFORMATION FOR SEQ ID NO:124:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:124:

CGGTCGGGAC CGAAAACGG 19

(2) INFORMATION FOR SEQ ID NO:125:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:125:

CGGTTSAACC GAAAMCGG 18

(2) INFORMATION FOR SEQ ID NO:126:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:126:

CGGTTCAACC GAAAMCGG 18

(2) INFORMATION FOR SEQ ID NO:127:

(i) SEQUENCE CHARACTERISTICS:
(A) LENGTH: 17 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:127:

GCRCAGATGG GRCACAC    17

(2) INFORMATION FOR SEQ ID NO:128:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:128:

GCACACCACG GACACAC    17

(2) INFORMATION FOR SEQ ID NO:129:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:129:

CACACAAAGG ACAGGGTGTT C    21

(2) INFORMATION FOR SEQ ID NO:130:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:130:

WGCAWATGGA WWGC Y GTCTC    20

(2) INFORMATION FOR SEQ ID NO:131:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:131:

AGCATGCGGT ATACTGTCTC    20

(2) INFORMATION FOR SEQ ID NO:132:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:132:

TCCGTGTGGT GTGTCGTCCC    20

( 2 ) INFORMATION FOR SEQ ID NO:133:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:133:

WSCAWATGGW WWGYCGTCYC      20

( 2 ) INFORMATION FOR SEQ ID NO:134:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:134:

WGCAWATGGA WWGYYGTCYC      20

( 2 ) INFORMATION FOR SEQ ID NO:135:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:135:

WSCAWATGGW DWGYYGTCYC      20

( 2 ) INFORMATION FOR SEQ ID NO:136:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:136:

MGAGACRGCW WTCCATWTG      19

( 2 ) INFORMATION FOR SEQ ID NO:137:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:137:

MGAGACRGSW WTCCATWTG      19

( 2 ) INFORMATION FOR SEQ ID NO:138:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:138:

MGAGACRGVW WTCCATWTG                                                          19

( 2 ) INFORMATION FOR SEQ ID NO:139:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:139:

AGAGACAGTA TACCGCATG                                                          19

( 2 ) INFORMATION FOR SEQ ID NO:140:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:140:

GAGATWTATK CATATGC                                                            17

( 2 ) INFORMATION FOR SEQ ID NO:141:

( i ) SEQUENCE CHARACTERISTICS:
    ( A ) LENGTH: 1271 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:141:

```
GGATCCCCGG GCGAGCTCCA CTTCAGTATT GCCATACCCG CTGTCCGGAA CACTGTCCAC        60
TGCTCTCCTT TTAGCCTGTA AATTGTTTAC TTCGTCTGTG CTCTGCTGAC TGTTGCTTTG       120
ATTTGTTATG TCTTGCAACG GGCTGTTCTG ACTACCTAGT AACTTTCGTT TAATGCACG        180
CACTGCCTTC TTATTTGCTT GTGTTTCTTG TGCCTGAAAC AATGCCTGCG CTACCTGTTG       240
CTCTGCCCCA TCACTAATAT TACTATCATC TATAAATCCA ATTAGGTCTG ATCCTGTATC       300
GCTACTATAC TCTATTTCAT CTTCTAATAT TGTGTCTCCT GTATGTTTTT CTACTATTGC       360
TTCTACTGAA AACCACCCTG TACACCCCAA CCCCTCCCCA TCTGTACCTT CGCAGTCCAT       420
TGCAGGTTTA GTATGTAGCA CACTGGTGGC ACACCAAACT CACGTCGCCC ATCAGCAGCT       480
GCTCCACCGC TCGGACGTTC TGTCGACTGC TTAGTACAGC TAGCTGCACT ATACTATTAC       540
ATACACAACA TTCCGCTTCT ATTCTATAAC ACGCTTCTTG TTCAGCTTGT CTGGCTTGCT       600
GGTTACGCAC ATTATCTGTT TCATCCTCCT CTGAGCTGTC AAATTGTTCA TAGTCCWATT       660
GTTCGTAACA CTGTAGGTCA ATTTCGGGTT GCGGCACCAA ATCTAATATA ACATCCTGTA       720
```

| | | | | | | |
|---|---|---|---|---|---|---|
|TATTAATTGT|GTCTCCATGC|ATTGTTATTT|ATACTTGTGT|TTCTGTTGCT|TCGCGCCTTG|780|
|GTCTCCAGCA|GTTTGTGCAC|AACCCTTTCC|AGTACCCTGC|TATTTCATGG|AACCGTCGCT|840|
|TTTCATCCAC|AATTCTCTGT|TTTTCTTCCG|GTCCCAATGG|TATTTGGCAT|CTATGACACC|900|
|TTATTAACAA|ATTATACAAA|CTTCGTTTAG|TACGCGCTTC|CAGTGTTGCA|CCATACACAG|960|
|ACGATGTGTA|GCGTCTATAT|TCTATTATTT|TTGAATAGAA|TATTATACAT|TTTTTACATG|1020|
|CACCATATGC|ACTATCATTT|CTATACACTA|TTTTTAAATC|ACATATTGCA|AAGTTATATA|1080|
|CATCTGCCCA|TTCTAATGTT|TTCTTGCAAT|ATACACACTG|TACCTGCAAA|GATTGCAAAG|1140|
|GTGTATTCAA|AGCTTCACAT|AGTTCATGTA|TCGTTCGTGG|TCTTTCTCTG|GGATCTTGAA|1200|
|ACATAGCTGT|TTTTGTGTAT|GGCTGTGTCT|TTTACTTTA|TATGCACCGT|TTTCGGNTTC|1260|
|AACCGGAATT|C| | | | |1271|

(2) INFORMATION FOR SEQ ID NO:142:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:142:

| | | |
|---|---|---|
|CATCCGTAAC|TACATCTTCC A|21|

(2) INFORMATION FOR SEQ ID NO:143:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:143:

| | | |
|---|---|---|
|CTCCTGAAAA|GGAAAAGCCA|20|

(2) INFORMATION FOR SEQ ID NO:144:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:144:

| | | |
|---|---|---|
|TGGCTTTTCC|TTTTCAGGAG|20|

(2) INFORMATION FOR SEQ ID NO:145:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:145:

| | | | |
|---|---|---|---|
|ACAATGAATC|C Y TCTGTTTT|GG|22|

( 2 ) INFORMATION FOR SEQ ID NO:146:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:146:

ATCGCCTCCM CCAAATG         17

( 2 ) INFORMATION FOR SEQ ID NO:147:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:147:

TCTGTGTCTA AATCTGCTAC A         21

( 2 ) INFORMATION FOR SEQ ID NO:148:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:148:

CACACCTGAA AAAGAAAAAC AG         22

( 2 ) INFORMATION FOR SEQ ID NO:149:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:149:

CTGTTTTTCT TTTTCAGGTG TG         22

( 2 ) INFORMATION FOR SEQ ID NO:150:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:150:

CAGAAACCCA CACCTGAAAA AGA         23

( 2 ) INFORMATION FOR SEQ ID NO:151:

( i ) SEQUENCE CHARACTERISTICS:
        ( A ) LENGTH: 23 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:151:

AGAAACCCAC ACCTGAAAAA GAA                                        23

(2) INFORMATION FOR SEQ ID NO:152:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:152:

CATACACCTC CAGCACCTAA                                            20

(2) INFORMATION FOR SEQ ID NO:153:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:153:

TTGTAACCCA GGCAATTGCT                                            20

(2) INFORMATION FOR SEQ ID NO:154:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:154:

ACATACACCT CCAGCACCTA                                            20

(2) INFORMATION FOR SEQ ID NO:155:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:155:

CATACACCTC CAGCACCTA                                             19

(2) INFORMATION FOR SEQ ID NO:156:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

( x i ) SEQUENCE DESCRIPTION: SEQ ID NO:156:

GATATGGCAG CACATAATGA C                                                    21

( 2 ) INFORMATION FOR SEQ ID NO:157:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:157:

AGTTTCTGAA GTAGATATGG CA                                                   22

( 2 ) INFORMATION FOR SEQ ID NO:158:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:158:

CTGAAGTAGA TATGGCAGCA C                                                    21

( 2 ) INFORMATION FOR SEQ ID NO:159:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:159:

GTAACATCCC AGGCAATTG                                                       19

( 2 ) INFORMATION FOR SEQ ID NO:160:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:160:

TTTGTAACCC AGGCAATTGC T                                                    21

( 2 ) INFORMATION FOR SEQ ID NO:161:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:161:

GTTTGTAACC CAGGCAATTG CT                                                   22

( 2 ) INFORMATION FOR SEQ ID NO:162:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:162:

CAGTCTCCTG TACCTGGG                                    18

( 2 ) INFORMATION FOR SEQ ID NO:163:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:163:

GATGCTGCAC CGGCTGAA                                    18

( 2 ) INFORMATION FOR SEQ ID NO:164:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:164:

GCCCAGGTAC AGGAGAC                                     17

( 2 ) INFORMATION FOR SEQ ID NO:165:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:165:

GGGCAATATG ATGCTACCAA T                               21

( 2 ) INFORMATION FOR SEQ ID NO:166:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:166:

GTACCTGGGC AATATGATG                                  19

( 2 ) INFORMATION FOR SEQ ID NO:167:

( i ) SEQUENCE CHARACTERISTICS:
        ( A ) LENGTH: 18 base pairs ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:167:

TCTCCTGTAC CTGGGCAA                                                                          18

( 2 ) INFORMATION FOR SEQ ID NO:168:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:168:

GGATGCTGCA CCGGCTGA                                                                          18

( 2 ) INFORMATION FOR SEQ ID NO:169:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:169:

TCAGCCGGTG CAGCATCC                                                                          18

( 2 ) INFORMATION FOR SEQ ID NO:170:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:170:

CCAAAAGCCC AAGGAAGATC                                                                        20

( 2 ) INFORMATION FOR SEQ ID NO:171:

( i ) SEQUENCE CHARACTERISTICS:
                    ( A ) LENGTH: 19 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:171:

CAAAAGCCCA AGGAAGATC                                                                         19

( 2 ) INFORMATION FOR SEQ ID NO:172:

( i ) SEQUENCE CHARACTERISTICS:
                    ( A ) LENGTH: 22 base pairs
                    ( B ) TYPE: nucleic acid
                    ( C ) STRANDEDNESS: single
                    ( D ) TOPOLOGY: linear ( i i ) MOLECULE TYPE: DNA (genomic)

( x i ) SEQUENCE DESCRIPTION: SEQ ID NO:172:

TTGCAAACAG TGATACTACA TT 22

( 2 ) INFORMATION FOR SEQ ID NO:173:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:173:

GAGGGAGGTG TGGTCAAT 18

( 2 ) INFORMATION FOR SEQ ID NO:174:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:174:

AAGAACCTGA GGGAGGT 17

( 2 ) INFORMATION FOR SEQ ID NO:175:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:175:

CCAAAAGCC Y AAGGAAGATC 20

( 2 ) INFORMATION FOR SEQ ID NO:176:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:176:

ACCACACCTC CCTCAG 16

( 2 ) INFORMATION FOR SEQ ID NO:177:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:177:

ACAGGCCATT ACATGTCAA 19

( 2 ) INFORMATION FOR SEQ ID NO:178:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:178:

CACACAAGTA ACTAGTGACA G  21

( 2 ) INFORMATION FOR SEQ ID NO:179:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:179:

AAAAACAGTA CCTCCAAAGG A  21

( 2 ) INFORMATION FOR SEQ ID NO:180:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:180:

TCCTTTGGAG GTACTGTTTT T  21

( 2 ) INFORMATION FOR SEQ ID NO:181:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:181:

CTGCTGTGTC TTCTAGTGAC AG  22

( 2 ) INFORMATION FOR SEQ ID NO:182:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:182:

TGCACCAAAA CCTAAAGATG  20

( 2 ) INFORMATION FOR SEQ ID NO:183:

( i ) SEQUENCE CHARACTERISTICS:
    ( A ) LENGTH: 21 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:183:

ATCATCTTTA GGTTTTGGTG C 21

(2) INFORMATION FOR SEQ ID NO:184:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:184:

TAGAGTCTTC CATACCTTCT AC 22

(2) INFORMATION FOR SEQ ID NO:185:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:185:

CTGTAGCTCC TCCACCATCT 20

(2) INFORMATION FOR SEQ ID NO:186:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:186:

AGACACTTAC AGATACCTAC AG 22

(2) INFORMATION FOR SEQ ID NO:187:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:187:

CACACCAGGC CCATATAAT 19

(2) INFORMATION FOR SEQ ID NO:188:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:188:

CCAAGGTACG GGAGGATC 18

( 2 ) INFORMATION FOR SEQ ID NO:189:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:189:

GATCCTCCCG TACCTTG 17

( 2 ) INFORMATION FOR SEQ ID NO:190:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:190:

CACTGCAACA TCTGGTGAT 19

( 2 ) INFORMATION FOR SEQ ID NO:191:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:191:

TCACCAGATG TTGCAGTG 18

( 2 ) INFORMATION FOR SEQ ID NO:192:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:192:

GGCGTTGTTA CCTTAGCC 18

( 2 ) INFORMATION FOR SEQ ID NO:193:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:193:

GGCTAAGGTA ACAACGCC 18

( 2 ) INFORMATION FOR SEQ ID NO:194:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:194:

GGATACTACA CCTCCAG 17

( 2 ) INFORMATION FOR SEQ ID NO:195:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:195:

ATACTACACC TCCAGAAAAG C 21

( 2 ) INFORMATION FOR SEQ ID NO:196:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:196:

TAGTGGACAC TACCCGCAG 19

( 2 ) INFORMATION FOR SEQ ID NO:197:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:197:

GCACAGGATT TTGTGTAGAG G 21

( 2 ) INFORMATION FOR SEQ ID NO:198:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:198:

TGTATTTGGC ACAGGATTTT G 21

( 2 ) INFORMATION FOR SEQ ID NO:199:

( i ) SEQUENCE CHARACTERISTICS:
    ( A ) LENGTH: 20 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:199:

CAGGATTTTG TGTAGAGGCA 20

( 2 ) INFORMATION FOR SEQ ID NO:200:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:200:

CAAATCCTGT GCCAGGTAC 19

( 2 ) INFORMATION FOR SEQ ID NO:201:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:201:

GCACAGGATT TTGTGTAGAG 20

( 2 ) INFORMATION FOR SEQ ID NO:202:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:202:

TATTAGCACT GCCACTGCTG 20

( 2 ) INFORMATION FOR SEQ ID NO:203:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:203:

CCCAACATTT ACTCCAAGTA AC 22

( 2 ) INFORMATION FOR SEQ ID NO:204:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:204:

CTGAGGTTAG AAAGGAAAGC A 21

( 2 ) INFORMATION FOR SEQ ID NO:205:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:205:

CACTTCTACT GCTATAACTT GT 22

( 2 ) INFORMATION FOR SEQ ID NO:206:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:206:

ACACACCACC TAAAGGAAAG G 21

( 2 ) INFORMATION FOR SEQ ID NO:207:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:207:

CGCAACCACA CAGTCTATGT 20

( 2 ) INFORMATION FOR SEQ ID NO:208:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:208:

TTCTACCTTA CTGGAAGACT GG 22

( 2 ) INFORMATION FOR SEQ ID NO:209:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:209:

GGAGGTCAAT TTGCAAAAC 19

( 2 ) INFORMATION FOR SEQ ID NO:210:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:210:

TGCAGGGGCA TTATTCTTT                                                                 19

( 2 ) INFORMATION FOR SEQ ID NO:211:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:211:

TACAGCATCC ACGCAG                                                                    16

( 2 ) INFORMATION FOR SEQ ID NO:212:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:212:

CACGCAGGAT AGCTT                                                                     15

( 2 ) INFORMATION FOR SEQ ID NO:213:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:213:

CCACGCAGGA TAGCTT                                                                    16

( 2 ) INFORMATION FOR SEQ ID NO:214:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:214:

GTGCTGCTAC AACTCAGTCT                                                                20

( 2 ) INFORMATION FOR SEQ ID NO:215:

( i ) SEQUENCE CHARACTERISTICS:
    ( A ) LENGTH: 20 base pairs ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:215:

GCTACAACTC AGTCTCCATC                                                                   20

( 2 ) INFORMATION FOR SEQ ID NO:216:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:216:

TGCCTTTTCA GGGGGAG                                                                      17

( 2 ) INFORMATION FOR SEQ ID NO:217:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:217:

AATGTCTCTT TGTGTGCCAC                                                                   20

( 2 ) INFORMATION FOR SEQ ID NO:218:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:218:

GTGTGCCACT GTAACCACA                                                                    19

( 2 ) INFORMATION FOR SEQ ID NO:219:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:219:

GGATCAGTAG GGGTCTTAGG                                                                   20

( 2 ) INFORMATION FOR SEQ ID NO:220:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:220:

GCACTGAAGT AACTAAGGAA GG     22

( 2 ) INFORMATION FOR SEQ ID NO:221:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:221:

AGCACCCCCT AAAGAAAAGG A     21

( 2 ) INFORMATION FOR SEQ ID NO:222:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:222:

GCCAGTTAAA CAGGACCC     18

( 2 ) INFORMATION FOR SEQ ID NO:223:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:223:

CATAAGGGTC CTGTTTAACT G     21

( 2 ) INFORMATION FOR SEQ ID NO:224:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:224:

ATTAATGCAG CTAAAAGCAC ATT     23

( 2 ) INFORMATION FOR SEQ ID NO:225:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:225:

GATGCCCGTG AAATCAATCA A     21

( 2 ) INFORMATION FOR SEQ ID NO:226:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:226:

TACTTGCAGT CTCGCGCCA                 19

( 2 ) INFORMATION FOR SEQ ID NO:227:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:227:

CCAACACCGA ATCAGAATAT AAA             23

( 2 ) INFORMATION FOR SEQ ID NO:228:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:228:

GTAGGTACAC AGGCTAGTAG CTC             23

( 2 ) INFORMATION FOR SEQ ID NO:229:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:229:

GCTCTACTAC AACGTATGCC A               21

( 2 ) INFORMATION FOR SEQ ID NO:230:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:230:

AGTTGCCAAC GTCCTCAAC                 19

( 2 ) INFORMATION FOR SEQ ID NO:231:

( i ) SEQUENCE CHARACTERISTICS:
    ( A ) LENGTH: 43 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:231:

CATCCGTAAC TACATCTTCC AACAATGAAT CCYTCTGTTT TGG　　　　　　　　　　　　43

( 2 ) INFORMATION FOR SEQ ID NO:232:

( i ) SEQUENCE CHARACTERISTICS:
( A ) LENGTH: 41 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:232:

TCTGTGTCTA AATCTGCTAC ACCCAAGGTA CGGGAGGATC C　　　　　　　　　　　　41

( 2 ) INFORMATION FOR SEQ ID NO:233:

( i ) SEQUENCE CHARACTERISTICS:
( A ) LENGTH: 44 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:233:

GCTGACAGGT AGTAGCAGAG TTGCCATAAC ATCTGTTGTA AGTG　　　　　　　　　　　44

( 2 ) INFORMATION FOR SEQ ID NO:234:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:234:

GGCTAAGGTA ACAACGCCCA CTGCAACATC TGGTGAT　　　　　　　　　　　　　　37

( 2 ) INFORMATION FOR SEQ ID NO:235:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:235:

GATATGGCAG CACATAATGA CGTAACATCC CAGGCAATTG　　　　　　　　　　　　40

( 2 ) INFORMATION FOR SEQ ID NO:236:

( i ) SEQUENCE CHARACTERISTICS:
( A ) LENGTH: 39 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:236:

GGGCAATATG ATGCTACCAA TGGATGCTGC ACCGGCTGA    39

( 2 ) INFORMATION FOR SEQ ID NO:237:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:237:

CCAAAAGCC Y AAGGAAGATC TTGCAAACAG TGATACTACA TT    42

( 2 ) INFORMATION FOR SEQ ID NO:238:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:238:

CACACAAGTA ACTAGTGACA GTCCTTTGGA GGTACTGTTT TT    42

( 2 ) INFORMATION FOR SEQ ID NO:239:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:239:

CTGCTGTGTC TTCTAGTGAC AGATCATCTT TAGGTTTTGG TGC    43

( 2 ) INFORMATION FOR SEQ ID NO:240:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:240:

TAGAGTCTTC CATACCTTCT ACAGACACTT ACAGATACCT ACAG    44

( 2 ) INFORMATION FOR SEQ ID NO:241:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:241:

ATACTACACC TCCAGAAAAG CGCACAGGAT TTTGTGTAGA G    41

( 2 ) INFORMATION FOR SEQ ID NO:242:

( i ) SEQUENCE CHARACTERISTICS:
  ( A ) LENGTH: 43 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:242:

CACTTCTACT GCTATAACTT GTACACACCA CCTAAAGGAA AGG      43

( 2 ) INFORMATION FOR SEQ ID NO:243:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:243:

GTGCTGCTAC AACTCAGTCT CCCTGAAAAG GCAAAGCAG      39

( 2 ) INFORMATION FOR SEQ ID NO:244:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:244:

GCACAGCTAT AACATGTCAA CGCAGTTAAG TAAATATGAT GCACG      45

( 2 ) INFORMATION FOR SEQ ID NO:245:

( i ) SEQUENCE CHARACTERISTICS:
  ( A ) LENGTH: 46 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:245:

AGCACCCCCT AAAGAAAAGG AGACATTATG CACTGAAGTA ACTAAG      46

( 2 ) INFORMATION FOR SEQ ID NO:246:

( i ) SEQUENCE CHARACTERISTICS:
  ( A ) LENGTH: 41 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:246:

GCCAGTTAAA CAGGACCCCC TAATGWATAC ACACCTACCA G      41

( 2 ) INFORMATION FOR SEQ ID NO:247:

( i ) SEQUENCE CHARACTERISTICS:
  ( A ) LENGTH: 41 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:247:

TTCTACCTTA CTGGAAGACT GGCAGCATCC ACGCAGGATA G  41

(2) INFORMATION FOR SEQ ID NO:248:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:248:

GCAACCACAC AGTCTATGTC GAATAATGCC CCTGCAAAG  39

(2) INFORMATION FOR SEQ ID NO:249:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:249:

CCCAACATTT ACTCCAAGTA ACCATACCGC TATCTGCAAT CAG  43

(2) INFORMATION FOR SEQ ID NO:250:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:250:

CTACTACTGA ATCAGCTGTA CCTATTAGCA CTGCCACTGC TG  42

(2) INFORMATION FOR SEQ ID NO:251:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:251:

TTTTGGGAKG TKRAYTTAMA RGAAAAGTTT TC  32

(2) INFORMATION FOR SEQ ID NO:252:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:252:

TTTTGGRAKG TKRAYTTAAA RGAAARRTTT TC     32

( 2 ) INFORMATION FOR SEQ ID NO:253:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:253:

GAGGARTWTG ATTTRCARTT TATWTTTCA     29

( 2 ) INFORMATION FOR SEQ ID NO:254:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:254:

GARGARTWTG ATTTRCAGTT TATWTTTCAR     30

( 2 ) INFORMATION FOR SEQ ID NO:255:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:255:

ATTTGTTGGY RYAATCARYT RTTTGTTAC     29

( 2 ) INFORMATION FOR SEQ ID NO:256:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:256:

ATWTGYTGGG GYAATCARTT RTTGTTAC     29

( 2 ) INFORMATION FOR SEQ ID NO:257:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:257:

TTTTGGGAKG TWAATTTAMW AGAAARRTTT TC     32

( 2 ) INFORMATION FOR SEQ ID NO:258:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:258:

TTTTGGRAKG TKRAYTTAAA GGAAARGTTT TC      32

( 2 ) INFORMATION FOR SEQ ID NO:259:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:259:

GAAGARTWTG ATTTRCAATT TATWTTTCAR TTRTGT      36

( 2 ) INFORMATION FOR SEQ ID NO:260:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:260:

GARGARTWTG ATTTACARTT TATWTTTCAR      30

( 2 ) INFORMATION FOR SEQ ID NO:261:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:261:

ATWTGTTKGG GMAATCAMYT RTTTGTTAC      29

( 2 ) INFORMATION FOR SEQ ID NO:262:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:262:

ATTTGYTGGS RYAATCARTT RTTTGTTAC      29

( 2 ) INFORMATION FOR SEQ ID NO:263:

( i ) SEQUENCE CHARACTERISTICS:

(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:263:

GATCAGTWTC CYYTKGGACG 20

(2) INFORMATION FOR SEQ ID NO:264:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:264:

GATCAGTTTC CYYTKGGACG 20

(2) INFORMATION FOR SEQ ID NO:265:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:265:

CCGTTTTCGG TTSAACCG 18

(2) INFORMATION FOR SEQ ID NO:266:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:266:

CCGTTTTCGG TCCCGACCG 19

(2) INFORMATION FOR SEQ ID NO:267:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:267:

GCMCAGGGWC ATAAYAATGG 20

(2) INFORMATION FOR SEQ ID NO:268:

(i) SEQUENCE CHARACTERISTICS:
(A) LENGTH: 20 base pairs
(B) TYPE: nucleic acid
(C) STRANDEDNESS: single
(D) TOPOLOGY: linear (  i i  ) MOLECULE TYPE: DNA (genomic)

(  x i  ) SEQUENCE DESCRIPTION: SEQ ID NO:268:

GCMCAGGGDC  A Y AA Y AATGG                                                                 20

( 2 ) INFORMATION FOR SEQ ID NO:269:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:269:

CGTCCMARRG  GAWACTGATC                                                                      20

( 2 ) INFORMATION FOR SEQ ID NO:270:

(  i  ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:270:

CGTCCMARRG  GAWA Y TGATC                                                                    20

( 2 ) INFORMATION FOR SEQ ID NO:271:

(  i  ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:271:

CTGTGGTAGA  TACCACTCGC  AGTAC                                                               25

( 2 ) INFORMATION FOR SEQ ID NO:272:

(  i  ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:272:

GAGGTATWTG  AHTTTGC                                                                         17

( 2 ) INFORMATION FOR SEQ ID NO:273:

(  i  ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear (  i i  ) MOLECULE TYPE: DNA (genomic)

(  x i  ) SEQUENCE DESCRIPTION: SEQ ID NO:273:

| GAGCTCGCAC | AGGGTCATAA | CAATGGTATC | TGTTGGGGCA | ATCAATTGTT | TGTTACCTGT | 60 |
| GTTGATACCA | CCCGCAGTAC | TAACCTTACC | ATTAGTACAT | TATCTGCAGC | ATCTGCATCC | 120 |
| ACTCCATTTA | AACCATCTGA | TTATAAACAA | TTTATAAGAC | ATGGCGAAGA | ATATGAATTA | 180 |
| CAATTTATAT | TTCAGTTGTG | TAAAATAACA | CTTACAACAG | ATGTTATGGC | TTACATACAT | 240 |
| TTAATGAATG | CCTCCATATT | GGAGGATTGG | AATTTTGGAC | TAACCTTACC | TCCCACTGCT | 300 |
| AGTTGGAAG  | ATGCCTATAG | GTTATTAAA  | AACTCTGCTA | CTACCTGTCA | GCGTAACGCC | 360 |
| CCTCCTGTGC | CAAAGGAAGA | TCCTTTTCAA | AAATTTAAAT | TTGGGATGT  | AGATTTAAAA | 420 |
| GAAAAATTTT | CTATTGATTT | GGATCAGTTT | CCCCTGGGAC | GAAGCTT    |            | 467 |

( 2 ) INFORMATION FOR SEQ ID NO:274:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:274:

| GAGCTCGCCC | AGGGTCATAA | TAATGGCATC | TGTTGGAACA | ATCAGTTATT | TGTAACTGTT | 60 |
| GTGGATACCA | CCAGGAATAC | AAACATGACA | CTTTCTGCAA | CCACACAGTC | TATGTCCACA | 120 |
| TATAATTCAA | AGCAAATTAA | ACAGTATGTT | AGACATGCAG | AGGAATATGA | ATTACAATTT | 180 |
| GTGTTTCAAC | TATGTAAAAT | ATCCCTGTCT | GCTGAGGTTA | TGGCCTATTT | ACATACTATG | 240 |
| AATTCTACCT | TACTGGAAGA | CTGGAATATA | GGTTTGTCGC | CTCCTGTTGC | CACTAGCTTA | 300 |
| GAGGACAAAT | ACAGATATGT | AAAAGTGCA  | GCTATAACCT | GTCAAAAGGA | TCAGCCCCCT | 360 |
| CCTGAAAAGC | AGGACCCACT | ATCTAAATAT | AAATTTGGG  | AGGTCAATTT | ACAAAACAGT | 420 |
| TTTTCTGCTG | ATTTGGATCA | GTATCCCCTG | GGACGAAGCT | T          |            | 461 |

( 2 ) INFORMATION FOR SEQ ID NO:275:

( i ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:275:

| GAGCTCGCCC | AGGCTCATAA | TAATGGTATT | TGTTGGTTTA | ATGAATTGTT | TGTAACCGTT | 60 |
| GTGGATACCA | CCCGCAGTAC | TAATGTAACC | ATTTGTACTG | CTACATCCCC | CCCTGTATCT | 120 |
| GAATATAAAG | CCACGAGCTT | TAGGGAATAT | TTGCGCCATA | CAGAAGAGTT | TGATTTGCAA | 180 |
| TTCATTTTTC | AGTTATGTAA | AATACATTTA | ACCCCTGAAA | TTATGGCCTA | CCTACATAAT | 240 |
| ATGAATAAAG | CCTTGTTGGA | TGACTGGAAC | CTTGGTGTGG | TACCTCCACC | CTCTACCAGT | 300 |
| CTAGAAGACA | CATATAGGTT | TTTGCAGTCC | AGAGCTATTA | CATGTCAGAA | GGGTGCTGCT | 360 |
| GCCCCGCCGC | CCAAGGAGGA | TCGCTATGCC | AAATTATCAT | TTGGACTGT  | TGATTTACGA | 420 |
| GACAAGTTCT | CCACTGATTT | GGATCAGTAT | CCCTTGGGAC | GAAGCTT    |            | 467 |

( 2 ) INFORMATION FOR SEQ ID NO:276:

( i ) SEQUENCE CHARACTERISTICS:
        ( A ) LENGTH: 467 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:276:

| | | | | | | |
|---|---|---|---|---|---|---|
| GAGCTCGCAC | AGGGACATAA | CAATGGCATT | TGTTGGGGCA | ACCAATTGTT | TGTTACTTGT | 60 |
| GTAGATACTA | CCCGCAGTAC | CAACCTCACT | ATTAGTACTG | TATCTGCACA | ATCTGCATCT | 120 |
| GCCACTTTTA | AACCATCAGA | TTATAAGCAG | TTTATAAGGC | ATGGTGAGGA | ATATGAATTA | 180 |
| CAGTTTATAT | TTCAATTGTG | TAAAATTACT | CTTACCACTG | ATGTAATGGC | CTATATCCAT | 240 |
| ACAATGAATT | CTGCTATTTT | GGAAAATTGG | AATTTGGCC | TTACCTTGCC | TCCTACTGCT | 300 |
| AGTTTGGAAG | ATGCATATAG | GTTTATTAAA | AATTCAGCTA | CTACATGTCA | ACGCGATGCC | 360 |
| CCTGCACAGC | CCAAGGAGGA | TCCATTTAGT | AAATTAAAAT | TTTGGGACGT | TGATCTTAAA | 420 |
| GAAAAGTTTT | CTATTGATTT | AGATCAGTAT | CCCCTTGGAC | GAAGCTT | | 467 |

( 2 ) INFORMATION FOR SEQ ID NO:277:

( i ) SEQUENCE CHARACTERISTICS:
        ( A ) LENGTH: 460 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:277:

| | | | | | | |
|---|---|---|---|---|---|---|
| GAGCTCGCCC | AGGGTCATAA | TAATGGTCTT | TAAAAGTGAA | AGAGGGAGGC | AGAAGAAGGT | 60 |
| GTGATAGTAT | AGGGATGTAA | AGAAGACTCA | ACCAGCCCTT | GCTGGTTTTG | AAGCTGGAAG | 120 |
| AGGGTCGTGA | GCCAAGGAAT | AAGGGCAGCC | TCTAAAAAGC | TGGAAAAGAT | CAGAAAATGG | 180 |
| TTCTCACCTA | CAGTCTCCAG | AAAGGAACAC | CGTCTGGCCA | ACACCTTGAT | CTTAGCCCAG | 240 |
| TGAGACTCAT | TTCTACCTTC | TGACTTCCAG | AAGTTTAAGG | TAATCAACTT | TTGTTGTTTT | 300 |
| AAGCCACTGA | GTTAATGGCA | ATTTGTTACA | ACAGCCATAG | CAAGCTAGTA | TACCGAGTCT | 360 |
| CATTCTTACC | CTTATGAGAC | CTTCCACAAT | TTCATCCCAT | CCAACCCACC | CAGCAATGTC | 420 |
| TTCTGCTTGG | GTCAGATCAG | TATCCCTTTG | GACGAAGCTT | | | 460 |

( 2 ) INFORMATION FOR SEQ ID NO:278:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:278:

| | | | | | | |
|---|---|---|---|---|---|---|
| GAGCTCGCAC | AGGGACATAA | TAATGGTATA | TGCTGGGGTA | ATCAACTATT | TGTTACTGTT | 60 |
| GTAGACACTA | CACGTAGTAC | CAACATGACT | TTATGTTCTG | AGGAAAAATC | AGAGGCTACA | 120 |
| TACAAAAATG | AAAACTTTAA | GGAATACCTT | AGACATGTGG | AAGGATATGA | TTTGCAGTTT | 180 |
| ATATTTCAGC | TGTGCAAAAT | ATCCCTTACT | GCAAATGTTA | TGCAATACAT | ACACCATG | 240 |
| AATCCAGATA | TATTAGAGGA | CTGGCAATTT | GGCCTTACAC | CACCTCCTTC | AGGTAATTTA | 300 |
| CAGGACACAT | ATAGATTTGT | TACCTCGCAG | GCTATTACCT | GTCAAAAAAC | ATCCCCTCCA | 360 |
| ACAGCAAAGG | AAGATCCTCT | TAAAAAGTAC | AGTTTTTGGG | AAATCAATTT | AAAGGAAAAA | 420 |
| TTTTCTGCAG | ATTTAGATCA | GTATCCCCTT | GGACGAAGCT | T | | 461 |

( 2 ) INFORMATION FOR SEQ ID NO:279:

( i ) SEQUENCE CHARACTERISTICS:
        ( A ) LENGTH: 394 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:279:

```
ACACTACACG TAGTACTAAT TTACATTGTC TGCCTGCACC GAAACAGCCG TACCTGCTGT      60
ATATAGCCCT ACAAAGTTTA AGGAATATAC TAGGCATGTG GAGGAATATG ATTTACAATT     120
TATATTTCAA TTGTGTACTA TCACATTAAC TGCAGACGTT ATGGCCTACA TCCATACTAT     180
GAATCCTACA ATTTTGGACA ATTGGAATAT AGGCGTTACC CCTCCACCAT CTGCAAGCTG     240
AGCTTGGTGG ACACGTATAG GTATTTACAA TCAGCAGCAT AGCATGTCAG AAGGATGCTC     300
CTGCACCTGA AAAAAGGGT  CCCTATGACG ATTTAAAATT TTGGAATGTT GATTTAAAGG     360
AAAAGTTTAG TAACAGAACT AGATCAGTAT CCCC                                 394
```

( 2 ) INFORMATION FOR SEQ ID NO:280:

( i ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:280:

```
GAGCTCGCAC AGGGACATAA TAATGGCATT TCGTGGAATA ATCACGTTTT TATTACTTGT      60
GTTGACACTC ATAGAATGAC CAATTTAACC ATTACGACTC GTGTTACTCA ATCTGTTGCA     120
CAAACATTTA CTCCAGCAAA CTTTAAGCAA TACATTAGGC ATGGGGAAGA ATATGAATTG     180
CAATTTATAT TTCAATTGTG TAAAATCACT TTAACTACTG AAATTATGGC TTACCTGCAC     240
ACCATGGATT CTACAATTTT AGAACAGTGG AATTTTGGAT TAACCTTGCC CCCCTCAGCT     300
AGTTTGGAGG AGTCCTATGC ATTTGTAAAA AATGCAGCAA CATCCTGTCA CAAGGACAGT     360
CCTCCACAGG CTAAACAAGA CCCTTTGGCA AAATATAAAT TTTGGAATGT AGACCTTAAG     420
GAACGCTTTT CTTTGGATTT GGATCAGTTT CCTTTTGGAC GAAGCTT                   467
```

( 2 ) INFORMATION FOR SEQ ID NO:281:

( i ) SEQUENCE CHARACTERISTICS:
        ( A ) LENGTH: 462 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:281:

```
GAGCTCGCAC AGGGGTCATA ATAATGGCAT ATGCTGGGGT AATCAGGTAT TTGTTACTGT      60
TGTGGATACT ACCAGAAGCA CCAACATGAC TATTAATGCA GCTAAAAGCA CATTAACTAA     120
ATATGATGCC CGTGAAATCA ATCAATACCT TCGCCATGTG GAGGAATATG AACTACAGTT     180
TGTGTTTCAA CTTTGTAAAA TAACCTTAAC TGCAGAAGTT ATGGCATATT TGCATAATAT     240
GAATAATACT TTATTAGACG ATTGGAATAT TGGATTATCC CCACCAGTTG CAACTAGCTT     300
```

| | | | | | | |
|---|---|---|---|---|---|---|
| AGAGGATAAA | TATAGGTATA | TTAAAAGCAC | AGCTATTACA | TGTCAGAGGG | AACAGCCCCC | 360 |
| TGCAGAAAAG | CAGGATCCCC | TGGCTAAATA | TAAGTTTTGG | GAAGTTAATT | TACAGAACAG | 420 |
| CTTTTCTGCA | GACCTGGATC | AGTTCCTTT | TGGACGAAGC | TT | | 462 |

( 2 ) INFORMATION FOR SEQ ID NO:282:

( i ) SEQUENCE CHARACTERISTICS:
        ( A ) LENGTH: 464 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:282:

| | | | | | | |
|---|---|---|---|---|---|---|
| GAGCTCGCCC | AGGGACATAA | TAATGGCATT | TGTTGGTTTA | ATGAGTTATT | TGTTACAGTT | 60 |
| GTAGATACTA | CCCGCAGTAC | CAATATTACT | ATTTCAGCTG | CTGCTACACA | GGCTAATGAA | 120 |
| TACACAGCCT | CTAACTTTAA | GGAATACCTC | CGCCACACCG | AGGAATATGA | CTTACAGGTT | 180 |
| ATATTGCAAC | TTTGCAAAAT | ACATCTTACC | CCTGAAATTA | TGGCATACCT | ACATAGTATG | 240 |
| AATGAACATT | TATTGGATGA | GTGGAATTTT | GGCGTGTTAC | CACCTCCTTC | CACCAGCCTT | 300 |
| GATGATACCT | ATCGCTATCT | GCAGTCCCGT | GCTATTACCT | GCCAAAAGGG | TCCTTCGCC | 360 |
| CCTGCCCCTA | AAAGGATCC | TTATGATGGC | CTTGTATTTT | GGGAGGTTGA | TTTAAAGGAC | 420 |
| AAACTATCCA | CAGATTTGGA | TCAGTATCCT | TGGGACGAA | GCTT | | 464 |

( 2 ) INFORMATION FOR SEQ ID NO:283:

( i ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:283:

| | | | | | | |
|---|---|---|---|---|---|---|
| GAGCTCGCAC | AGGGTCATAA | TAATGGTATT | TGTTGGCATA | ATCAATTATT | TCTTACTGTT | 60 |
| GTGGATACCA | CTCGCAGTAC | CAATTTTACT | TTGTCTACTA | CTACTGAATC | AGCTGTACCA | 120 |
| AATATTTATG | ATCCTAATAA | ATTTAAGGAA | TATATTAGGC | ATGTTGAGGA | ATATGATTTG | 180 |
| CAATTTATAT | TTCAGTTGTG | TACTATAACA | TTGTCAACTG | ATGTAATGTC | CTATATACAT | 240 |
| ACTATGAATC | CTGCTATTTT | GGATGATTGG | AATTTGGTG | TTGCCCCTCC | ACCATCTGCT | 300 |
| AGTCTTGTAG | ATACATACCG | CTATCTGCAA | TCAGCAGCAA | TTACATGTCA | AAAAGACGCC | 360 |
| CCTGCACCTA | CTAAAAAGGA | TCCATATGAT | GGCTTAAACT | TTTGGAATGT | AAATTTAAAA | 420 |
| GAAAAGTTTA | GTTCTGAACT | GGATCAGTTT | CCCCTTGGAC | GAAGCTT | | 467 |

( 2 ) INFORMATION FOR SEQ ID NO:284:

( i ) SEQUENCE CHARACTERISTICS:
        ( A ) LENGTH: 464 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:284:

| | | | | | | |
|---|---|---|---|---|---|---|
| CAACGTGCAC | AAGGCCATAA | TAATGGTATT | TGTTGGAGTA | ACCAATTGTT | TGTTACTGTA | 60 |
| GTTGATACAA | CCCGTAGTAC | AAATATGTCT | GTGTGTTCTG | CTGTGTCTTC | TAGTGACAGT | 120 |

| | | | | | |
|---|---|---|---|---|---|
| ACATATAAAA | ATGACAATTT | TAAGGAATAT | TTAAGGCATG | GTGAAGAATA | TGATTTACAG | 180
| TTTATTTTTC | AGTTATGTAA | AATAACACTA | ACAGCAGATG | TTATGACATA | TATTCATAGT | 240
| ATGAACCCGT | CCATTTTAGA | GGATTGGAAT | TTTGGCCTTA | CACCACCGCC | TTCTGGTACC | 300
| TTAGAGGACA | CATATCGCTA | TGTAACATCA | CAGGCTGTAA | CTTGTCAAAA | ACCCAGTGCA | 360
| CCAAAACCTA | AAGATGATCC | ATTAAAAAAT | TATACTTTTT | GGGAGGTTGA | TTTAAAGGAA | 420
| AAGTTTCTG | CAGACTTAGA | TCAATTTCCG | TTGGGCCGTA | AATT | | 464

( 2 ) INFORMATION FOR SEQ ID NO:285:

( i ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:285:

| | | | | | |
|---|---|---|---|---|---|
| GAGCTCGCCC | AGGGTCATAA | TAATGGTATA | TGTTGGCATA | ATCAATTATT | CTTACTGTT | 60
| GTGGACACTA | CCCGTAGTAC | CAACTTTACA | TTATCTACCT | CTATAGAGTC | TTCCATACCT | 120
| TCTACATATG | ATCCTTCTAA | GTTAAGGAA | TATACCAGGC | ACGTGGAGGA | GTATGATTTA | 180
| CAATTTATAT | TTCAACTGTG | TACTGTCACA | TTAACAACTG | ATGTTATGTC | TTATATTCAC | 240
| ACTATGAATT | CCTCTATATT | GGACAATTGG | AATTTGCTG | TAGCTCCTCC | ACCATCTGCC | 300
| AGTTGGTAG | ACACTTACAG | ATACCTACAG | TCTGCAGCCA | TTACATGTCA | AAAGGATGCT | 360
| CCAGCACCTG | AAAAGAAAGA | TCCATATGAC | GGTCTAAAGT | TTTGGAATGT | TGACTTAAGG | 420
| GAAAAGTTTA | GTTTGGAACT | TGATCAGTAT | CCCTTGGGAC | GAAGCTT | | 467

( 2 ) INFORMATION FOR SEQ ID NO:286:

( i ) SEQUENCE CHARACTERISTICS:
        ( A ) LENGTH: 467 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:286:

| | | | | | |
|---|---|---|---|---|---|
| CAAAAGGCCC | AGGGCCATAA | CAATGGCATA | TGTTTTGGCA | ATCAGTTATT | TGTTACAGTT | 60
| GTAGACACCA | CTCGTAGCAC | TAATTTGACC | TTATGTGCTG | CCACACAGGG | CCCCACACCA | 120
| GGCCCATATA | ATAACAGTAA | TTTCAAGGAA | TATTTGCGTC | AGGGGAGGA | GTTTGATTTG | 180
| CAGTTTATTT | TTCAGTTATG | TGTAATTACC | TTAAATGCAG | AGGTTATGAC | ATATATTCAT | 240
| GCAATGGATC | CTACGTTGTT | GGAGGATTGG | AACTTTAAAA | TTGCTCCTCC | AGCCTCTGCA | 300
| TCCTTAGAGG | ATACATATAG | GTTCCTTACC | AACAAGGCTA | TTGCCTGTCA | GCGCGATGCC | 360
| GCCCCCAAGG | TACGGGAGGA | TCCATATAAA | AAATATAAAT | TTGGGATGT | CAATTTAACA | 420
| GAAAGATTTT | CTTCCCAATT | AGATCAATTT | CCATTAGGAC | GTAAGTT | | 467

( 2 ) INFORMATION FOR SEQ ID NO:287:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:287:

| GAGCTCGCAC | AGGGTCATAA | TAATGGTATA | TGTTGGGGAA | ATCAGCTATT | TTTAACTGTG | 60 |
| GTTGATACTA | CCCGTAGTAC | TAACATGACT | TTGTGTGCCA | CTGCAACATC | TGGTGATACA | 120 |
| TATACAGCTG | CTAATTTTAA | GGAATATTTA | AGACATGCTG | AAGAATATGA | TGTGCAATTT | 180 |
| ATATTTCAAT | TGTGTAAAAT | AACATTAACT | GTTGAAGTTA | TGTCATATAT | ACACAATATG | 240 |
| AATCCTAACA | TATTAGAGGA | GTGGAATGTT | GGTGTTGCAC | CACCACCTTC | AGGAACTTTA | 300 |
| GAAGATAGTT | ATAGGTATGT | ACAATCAGAA | GCTATTCGCT | GTCAGGCTAA | GGTAACAACG | 360 |
| CCAGAAAAAA | AGGATCCTTA | TTCAGACTTT | TCCTTTTGGG | AGGTAAATTT | ATCTGAAAAG | 420 |
| TTTTCTACTG | ATTAGATCA | GTATCCTCTG | GGACGAAGCT | T | | 461 |

( 2 ) INFORMATION FOR SEQ ID NO:288:

( i ) SEQUENCE CHARACTERISTICS:
( A ) LENGTH: 467 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:288:

| GAGCTCGCAC | AGGGTCATAA | CAATGGTATT | TGTTGGCATA | ATCAGTTGTT | TGTTGCTGTA | 60 |
| GTGGACACTA | CCCGCAGTAC | TAATTTAACA | TTATGTGCCT | CTACACAAAA | TCCTGTGCCA | 120 |
| AGTACATATG | ACCCTACTAA | GTTTAAGCAG | TATAGTAGAC | ATGTGGAGGA | ATATGATTTA | 180 |
| CAGTTTATTT | TTCAGTTGTG | CACTATTACT | TTAACTGCAG | AGGTTATGTC | ATATATCCAT | 240 |
| AGTATGAATA | GTAGTATATT | AGAAAATTGG | AATTTGGTG | TCCCTCCACC | ACCTACTACA | 300 |
| AGTTTGGTGG | ATACATATCG | TTTTGTGCAA | TCAGTTGCTG | TTACCTGTCA | AAAGGATACT | 360 |
| ACACCTCCAG | AAAAGCAGGA | TCCATATGAT | AAATTAAAGT | TTTGGACTGT | TGACCTAAAG | 420 |
| GAAAAATTTT | CCTCCGATTT | GAATCAGTAT | CCCTTGGGAC | GAAGCTT | | 467 |

( 2 ) INFORMATION FOR SEQ ID NO:289:

( i ) SEQUENCE CHARACTERISTICS:
( A ) LENGTH: 449 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:289:

| TCCACCGTGC | GCAGGGTCAC | AATAATGGCA | TTTGCTGGAA | CAATCAGCTT | TTTATTACCT | 60 |
| GTGTTGATAC | TACCAGAAGT | ACAAATTTAA | CTATTAGCAC | TGCCACTGCT | GCGGTTTCCC | 120 |
| CAACATTTAC | TCCAAGTAAC | TTTAAGCAAT | ATATTAGGCA | TGGGGAAGAG | TATGAATTGC | 180 |
| AATTTATTTT | TCAATTATGT | AAAATTACTT | TAACTACAGA | GGTAATGGCT | TATTTACACA | 240 |
| CAATGGATCC | TACCATTCTT | GAACAGTGGA | ATTTGGATT | AACATTACCT | CCGTCTGCTA | 300 |
| GTTGGAGGA | TGCATATAGG | TTTGTTAGAA | ATGCAGCTAC | TAGCTGTCAA | AAGGACACCC | 360 |
| CTCCACAGGC | TAAGCCAGAT | CCTTTGGCCA | AATATAAATT | TTGGGATGTT | GATTTAAAGG | 420 |
| AACGATTTTC | TTTAGATTTA | GACCAATTT | | | | 449 |

( 2 ) INFORMATION FOR SEQ ID NO:290:

( i ) SEQUENCE CHARACTERISTICS:
    ( A ) LENGTH: 461 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:290:

| | | | | | | |
|---|---|---|---|---|---|---|
| GAGCTCGCCC | AGGGTCATAA | TAATGGCATA | TGTTGGGGCA | ATCAGTTGTT | TGTCACAGTT | 60 |
| GTGGATACCA | CTCGTAGCAC | TAACATGACT | TTATGTGCTG | AGGTTAGAAA | GGAAAGCACA | 120 |
| TATAAAAATG | AAAATTTTAA | GGAATACCTT | CGTCATGGCG | AGGAATTTGA | TTTACAATTT | 180 |
| ATTTTTCAAT | TGTGCAAAAT | TACATTAACA | GCTGATGTTA | TGACATACAT | TCATAAGATG | 240 |
| GATGCCACTA | TTTTAGAGGA | CTGGCAATTT | GGCCTTACCC | CACCACCGTC | TGCATCTTTG | 300 |
| GAGGACACAT | ACAGATTTGT | CACTTCTACT | GCTATAACTT | GTCAAAAAAA | CACACCACCT | 360 |
| AAAGGAAAGG | AAGATCCTTT | AAAGGACTAT | ATGTTTGGG | AGGTGGATTT | AAAAGAAAAG | 420 |
| TTTTCTGCAG | ATTAAATCA | GTATCCTTTT | GGACGAAGCT | T | | 461 |

( 2 ) INFORMATION FOR SEQ ID NO:291:

( i ) SEQUENCE CHARACTERISTICS:
    ( A ) LENGTH: 461 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:291:

| | | | | | | |
|---|---|---|---|---|---|---|
| GAGCTCGCCC | AGGGTCATAA | TAATGGCATC | TGTTGGAACA | ATCAGTTATT | TGTAACTGTT | 60 |
| GTGGATACCA | CCAGGAATAC | AAACATGACT | CTTTCCGCAA | CCACACAGTC | TATGTCTACA | 120 |
| TATAATTCAA | AGCAAATTAA | ACAGTATGTT | AGACATGCAG | AGGAATATGA | ATTACAATTT | 180 |
| GTGTTTCAAC | TATGTAAAAT | ATCCCTGTCT | GCTGAGGTTA | TGGCCTATTT | ACATACTATG | 240 |
| AATTCTACCT | TACTGGAAGA | CTGGAATACA | GGTTTGTCGC | CTCCTGTTGC | CACTAGCTTA | 300 |
| GAGGACAAAT | ACAGATATGT | GAAAAGTGCA | GCTATAACCT | GTCAAAGGA | TCAGCCCCCT | 360 |
| CCTGAAAAGC | AGGACCCACT | ATCTAAATAT | AAATTTGGG | AGGTCAATTT | GCAAAACAGT | 420 |
| TTTTCTGCTG | ATTTGGATCA | GTATCCCCTG | GGACGAAGCT | T | | 461 |

( 2 ) INFORMATION FOR SEQ ID NO:292:

( i ) SEQUENCE CHARACTERISTICS:
    ( A ) LENGTH: 464 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:292:

| | | | | | | |
|---|---|---|---|---|---|---|
| GAGCTCGCAC | AGGGTCATAA | TAATGGTATT | TGTTGGGGCA | ATCAATTGTT | TTTAACAGTT | 60 |
| GTAGATACCA | CCCGTAGTAC | TAACCTAACA | TTGTGTGCTA | CAGCATCCAC | GCAGGATAGC | 120 |
| TTTAATAATT | CTGACTTTAG | GGAGTATATT | AGACATGTGG | AGGAATATGA | TTTACAGTTT | 180 |
| ACATTTCAGT | TATGTACCAT | AGCCCTTACA | GCAGATGTTA | TGGCCTATAT | TCATGGAATG | 240 |
| AATCCCACTA | TTCTAGAGGA | CTGGAACTTT | GGTATAACCC | CCCAGCTAC | AAGTAGTTTG | 300 |
| GAGGACACAT | ATAGGTTTGT | ACAGTCACAG | GCCATTGCAT | GTCAAAAGAA | TAATGCCCCT | 360 |

```
GCAAAGGAAA AGGAGGATCC TTACAGTAAA TTTACTTTTT GGACTGTTGA CCTTAAGGAA    420

CGATTTTCAT CTGACCTTGA TCAGTATCCC CTTGGACGAA GCTT                    464
```

( 2 ) INFORMATION FOR SEQ ID NO:293:

( i ) SEQUENCE CHARACTERISTICS:
        ( A ) LENGTH: 455 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:293:

```
GCGCAGGGCC ACAATAATGG TATTTGTTGG GGGAATCAGT TATTTGTTAC TGTTGTAGAT     60

ACTACACGTA GTACAAACAT GACAATATGT GCTGCTACAA CTCAGTCTCC ATCTACAACA    120

TATAATAGTA CAGAATATAA ACAATACATG CGACATGTTG AGGAGTTTGA CTTACAGTTT    180

ATGTTTCAAT TATGTAGTAT TACCTTAACT GCTGAGGTAA TGGCCTATTT ACATACCATG    240

AATCCTGGTA TTTTGGAACA GTGGAACTTT GGGTTGTCGC CACCCCAAA TGGTACCTTA     300

GAAGACAAAT ACAGATATGT GCAGTCACAG GCCATTACAT GTCAAAAGCC TCCCCCTGAA    360

AAGGCAAAGC AGGACCCCTA TGCAAAATTA AGTTTTGGG AGGTAGATCT CAGAGAAAAG     420

TTTTCTAGTG AGTTAGATCA ATATCCCCTT GGTAG                              455
```

( 2 ) INFORMATION FOR SEQ ID NO:294:

( i ) SEQUENCE CHARACTERISTICS:
        ( A ) LENGTH: 461 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:294:

```
GAGCTCGCAC AGGGACATAA TAATGGCATT TGCTGGGGTA ATCAATTATT TGTGACTGTA     60

GTAGATACTA CTAGAAGTAC TAACATGACT ATTAGTACTG CTACAGAACA GTTAAGTAAA    120

TATGATGCAC GAAAAATTAA TCAGTACCTT AGACATGTGG AGGAATATGA ATTACAATTT    180

GTTTTTCAAT TATGCAAAAT TACTTTGTCT GCAGAGGTTA TGGCATATTT ACATAATATG    240

AATGCTAACC TACTGGAGGA CTGGAATATT GGGTTATCCC CGCCAGTGGC CACCAGCCTA    300

GAAGATAAAT ATAGATATGT TAGAAGCACA GCTATAACAT GTCAACGGGA ACAGCCACCA    360

ACAGAAAAAC AGGACCCATT AGCTAAATAT AAATTTTGGG ATGTTAACTT ACAGGACAGT    420

TTTTCTACAG ACCTGGATCA GTATCCCTTG GGACGAAGCT T                       461
```

( 2 ) INFORMATION FOR SEQ ID NO:295:

( i ) SEQUENCE CHARACTERISTICS:
        ( A ) LENGTH: 449 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:295:

```
GCCCAGGGAC ATAACAATGG CATGTGCTGG GGCAATCGGA TCTTCCTAAC AGTGGTGGAC     60

ACCACGCGCA GCACAAATGT CTCTTTGTGT GCCACTGTAA CCACAGAAAC TAATTATAAA    120
```

```
GCCTCCAATT  ATAAGGAATA  CCTTAGGCAT  ATGGAGGAAT  ATGATTTGCA  GTTCATTTTT      180

CAACTGTGCA  AAATAACACT  CACCCCCGAG  ATAATGGCAT  ACATACATAA  CATGGATGCG      240

CGGTTGCTAG  AGGACTGGAA  CTTTGGTGTC  CCCCCACCCC  CGTCCGCCAG  CCTGCAGGAC      300

ACCTACAGGT  ATTTGCAATC  CCAAGCGATA  ACATGTCAGA  AGCCCACACC  CCCTAAGACC      360

CCTACTGATC  CCTATGCAAC  CATGACATTC  TGGGATGTGG  ATCTCAGTGA  AAGTTTTCC       420

ATGGATCTGG  ACCAATTCCC  CCTGGGACG                                          449
```

( 2 ) INFORMATION FOR SEQ ID NO:296:

( i ) SEQUENCE CHARACTERISTICS:
        ( A ) LENGTH: 464 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:296:

```
CACAAGGCTC  AGGGTTTAAA  CAATGGTATA  TGTTGGCACA  ATCAATTGTT  TTTAACAGTT      60

GTAGATACTA  CTCGCAGCAC  CAATCTTTCT  GTGTGTGCTC  TACTACTCTC  TATTCCTAAT      120

GTATACACAC  CTACCAGTTT  TAAAGAATAT  GCCAGACATG  TGGAGGAATT  TGATTTGCAG      180

TTTATATTTC  AACTGTGTAA  AATAACATTA  ACTACAGAGG  TAATGTCATA  CATTCATAAT      240

ATGAATACCA  CTATTTTGGA  GGATTGGAAT  TTTGGTGTTA  CACCACCTCC  TACTGCTAGT      300

TTAGTTGACA  CATACCGTTT  TGTTCAATCT  GCTGCTGTAA  CTTGTCAAAA  GGACACCGCA      360

CCGCCAGTTA  AACAGGACCC  TTATGACAAA  CTAAAGTTTT  GGCCTGTAGA  TCTTAAGGAA      420

AGGTTTCTG   CAGATCTTGA  TCAGTTTCCT  TTGGGACGTA  AATT                       464
```

( 2 ) INFORMATION FOR SEQ ID NO:297:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:297:

```
GAGGTATWTG  AHTTTGC                                                        17
```

( 2 ) INFORMATION FOR SEQ ID NO:298:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:298:

```
CACACAATD Y  Y Y AGTGT-
GCC  C                                                                     21
```

DETECTION OF HUMAN PAPILLOMAVIRUS BY THE POLYMERASE CHAIN REACTION

This application is a continuation of application Ser. No. 08/126,452, filed Sep. 24, 1993, now abandoned, which is a continuation-in-part of U.S. Ser. No. 08/050,743, filed Apr. 20, 1993, which issued as U.S. Pat. No. 5,447,839 which is a continuation of U.S. Ser. No. 07/613,142, filed Nov. 14, 1990, now abandoned, which is a continuation-in-part of PCT/US89/03747, filed Sep. 9, 1989, which is a continuation-in-part of U.S. Ser. No. 322,550, filed Mar. 10, 1989, which issued as U.S. Pat. No. 5,182,377, which is a continuation-in-part of U.S. Ser. No. 243,486, filed Sep. 9, 1988, now abandoned, each of which is incorporated herein by reference.

BACKGROUND OF THE INVENTION

1. Field of the Invention

The present invention provides medical research and diagnostic methods and reagents for detecting and typing HPV.

The methods utilize PCR, a DNA amplification technique widely used in the fields of molecular biology and genetic engineering. The methods can also be used to generate information concerning previously unknown types and subtypes of HPV and consequently has applications in the field of virology.

2. Description of Related Art

Papillomaviruses have been linked to widespread, serious human diseases, especially carcinomas of the genital and oral mucosa. And although genital HPV infection is associated with cancer primarily in women, recent evidence suggests that HPV may play a role in the development of anogenital cancers in men. Broker et al., 1986, Cancer Cells 44:17–36, review the molecular, cellular, and clinical aspects of the papillomaviruses and the relationship of HPVs to cancer. HPV types 6, 11, 16, 18, and 33 are known genital HPV types in the human population, and Broker et al., 1986, Cancer Cells 4:589–594, disclose that HPV types 6, 11, 16, 18, and 33 share significant homology at the DNA level, particularly at the L1 open reading frame.

Identification and typing of HPV is quite important, because different types of HPV pose different risks to the affected individuals. For instance, HPV 16 and HPV 18 have been more consistently identified in higher grades of cervical dysplasia and carcinoma than other HPV types. Webb et al., December 1987, J. Inf. Disease 156(6):912–919, report a method for detecting HPV DNA types that utilizes a reverse-blotting procedure. The procedure involved forming a membrane to which genomic DNA from four different HPV types was bound and then hybridizing labeled DNA from a biological sample to the DNA bound to the membrane. Caussey et al., February 1988, J. Clin. Microbiol. 26(2):236–243 describe similar HPV detection methods.

Shibata et al., Jan. 1988, J. Exp. Med. 167:225–230, disclose the use of PCR to amplify and detect the presence of HPV16 and HPV18 DNA. U.S. Pat. Nos. 4,683,195 and 4,683,202 disclose PCR and the use of PCR to detect the presence or absence of nucleic acid sequence in a sample. PCT Patent Publication No. WO 90/02821 discloses the use of consensus primers and probes to amplify and detect HPV sequences in a sample. The publication also describes type-specific probes for typing the HPV DNA if present in the sample.

Maitland et at., May 1988, Seventh International Papillomavirus Workshop, Abstract, p. 5, report the use of PCR to detect HPV16 in oral and cervical biopsies. In addition, Campione-Piccardo et al., May 1988, Seventh International Papillomavirus Workshop, Abstract, p. 19, report the use of a mixture of primers for the specific amplification by PCR of HPV sequences in types 1a, 5, 6a, 6b, 8, 11, 16, 18, and 33. A number of other researchers disclosed the use of PCR to amplify and detect HPV sequences at the Seventh International Papillomavirus Workshop. Each of the background references described in this section is incorporated herein by reference.

The heterogeneity of the human papillomavirus group is generally described in deVilliers, 1989, J. Virology 63:4898–4903, which is incorporated herein by reference. The genomes of numerous HPV types have been sequenced and/or characterized. For example, for HPV type 6, see de Villiers et al., 1981, J. Virology 40:932–935, and Gissmann and Zur Hausen, 1980, Int. J. Cancer 25:605–609, and Schwartz et al., 1983, EMBO J. 2(12):2341–2348. For HPV type 2, see Gissmann et al., 1982, J. Virology 44:393–400. For HPV type 11, see Dartmann et al., 1986, Virology 151:124–130. For HPV type 16, see Seedorf et al., 1985, Virology 145:181–185. For HPV type 18, see Cole and Danos, 1987, J. Mol. Biol. 193:599–608. For HPV type 31, see Goldsborough et al., 1989, Virology 171:306–311. For HPV 33, see Cole and Streeck, 1986, J. Virology 58:991–995. For HPV 54, see Favre et al., 1990, Int. J. Cancer 45:40–46. For HPV 56, see Lörincz, 1989, J. Gem Virol. 70:3099. These publications are incorporated herein by reference.

Despite the use of PCR to amplify and detect HPV sequences, there still remains a need for a simple and rapid method for both detecting and typing HPV in a biological sample. Patent Publication No. PCT/US89/03747 describes improved methods that offer speed and simplicity for detection and typing HPV in a sample. The methods comprise amplifying a sequence of HPV DNA present in the sample, determining if amplification has occurred and then hybridizing an HPV type-specific probe to the amplified DNA.

SUMMARY OF THE INVENTION

The present invention provides novel compositions and methods for amplifying and typing HPV nucleic acids.

One aspect of the invention relates to novel HPV sequences.

Another aspect of the invention relates to sequence specific probes for determining the HPV type or isolate present in a sample. These novel sequence specific probes enable the detection of previously unknown HPV types and subtypes.

Another aspect of the invention relates to novel primers for amplifying HPV sequences using the polymerase chain reaction. Novel primers are provided for improved amplification of HPV-51. An improved primer pair is provided for the generic amplification of the L1 region of HPV nucleic acids.

Another aspect of the invention relates to methods for classifying an HPV contained in a sample, wherein the methods comprise the steps of:

(a) amplifying HPV nucleic acid;
(b) treating portions of the amplified product formed in step (a) under hybridizing conditions with sets of probes, wherein each set of probes enables the specific detection of a class of HPV types; and
(c) determining the classification of the HPV by the occurrence of hybridization with a probe set.

Another aspect of the invention relates to methods for typing an HPV contained in a sample, wherein the methods comprise the steps of:

(a) amplifying HPV nucleic acid using the polymerase chain reaction (PCR) using a set of primer pairs which enables the amplification of nucleotide sequences of HPV types 6, 11, 16, 18, and 33;

(b) treating the amplified product formed in step (a) under hybridizing conditions with a sequence specific probe which enables the specific detection of an HPV type selected from the group of HPV types consisting of HPV types 26, 31, 35, 39, 40, 42, 45, 51, 52, 53, 54, 55, 56, 57, and 59; and (c) determining the HPV type by the occurrence of hybridization with the probe.

DETAILED DESCRIPTION OF THE INVENTION

To aid in understanding the invention, several terms are defined below.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double- and single-stranded DNA, was well as double- and single-stranded RNA.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, *Meth. Enzymol* 68:90–99; the phosphodiester method of Brown et al., 1979, *Meth. Enzymol.* 68:109–151; the diethylphosphoramidite method of Beaucage et al., 1981, *Tetrahedron Lett.* 22:1859–1862; and the solid support method of U.S. Pat. No. 4,458,066, each incorporated herein by reference. A review of synthesis methods is provided in Goodchild, 1990, *Bioconjugate Chemistry* 1(3):165–187, incorporated herein by reference.

The term "target region" refers to a region of a nucleic acid which is to be analyzed.

The term "hybridization" refers the formation of a duplex structure by two single stranded nucleic acids due to complementary base pairing. Hybridization can occur between complementary nucleic acid strands or between nucleic acid strands that contain minor regions of mismatch. Conditions under which only complementary nucleic acid strands will hybridize are referred to as "stringent hybridization conditions." Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, temperature, and incidence of mismatched base pairs.

The term "probe" refers to an oligonucleotide which forms a duplex structure with a sequence of a target nucleic acid due to complementary base pairing. The probe will contain a "hybridizing region", which is a region of the oligonucleotide corresponding to a region of the target sequence. "Corresponding" means identical to or complementary to the designated nucleic acid. A probe oligonucleotide can either consist entirely of the hybridizing region or can contain additional features which allow for the detection or immobilization of the probe but do not alter the hybridization characteristics of the hybridizing region.

As used herein, the term "probe" also refers to a set of oligonucleotides, wherein the oligonucleotides of the set provide sufficient sequence variants of the hybridization region to enable hybridization with each member of a given set of target sequence variants. For example, because within each HPV type are found subtypes which contain minor sequence variants, a type-specific probe may contain a set of oligonucleotides for hybridization with each of the subtype variant sequences. Additionally, a probe may consist of one or more oligonucleotides which contain mismatches with some or all members of a given set of target sequence variants, but contains sufficient regions of complementarity with each target sequence variant so as to enable hybridization with all target sequence variants under suitable conditions. The term "consensus probes" is used herein to refer to single oligonucleotides complementary to a consensus target sequence, to probes consisting of multiple oligonucleotides, and to combinations thereof.

The terms "sequence-specific oligonucleotide" and "SSO" refer to oligonucleotide probes wherein the hybridizing region is exactly complementary to the sequence to be detected. The use of stringent hybridization conditions under which the probe will hybridize only to that exactly complementary target sequence allows the detection of the specific target sequence. Stringent hybridization conditions are well known in the art (see, e.g., Sambrook et al., 1985, Molecular Cloning—A Laboratory Manual, Cold Spring Harbor Laboratory, Cold Spring Harbor, N.Y., incorporated herein by reference). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Typically, stringent conditions will be those in which the salt concentration is at least about 0.2 molar at pH 7 and the temperature is at least about 60° C. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from 15 to 35 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis.

As used herein, the term "primer" also refers to a set of oligonucleotides, wherein the oligonucleotides of the set provide sufficient sequence variants of the hybridization region to enable hybridization with each member of a given set of target sequence variants, so as to act as a point of initiation of DNA synthesis. Additionally, a primer may consist of one or more oligonucleotides which contain mismatches with some or all members of a given set of target sequence variants, but contains sufficient regions of complementarity with each target sequence variant so as to enable hybridization with all target sequence variants under suitable conditions. The term "consensus primers" is used herein to refer to single oligonucleotides complementary to a consensus target sequence, to primers consisting of multiple oligonucleotides, and to combinations thereof.

The term "thermostable polymerase enzyme" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. A purified thermostable polymerase enzyme is described more fully in U.S. Pat. No. 4,889,818, incorporated herein by reference, and is commercially available from Perkin-Elmer, Norwalk, Conn.

Amplification of DNA by the polymerase chain reaction (PCR) is disclosed in U.S. Pat. Nos. 4,683,195, 4,683,202, and 4,965,188, which are incorporated herein by reference. PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so DNA synthesis by the polymerase proceeds across the region between the primers, effectively doubling the amount of that DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately $2^n$, where n is the number of cycles.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, pipettes (preferably positive displacement pipettes), and pipette tips (preferably with aerosol barriers) for RNA/DNA preparation, reaction mixing, and sample analysis will minimize cross contamination. See also Higuchi and Kwok, 1989, *Nature* 339:237–238 and Kwok, and Orrego, in Innis et al. eds., 1990 PCR Protocols: A Guide to Methods and Applications, Academic Press, Inc., San Diego, Calif., which ale incorporated herein by reference.

Methods to reduce the problem of contamination of a PCR by the amplified nucleic acid from previous reactions are described in PCT patent publication Ser. No. US 91/05210 and U.S. Pat. No. 5,035,996, both incorporated herein by reference. The methods allow the enzymatic degradation of any amplified DNA from previous reactions. PCR amplifications are carried out in the presence of dUTP instead of dTTP. The resulting double-stranded amplification product which incorporates uracil is subject to degradation by uracil-N-glycosylase (UNG), whereas normal thymine-containing DNA is not degraded by UNG. Amplification reaction mixtures are treated with UNG before amplification to degrade all uracil-containing DNA that could serve as target. Because the only source of uracil-containing DNA is the amplified product of a previous reaction, this method effectively eliminates the problem of contamination from previous reactions (carryover). UNG is rendered temporarily inactive by heat, so the denaturation steps in the amplification procedure also serve to inactivate the UNG. New amplification products, therefore, though incorporating uracil, are formed in an UNG-inactivated environment and are not degraded.

Although the polymerase chain reaction is the preferred amplification method, amplification of target sequences in a sample may be accomplished by any known method, such as ligase chain reaction (Wu and Wallace 1988, *Genomics* 4:560–569, incorporated herein by reference), the TAS amplification system (Kwoh et al., 1989, *Proc. Natl. Acad. Sci. USA* 86:1173–1177, incorporated herein by reference), and self-sustained sequence replication (Guatelli et. al., 1990, *Proc. Natl. Acad. Sci. USA* 87:1874–1878, incorporated heroin by reference), each of which provides sufficient amplification so that the target sequence can be detected by nucleic acid hybridization to an SSO probe. Alternatively, methods that amplify the probe to detectable levels can be used, such as Qβ-replicase amplification (Kramer and Lizardi, 1989, *Nature* 339:401–402, and Lorneli et al., 1989, *Clin. Chem.* 35:1826–1831, both of which are incorporated herein by reference). A review of known amplification methods is provided in Abramson and Myers, 1993, *Current Opinion in Biotechnology* 4:41–47, incorporated herein by reference. The term "probe", as used herein, encompasses the sequence-specific oligonucleotides used in the above procedures; for instance, the two or more oligonucleotides used in LCR are "probes" for purposes of the present invention, even though some embodiments of LCR only require ligation of the probes to indicate the presence of an allele.

The choice of primers for use in PCR determines the specificity of the amplification reaction. In the amplification steps of the method of the present invention, "consensus" primers are used that will amplify HPV sequences present in a sample, regardless of type. The consensus primers of the invention can include degenerate primers, mixtures of the oligonucleotides synthesized so that any one of several nucleotides can be incorporated into a primer at a selected position during synthesis. The consensus primers are sufficiently complementary to all types of HPVs to amplify a DNA sequence of any HPV present in the sample. The consensus primers are also designed to amplify a region of DNA that contains sequences that are specific to each major viral type, so the amplified DNA can therefore be used to type the HPV present in the sample. The consensus primers may also be suitable in a ligase chain reaction. For example, in PCT Patent Publication No. WO 89/09835, a process is described that involves the use of ligase to join oligonucleotide segments that anneal to the target nucleic acid. This publication is incorporated herein by reference.

Primers of the invention are generally 18 to 21 nucleotides in length and are designed to have a high degree of homology with HPV sequences. For instance, in the design of the genital HPV consensus primers of the invention, a high degree of homology with all five major genital HPVs (HPV types 6, 11, 16, 18, and 33) was required. The consensus primers also are highly homologous to HPV31

(Goldsborough et al., 1989, *Virology* 171:306–311). For each region to be amplified, two regions of homology are required, one for negative-strand primers and another for positive-strand primers. To identify a homologous region, viral sequences are compared. Once a homologous region is identified, a consensus primer is designed. Degenerate bases can be used in the design to accommodate positions at which an individual virus varies in sequence from the consensus sequence. Preferably, as many degenerate positions are made as is necessary so that all viral sequences have fewer than three mismatches with the consensus primer. The degenerate positions are chosen so that the smallest number of degenerate bases accommodates the largest possible number of viral sequences.

If a particular viral sequence has a large number of mismatches with the consensus sequence, then a type-specific primer is made for that virus. The type-specific primer is mixed with the degenerate primer that was designed for other viruses to make the consensus primer. Any mismatches that are not accommodated by the degenerate positions in the primer should generally be located more than 3 bases from the 3' end of the primer. Likewise, any degenerate positions should be more than 3 bases from the 3' end of the primer.

Estimated minimum and maximum $T_m$s for a degenerate primer should be between 54° C. and 64° C. $T_m$s are estimated by the non-empirical formula: each G or C contributes 4 degrees C. to the $T_m$; each A or T contributes 2° C. to the $T_m$; and the $T_m$ is the sum of the calculated values. Finally, primers should not be designed to span palindromes or repetitive sequences.

The consensus primers of the present invention can also be used to detect HPV types previously uncharacterized. For instance, HPV isolate 88 noted in Table 4 has previously not been reported. Thus, the consensus primers of the invention can be used to amplify DNA sequences of previously unknown HPV types. The amplified DNA can then be sequenced and the sequence data used to generate type-specific probes for use in the method of the present invention.

The present methods have led, and will continue to lead, to the discovery of many previously unknown or uncharacterized HPV types. However, with each new HPV type discovered there comes a corresponding need to make the consensus probe more generic to ensure that the new type will be detected and to make type-specific probes. These new HPV types, primers for amplifying the new types, and probes for detecting and distinguishing the new types are an additional aspect of the present invention.

The first step of the preferred method involves the amplification of an HPV sequence, if that sequence is present in a sample, by PCR using consensus primers. Illustrative consensus primers of the invention are referred to by the region of the HPV genome the primers are used to amplify. The HPV genome is circular. The genome of genital HPVs is oriented as follows: E6, E7, E1, E2, E4, E5a, E5b, L2, L1, and URR. "E" and "L" designations indicate open reading frames and URR indicates the transcriptional regulatory region. Several of the open reading frames overlap, for example, the E4 region is totally contained within the E2 open reading frame. Primers can be used to amplify a sequence that spans one or more regions of the HPV genome. The methods and compositions described herein are particularly suited for amplifying the following HPV regions: L1/URR, L1, E6, E6/E7, E7 through E1, E6 through E1, and E1. It will be clear to one of ordinary skill in the art that the methods disclosed are applicable to any region of the HPV genome and are not limited to the specific embodiments described herein.

Following amplification, a determination is made as to whether amplification has occurred. There are a variety of known means for determining whether amplification has occurred. For example, a portion of the PCR reaction mixture can be subjected to gel electrophoresis and the resulting gel stained with ethidium bromide and exposed to ultraviolet light to observe whether a product of the expected size is present. Alternatively, labeled PCR primers or deoxyribonucleoside 5'-triphosphates are utilized and incorporation of the label into the amplified DNA is determined by, for example, gel electrophoresis and autoradiograph to ascertain if amplification occurred.

Another method for determining if amplification has occurred is to test a portion of PCR reaction mixture for ability to hybridize to a labeled probe designed to hybridize to only the amplified DNA. Probes which hybridize to all HPV types are useful for detecting if amplification has occurred. The present invention provides both consensus and generic probes for the non-type-specific detection of HPV. Alternatively, the determination of amplification and identification of HPV type can be carried out in one step by testing a portion of the PCR reaction mixture for its ability to hybridize to one or more type-specific probes.

Long generic probes provide an alternative to short consensus oligonucleotide probes. Long generic probes comprise all or most of the HPV genomic sequence that lies between the HPV amplification primers. The sequences of one or more HPV types may be combined to provide long probes for enhanced sensitivity and to reduce the likelihood of a false negative result even when a novel variant HPV-type is present. The length of long generic probes increases the hybridization stability and, hence, the tolerance for mismatches.

As used herein, the terms "long probes," "genetic probes," and "long generic probes" all refer to nucleic acid segments used as generic probes for determining if amplification of any HPV has occurred. Long probes are generally greater than 100 nucleotides in length and may be as long as the amplified fragment they are designed to detect. Preferably, long probes are between 100–600 base pairs in length and comprise the full length of the amplified fragment to be detected, but do not include the primer sequences used to generate the amplified segment. For example, in Example II, the long probes are 410 nucleotides long (450, the L1 amplified product length—2×20, the L1 consensus primer length). The long probes are preferably PCR fragments. Most preferably, the PCR primers used to prepare the long probes are nested primers relative to the consensus primers used to amplify the HPV DNA in a sample so that the consensus primer sequences are not included in the probe.

The long probes of the invention may be used in a mixture suitable for generic detection of HPV nucleic acids. However, it is not necessary to include amplified nucleic acids from each major HPV type in a long generic probe mixture in order to achieve generic detection of HPV nucleic acids. In one embodiment, described in Example I, long probes are prepared using HPV-16, HPV-18, and two clinical samples as the PCR template. The example describes a mixture of 410 base pair probes that hybridize to the major HPV types, as well as minor, variant, or novel HPV types. An alternate long probe with modified type specificity is described in Example 4. The long probes may be single-stranded or double-stranded.

Short oligonucleotide consensus probes design is similar to consensus primer design, except that consensus probes generally do not contain as many mismatches as consensus primers. As a result, the $T_m$ for a probe can be higher than the $T_m$ for a primer. However, where a mismatch or degenerate position occurs with respect to the 3' end is not as critical for consensus probes as it is for consensus primers. Clearly, long probes can tolerate a greater number of mismatches.

Type-specific probes are designed so that a given probe will generally have less than 75% similarity with sequences from HPV types distinct from that recognized by the probe. The type-specific probes am usually 18–20 nucleotides in length with estimated $T_m$s in the range of 58° C. to 64° C. The present invention also describes that more than one type-specific probes may be employed for typing. This aspect of the invention provides additional assurance that variant types will be correctly detected and typed. Preferably two type-specific probes are employed that are capable of hybridizing to opposite strands and residing in separate regions of the amplified product.

Thus, an important aspect of the present invention relates to the novel probes provided for use in the present methods. Whether these probes are consensus or generic probes for determining if amplification has occurred or type-specific probes, the probes can be used in a variety of different hybridization formats. Although solution hybridization of a nucleic acid probe to a complementary target sequence is clearly within the scope of the present invention, commercialization of the invention will likely result in the use of immobilized probes and thus a quasi "solid-phase" hybridization.

In one format, referred to as a "dot blot" assay or "forward dot blot" assay, the amplified target is immobilized on a solid support and the target sequences are then hybridized to the labeled probe. The unhybridized fraction of the probe is then removed by washing under suitably stringent conditions, and the support is monitored for the presence of hybridization duplexes.

An alternate method that is quite useful when large numbers of different probes are to be used is a "reverse" dot blot format, in which the amplified sequence is labeled and the probes are immobilized. In this format, unlabeled sequence-specific probes are bound to a membrane and exposed to the labeled sample under appropriately stringent hybridization conditions. Unhybridized labeled sample is then removed by washing under suitably stringent conditions, and the membrane is then monitored for the presence of hybridization duplexes. In one method, the probes are attached to a solid support by virtue of long stretches of T residues; these T residues are added to the probe during synthesis of the probe on an automated synthesizer after the hybridizing sequence is synthesized. When long probes are used in the method, T-tailing is unnecessary, and the probes can be attached directly to the solid support.

Both the forward and reverse dot blot assays can be carded out conveniently in a microwell plate; see U.S. Ser. No. 695,072, filed May 3, 1991, which is a CIP of U.S. Ser. No. 414,542, filed Sep. 29, 1989, now abandoned, incorporated herein by reference. The probes can be attached to bovine serum albumen (BSA), for example, which adheres to the microwell plate, thereby immobilizing the probe.

For classifying HPV types into groups of types, such as oncogenic and non-oncogenic types, as described in Example 7, it is not necessary to distinguish among the types within each group. It is sufficient to detect hybridization with any of a number of type-specific probes. In this case, it is desirable to pool probes. However, the total number of probes which can be attached to a microwell plate by either passive coating or by adsorption of probes conjugated to bovine serum albumin (BSA) is limited. Because the total number of bound probes is constant, pooling probes can decrease the number of each probe and, hence, decrease sensitivity. On method of maintaining sensitivity is to incorporate multiple hybridizing sequences in each probe. Probe hybridizing sequences can be linked such that a multiplicity of hybridizing sequences are attached to the plates through a single binding site. In a preferred method, each probe contains between two and four probe hybridizing sequences linked linearly. A linked probe structure can be a single oligonucleotide containing a series of individual probe sequences arranged consecutively. Alternatively, individual probe oligonucleotides sequences may also be attached to each other through spacers of various lengths. Probes may also be constructed using a branching structure such that the hybridizing regions are each attached to the same base structure, or in structures that are hybrids of a linear and branched structure.

Another suitable assay system is described in U.S. Ser. No. 563,758, filed Aug. 6, 1990, incorporated herein by reference, in which a labeled probe is added during the PCR amplification process. Any SSO probe that hybridizes to target DNA during each synthesis step is degraded by the 5' to 3' exonuclease activity of a polymerase, e.g., Taq polymerase. The degradation product from the probe is then detected. Thus, the presence of the breakdown product indicates that the hybridization between the SSO probe and the target DNA occurred.

Many methods for labeling nucleic acids, whether probe or target, are known in the art and are suitable for purposes of the present invention. Suitable labels may provide signals detectable by fluorescence, radioactivity, colorimetry, X-ray diffraction or absorption, magnetism, enzymatic activity, and the like. Suitable labels include fluoruphores, chromophores, radioactive isotopes (particularly $^{32}P$ and $^{125}I$), electrondense reagents, enzymes and ligands having specific binding partners. Enzymes are typically detected by their activity. For example, horse-radish-peroxidase (HRP) can be detected by its ability to convert diaminobenzidine to a blue pigment. A preferred method for HRP based detection uses tetramethyl-benzidine (TMB) as described in *Clin. Chem.* 33:1368 (1987). An alternative detection system is the Enhanced Chemiluminescent (ECL) detection kit commercially available from Amersham, Arlington Heights, Ill. The kit is used in accordance with the manufacturer's directions.

Probes may be labeled with radioactive phosphorous $^{32}P$, by treating the probes with polynucleotide kinase in the presence of radiolabeled ATP. However, for commercial purposes non-radioactive labeling systems may be preferred, such as, horseradish peroxidase-avidin-biotin or alkaline phosphatase detection systems. HRP can be used in a number of ways. For example, if the primer or one or more of the dNTPs utilized in a PCR amplification has been labeled (for instance, the biotinylated dUTP derivatives described by Lo et al., 1988, *Nuc. Acids Res.* 16:8719) instead of the probe, then hybridization can be detected by assay for the presence of labeled PCR product. In a preferred embodiment, probes are biotinylated and detected with the ECL system described above. For example, biotinylated probes were prepared by direct biotinylation of the oligonucleotide rather than incorporation of biotin-dUTP during PCR. For 5' biotinylation of oligonucleotides direct solid phrase synthesis using biotin containing phosphoramidites was done according to Alves et al., 1989, *Tetra. Let* 30:3098; Cocuzza, 1989, *Tetra Let.* 30:6287; and Barabino et al., 1989, *EMBO J.* 8:4171. Solid phase synthesis of biotinylated oligonucleotides at any internal or terminal (5' or 3') position is also suitable for preparing biotinylated primers and probes (Pieles et al., 1989, *NAR.* 18:4355, and Misiura et. al., 1989, *NAR* 18:4345).

Alternatively, biotinylated probes can be prepared using terminal deoxynucleotide transferase (TdT) (Boeringer Mannheim) as follows. An 8:1 molar ratio of biotin-dUTP: oligonucleotide provided 80% derivatization with each molecule bearing 1 or more terminal biotin dUMPs. The tailing reaction contained 100 pmoles of oligonucleotide and 800 pmoles of biotin-dUTP in a 10–20 µl reaction using 3–10 units of TdT for 30–60 minutes at 37° C. The reaction buffer was prepared according to the enzyme specifications from the manufacturer. The reaction was stopped with EDTA and purified from 2.5M $NH_4Ac$, by ethanol precipitation (twice) using 10 µg tRNA, ssDNA, glycogen or linearized acrylamide as a carrier (see *Focus* 11(3):57–58). Tailed oligonucleotides can be probes for targets fixed to a solid support. The Amersham ECL system provides an appropriate means for detecting these compounds (see *Nature* 346:297 [1990]).

In one embodiment of the invention biotinylated probes are prepared by incorporating biotin-dUTP into the amplification reaction for preparing long probes.

Alternatively, probes are conjugated to HRP, for example, according to the method disclosed in WO 89/2932, and Beaucage et al., 1981, *Tetra. Lett.* 22:1859–1862. These references are incorporated herein by reference. For HRP conjugated probes, the hybridization buffer is adjusted to decrease the wash temperature required for removing non-specifically hybridized probe without the risk of denaturing the HRP enzyme. However, HRP conjugated probes are not used in the preferred embodiment. Whatever the labeling system used, once a determination has been made that the L1 consensus probe has hybridized to amplified DNA present in the sample, the amplified DNA is typed to determine the HPV types present in the sample.

Those skilled in the art also recognize from the present disclosure that the method of the present invention can be carded out in a variety of ways. The present method is applicable to any human papillomavirus and especially preferred for detecting and typing genital HPVs. The method can be used to detect isolate-to-isolate variation within a particular HPV type and can also be used to screen for significant changes in the HPVs present in a patient. In one embodiment of the invention, consensus primers to more than one region of HPV DNA will be used, ensuring that if any portion of the HPV genome has been deleted, other regions can still be detected. In a similar fashion, the typing of the amplified DNA can be done using a variety of type-specific probes that recognize different regions of the amplified DNA. In a preferred embodiment, probes capable of hybridizing to at least two regions of the amplified DNA are employed to increase the likelihood of correctly typing HPV variants.

An internal amplification control is preferably used to assure the competency of a sample for amplification and reduce the likelihood of false negative results. The internal control can be a genomic segment of DNA known to be present in a sample of human origin. For example, the β-globin gene provides a suitable positive control amplification target. In one embodiment of the invention, β-globin primers are included in the PCR reaction mixture for amplifying the L1 region of the HPV genome. β-globin primers GH20 (Seq ID No. 101) and PC04 (Seq ID No. 102) produce a 268 base pair product.

| GH20 | Seq ID No. 101 | GAAGAGCCAAGGACAGGTAC |
|---|---|---|
| PC04 | Seq ID No. 102 | CAACTTCATCCACGTTCACC |

The β-globin amplified segment is readily distinguished from the L1 amplified product using gel electrophoresis by size (268 bp vs. 450 bp). For a positive control, when E6 consensus primers are used, other methods of detecting the β-globin product are desirable because the E6 product is 240 base pair in size and, therefore, is not necessarily easily distinguished. In that event, a β-globin probe can be used to detect the amplified product; PC03 (Seq ID No. 103) is a suitable oligonucleotide probe.

| PC03 | Seq ID No. 103 | ACACAACTGTGTTCACTAGC |
|---|---|---|

Alternatively, the β-globin and HPV amplification reactions can be run in parallel and analyzed individually. Similarly, it may be desirable to include positive and negative HPV controls in practicing the present methods for detecting and typing any HPV. For example, in one embodiment of the invention, plasmids containing genomic segments of HPVs 6, 11, 16, 18, and 33 are included. So long as the consensus primers, probes and type-specific probes used in the method can amplify and hybridize to the control nucleic acid, it is not essential that the control comprises the entire viral genome of each HPV. Example 2 describes specific HPV plasmids used as positive control; however, these specific plasmids are non-essential aspects of the invention and numerous cloned HPVs are described in the literature.

Those skilled in the art recognize that the present invention can also be used to detect HPV mRNA present in a sample. The expression of certain HPV mRNA species, particularly E6 and E7 mRNAs, may be indicative of the likelihood that an HPV infection will progress to carcinoma. To detect an HPV mRNA by the method of the present invention, the mRNA can be treated with reverse transcriptase in an appropriate reaction mixture to synthesize a cDNA molecule. The primer used in the reverse transcription reaction can be a consensus primer of the invention or can be a different oligonucleotide that hybridizes near the 3' end of the mRNA. Although random hexamers are not specific for the 3' end of the molecule, they are suitable for reverse transcription of RNA to provide a cDNA template for amplifying HPV nucleic acids. This cDNA copy is then made into a double stranded DNA molecule, which can be detected and typed in accordance with the method of the present invention.

The present invention may be assembled as a kit for detecting and typing HPV. Such a kit would include consensus primers and type-specific probes. A preferred kit also includes means for determining if amplification has occurred, such as a consensus probe or long probe. Additional kit components may include and are not limited to any of the following: PCR buffers and enzymes; positive control HPV or non-HPV DNAs; positive control primers, for example, β-globin primers; a positive control probe; primers for preparing long probes; means for detecting hybridized probes; and instructions for amplifying, detecting, and typing HPV.

Those skilled in the art recognize that the specific primers and probes disclosed herein are merely illustrative of the invention. For instance, because the primers and many of the probes of the invention are single-stranded DNA molecules, and because the target DNA (HPV DNA in a sample) is double-stranded DNA, useful primers and probes of the invention can be constructed merely by synthesizing primers and probes complementary to those specifically disclosed herein. The primers and probes of the invention can also be prepared to amplify and detect sequence variations within areas of HPV genomes other than those specifically exemplified herein.

The methods of the present invention, although applicable to any HPV, are exemplified below with reference to genital and dermal HPV types. Furthermore, primers and probes can be targeted to areas of the HPV genome other than those described below, provided that the particular area targeted can be amplified using consensus primers and the amplified DNA can be typed using type-specific probes.

Throughout the specification nucleotides are designated as follows.

| Symbol | Meaning | Origin |
|---|---|---|
| G | G | Guanine |
| A | A | Adenine |
| T | T | Thymine |
| C | C | Cytosine |
| R | G or A | puRine |
| Y | T or C | pYrimidine |
| M | A or C | aMino |
| K | G or T | Keto |
| S | G or C | Strong interaction (3 H bonds) |
| W | A or T | Weak interaction (2 H bonds) |

-continued

| Symbol | Meaning | Origin |
|---|---|---|
| H | A or C or T | not-G, H follows G in the alphabet |
| B | G or T or C | not-A, B follows A |
| V | G or C or A | not-T (not-U), V follows U |
| D | G or A or T | not-C, D follows C |
| N | G or A or T or C | aNy |

L1/E6 Region

In one embodiment, the L1/E6 consensus primer combinations of the invention are designed to amplify a sequence of DNA from any genital HPV. The amplified sequence extends from L1 across the URR and into E6 and thus contains portions of the L1 and E6 regions with the URR region sandwiched in between the L1 and E6 regions. Thus, the consensus primer pairs consist of a first primer specific for a sequence in the L1 region and a second primer specific for a sequence in the E6 region. As shown in Table 1, below, the first L1-specific primer can be either FS10 (Seq ID No. 21), FS17 (Seq ID No. 264), or MY01 (Seq ID No. 263), while the second, E6-specific primer is at least a 1:1 mixture of JS15 and JS16 (Seq ID Nos. 265 and 266), although the mixture can also contain more JS15 than JS 16 (Seq ID Nos. 265 and Table 1 also depicts the sequence each primer and the corresponding sequence (and nucleotide position of that sequence) as it occurs in the genomes of several well-known genital HPVs (Types 6, 11, 16, 18, and 33). A dash in a sequence indicates that the genomic sequence is identical to the primer sequence.

TABLE 1

L1/E6 Consensus Primers and Amplification Products

L1 Consensus Positive Strand Primers

| | | | | | | | | | | | | | | | | | | | | | | | | | |
|---|---|---|---|---|---|---|---|---|---|---|---|---|---|---|---|---|---|---|---|---|---|---|---|---|---|
| FS10 (Seq ID No. 21) | C | T | G | T | G | G | T | A | G | A | T | A | C | C | A | C | A | C | G | C | A | G | T | A | C |
| HPV06 6770 | — | — | — | — | — | — | — | — | — | — | — | — | — | — | — | — | — | — | — | — | — | — | — | — | — |
| HPV11 6756 | — | — | — | — | — | — | — | — | — | — | — | — | — | — | — | — | — | — | — | — | — | — | — | — | — |
| HPV16 6633 | — | — | — | — | T | — | — | T | — | — | — | — | — | — | — | T | — | — | — | — | — | — | — | — | — |
| HPV18 6587 | — | — | — | — | — | — | — | — | — | — | — | — | — | — | — | — | — | T | — | — | — | — | — | — | — |
| HPV33 6587 | — | — | — | — | — | — | — | — | — | — | — | — | — | — | — | — | — | T | — | — | — | — | — | — | — |
| FS17 (Seq ID No. 264) | 5' | G | A | T | C | A | G | T | T | T | C | C | Y | Y | T | K | G | G | A | C | G | | | | |
| MY01 (Seq ID No. 263) | 5' | G | A | T | C | A | G | T | W | T | C | C | Y | Y | T | K | G | G | A | C | G | | | | |
| HPV06 7151 | — | — | — | — | — | — | — | — | A | — | — | — | T | T | — | G | — | — | — | — | — | | | | |
| HPV11 7136 | — | — | — | — | — | — | — | — | T | — | — | — | C | C | — | T | — | — | — | — | — | | | | |
| HPV16 7015 | — | — | — | — | — | — | — | — | T | — | — | — | T | T | — | A | — | — | — | — | — | | | | |
| HPV18 6933 | — | — | — | — | — | — | A | — | A | — | — | — | C | C | — | T | — | — | — | — | — | | | | |
| HPV33 6968 | — | — | — | — | — | — | — | — | T | — | — | — | T | T | — | G | — | — | — | — | — | | | | |

URR/E6 Consensus Negative Strand Primer

| | | | | | | | | | | | | | | | | | |
|---|---|---|---|---|---|---|---|---|---|---|---|---|---|---|---|---|---|
| JS15 (Seq ID No. 265) | 5' | C | C | G | T | T | T | T | C | G | G | T | T | S | A | A | C | C | G |
| HPV06 60 | — | — | — | — | — | — | — | — | — | — | — | — | — | G | — | — | — | — | — |
| HPV11 60 | — | — | — | — | — | — | — | — | — | — | — | — | — | G | — | — | — | — | — |
| HPV16 60 | — | — | — | G | — | — | — | — | — | — | — | — | — | C | — | — | — | — | — |
| HPV33 64 | — | — | — | — | — | — | — | — | — | — | — | — | — | G | — | — | — | — | — |
| JS16 (Seq ID No. 266) | 5' | C | C | G | T | T | T | T | C | G | G | T | C | C | C | G | A | C | C | G |
| HPV18 68 | — | — | — | — | — | — | — | — | — | — | — | — | — | — | — | — | — | — | — | — |

Predicted Sizes Of PCR Products

| | +PRIMER | FS10 (Seq ID No. 21) | FS17 or MY01 (Seq ID Nos. 264 and 263) |
|---|---|---|---|
| | PRIMER | JS15 and JS16 (Seq ID Nos. 265 and 266) | JS15 and JS16 (Seq ID Nos. 265 and 266) |
| HPV06 | | 1192 bp | 822 bp |
| HPV11 | | 1235 bp | 856 bp |
| HPV16 | | 1387 bp | 958 bp |
| HPV18 | | 1367 bp | 932 bp |
| HPV33 | | 1434 bp | 1005 bp |

As shown in Table 1, FS10 (Seq ID No. 21) is a 25-mer that has 3 mismatches with HPV16 and 1 mismatch with HPV18 and HPV33. FS17 (Seq ID No. 264) is a degenerate primer with 1 or 2 mismatches to different HPVs. MY01 (Seq ID No. 263) is similar to FS17 (Seq ID No. 264), contains 1 more degenerate base to decrease mismatches and to potentially cover a wider range of HPVs. JS15 (Seq ID No. 265) is a degenerate 18-mer for the negative strand in E6 of HPVs 6, 11, 16, and 33, whereas JS16 (Seq ID No. 266) is a 19-mer serving the same function for HPV18.

Once a sample has been treated with the L1/E6 primers shown above under conditions suitable for PCR, the method of the invention requires the determination of whether amplification has occurred. If amplification has occurred with the L1/E6 primers, HPV sequences are present in the sample. In one aspect of the invention, a consensus probe is used to determine if amplification has occurred. Alternatively, amplification of HPV DNA using the L1/E6 consensus primers FS10 (Seq ID No. 21), JS15 (Seq ID No. 265), and JS16 (Seq ID No. 266) can be detected using the L1/E6 consensus primer FS17 (Seq ID No. 264) or MY01 (Seq ID No. 263).

The present invention provides a number of type-specific probes for use with the L1/E6 consensus primers of the invention. These probes are set forth in Table 2, below. Those skilled in the art will recognize that although the specific primers and probes of the invention exemplified herein have a defined number of nucleotide residues, one or more nucleotide residues may be added or deleted from a given primer or probe typically without great impact on the suitability of that primer or probe in the present methods.

TABLE 2

HPV Typing Probes For Use with L1/E6 Consensus Primers

| Specificity | Sequence ID No. | Sequence | Size | Designation |
|---|---|---|---|---|
| HPV6  | 1 | 5'CCAAACAGTAAGAGC        | (15-mer) | FS18 |
| HPV11 | 2 | 5'GGCTGTAGAGGGCTTAGAC    | (19-mer) | FS19 |
| HPV16 | 3 | 5'GGTTGAAGCTACAAAATGGGCC | (22-mer) | JS17 |
| HPV18 | 4 | 5'GTAGCGCACCTGGACAGG     | (18-mer) | FS21 |
| HPV33 | 5 | 5'CAGGTAGTGACTCAC        | (15-mer) | FS22 |

FS19 (Seq ID No. 2) and JS17 (Seq ID No. 3) can specifically detect HPV11 and HPV16, respectively. FS18 (Seq ID No. 1) shows some hybridization with the HPV11 PCR product. UWGCG GAP program analysis comparing FS18 (Seq ID No. 1) sequence and HPV 11 sequence indicates a 73% homology of FS 18 (Seq ID No. 1) to HPV11 in the amplified region. The cross-hybridization could be minimized by increasing the stringency of washing. FS21 (Seq ID No. 4) was specific for HPV 18.

L1 Region

The L1/E6 primers disclosed above provide for the amplification of relatively large segments of HPV DNA. However, use of primers that result in shorter PCR products can have several advantages, including reduced extension and denaturation time and decreased denaturation temperature. The L1 consensus primers of the invention are illustrative of primers designed to amplify relatively small segments of the HPV genome to achieve such advantages. The L1 consensus primers, MY11 (Seq ID No. 267), MY09 (Seq ID No. 269), PEG01 (Seq ID No. 268), and PEG02 (Seq ID No. 270), amplify a region of the L1 open reading frame and are depicted in Table 3, below.

TABLE 3

L1 Consensus Primers and Amplification Products

L1 Consensus Positive Strand Primers

| | | | | | | | | | | | | | | | | | | |
|---|---|---|---|---|---|---|---|---|---|---|---|---|---|---|---|---|---|---|
| MY11 (Seq ID No. 267) | 5' | G | C | M | C | A | G | G | G | W | C | A | T | A | A | Y | A | A | T | G | G |
| PEG01 (Seq ID No. 268) | | — | — | — | — | — | — | — | — | D | — | — | Y | — | — | — | — | — | — | — |
| HVP06 6722 | | — | — | C | — | — | — | — | — | A | — | — | — | — | — | C | — | — | — | — |

TABLE 3-continued

L1 Consensus Primers and Amplification Products

| | | | | | | | | | | | | | | | | | | | | | |
|---|---|---|---|---|---|---|---|---|---|---|---|---|---|---|---|---|---|---|---|---|---|
| HVP11 6707 | — | — | T | — | — | — | — | — | A | — | — | — | — | — | C | — | — | — | — | — | — |
| HPV16 6584 | — | — | A | — | — | — | — | — | C | — | — | C | — | — | T | — | — | — | — | — | — |
| HPV18 6558 | — | — | A | — | — | — | — | — | T | — | — | — | — | — | C | — | — | — | — | — | — |
| HPV31 | — | — | T | — | — | — | — | — | A | — | — | C | — | — | T | — | — | — | — | — | — |
| HPV33 6539 | — | — | A | — | — | A | — | — | T | — | — | — | — | — | T | — | — | — | — | — | — |

L1 Consensus Negative Strand Primers

| | | | | | | | | | | | | | | | | | | | | | |
|---|---|---|---|---|---|---|---|---|---|---|---|---|---|---|---|---|---|---|---|---|---|
| MY09 (Seq ID No. 269) | 5' | C | G | T | C | C | M | A | R | R | G | G | A | W | A | C | T | G | A | T | C |
| PEG02 (Seq ID No. 270) | | — | — | — | — | — | — | — | — | — | — | — | — | — | Y | — | — | — | — | — | — |
| HPV06 7171 | | — | — | — | — | — | C | — | A | A | — | — | — | — | T | — | — | — | — | — | — |
| HPV11 7155 | | — | — | — | — | — | A | — | G | G | — | — | — | — | A | — | — | — | — | — | — |
| HPV16 7035 | | — | — | — | — | — | T | — | A | A | — | — | — | A | — | — | — | — | — | — | — |
| HPV18 7012 | | — | — | — | — | — | A | — | G | G | — | — | — | T | — | T | — | — | — | — | — |
| HPV31 | | — | — | A | — | — | C | — | G | T | — | — | — | A | — | — | — | — | — | — | — |
| HPV33 6988 | | — | — | — | — | — | C | — | A | A | — | — | — | A | — | — | — | — | — | — | — |
| HPV54 | | — | — | A | — | — | A | — | — | G | — | — | — | A | — | — | — | — | G | — | — |

Predicted sizes of PCR products from the
MY11 (Seq ID No. 267) and MY09 (Seq ID No. 269)
L1 Consensus Primer Pair HPV06 448 bp
HPV11 448 bp
HPV16 451 bp
HPV18 454 bp
HPV33 448 bp

---

PEG01 (Seq ID No. 268) and PEG02 (Seq ID No. 270) are modifications of MY11 (Seq ID No. 267) and MY09 (Seq ID No. 269) which amplify the various HPV types with more uniform efficiency. A uniform amplification efficiency allows the detection of the various HPV types with a uniform sensitivity.

The methods of the present invention am useful for detecting any HPV DNA. A preferred embodiment of the HPV typing methods of the present invention comprises amplification of HPV sequences, if present in the sample, with the L1 consensus primers MY09 (Seq ID No. 269) and MY11 (Seq ID No. 267); determination of amplification by hybridization of a portion of the PCR reaction mixture with a generic HPV long probe; and finally, type determination with type-specific probes. This embodiment is useful for detecting and typing nucleic acids of both dermal and genital HPVs including genital HPV types 6, 11, 16, 18, 26, 30, 31, 33, 35, 39, 40, 42, 43, 45, 51, 52, 53, 54, 55, 57, 58, and 59, as well as dermal HPV types 5, 8, 27, 41, 47, and 48. At present, more than 60 unique HPV types have been identified. These are briefly described in deVilliers, 1989, *J. Virol.* 63:4898. The present invention is useful for typing known HPV types as well as identifying unique types or variants. To determine if amplification of HPV DNA sequences has occurred in a sample that has been treated with the L1 consensus primers of the invention, a portion of the PCR reaction mixture can be hybridized with L1 consensus probes, depicted in Table 4. Additional L1 consensus probes are provided below and in Example 8.

TABLE 4

L1 Consensus Probes

| | | | | | | | | | | | | | | | | | | | | | | | | |
|---|---|---|---|---|---|---|---|---|---|---|---|---|---|---|---|---|---|---|---|---|---|---|---|---|
| FS10 (Seq ID No. 21) | 5' | C | T | G | T | G | G | T | A | G | A | T | A | C | C | A | C | A | C | G | C | A | G | T | A | C |
| MY18 (Seq ID No. 106) | 5' | — | — | — | — | T | — | — | T | — | — | — | — | — | — | — | T | — | — | — | — | — | — | — | — | — |
| MY19 (Seq ID No. 271) | 5' | — | — | — | — | — | — | — | — | — | — | — | — | — | — | — | — | T | — | — | — | — | — | — | — | — |

Sequence of HPV types in Region of Consensus Probe

| | | | | | | | | | | | | | | | | | | | | | | | | |
|---|---|---|---|---|---|---|---|---|---|---|---|---|---|---|---|---|---|---|---|---|---|---|---|---|
| HPV6 6771 | 5' | C | T | G | T | G | G | T | A | G | A | T | A | C | C | A | C | A | C | G | C | A | G | T | A | C |
| HPV11 6756 | 5' | — | — | — | — | — | — | — | — | — | — | — | — | — | — | — | — | — | — | — | — | — | — | — | — | — |
| HPV16 6631 | 5' | — | — | — | — | T | — | — | T | — | — | — | — | — | — | — | T | — | — | — | — | — | — | — | — | — |
| HPV18 6607 | 5' | — | — | — | — | — | — | — | — | — | — | — | — | — | — | — | T | — | — | — | — | — | — | — | — | — |
| HPV33 6588 | 5' | — | — | — | — | — | — | — | — | — | — | — | — | — | — | — | T | — | — | — | — | — | — | — | — | — |
| Isolate 36 | 5' | — | — | — | — | T | — | — | G | — | — | — | — | — | — | — | T | — | — | C | A | — | A | — | — | C | — | — |
| Isolate 88 | 5' | — | A | — | — | — | — | — | — | — | — | — | — | — | — | — | T | — | — | T | — | — | — | — | — | C | — | — |

---

As noted above, the diversity of HPV types may mandate the use of longer consensus probes that contain almost all of the amplified sequence except that portion corresponding to the primers used in the amplification step of the present method. This diversity in HPV types also demonstrates the need for the type-specific probes provided by the present invention. In a preferred embodiment, the method utilizes a generic probe comprising PCR fragments. The PCR fragments provide long probes for the use as consensus probes for determining if amplification has occurred. According to Example 1, a generic probe was synthesized from the 450 base pair L1 PCR fragments of HPV-16, HPV-18, and the highly divergent isolates PAP88 and PAP238B. The generic probe described in Example 1 comprises segments approximately 400 base pairs in length and can be prepared using the primers depicted below. The primers are used in pairs corresponding to the target; i.e., MY74 (Seq ID No. 6) and MY75 (Seq ID No. 7) for HPV16, MY76 (Seq ID No. 8) and MY77 (Seq ID No. 9) for HPV18, MY47 (Seq ID No. 10) and MY48 (Seq ID No. 11) for PAP88, and MY49 (Seq ID No. 12) and MY50 (Seq ID No. 13) for PAP238B. An alternate generic probe is described in Example 4, below.

Internal PCR Primers for Generic Probe

| Name | Seq ID No. | Sequence | Target |
|------|-----------|----------|--------|
| MY74 | 6 | CATTTGTTGGGGTAACCAAC | HPV16 |
| MY75 | 7 | TAGGTCTGCAGAAAACTTTTC | HPV16 |
| MY76 | 8 | TGTTTGCTGGCATAATCAAT | HPV18 |
| MY77 | 9 | TAAGTCTAAAGAAAACTTTTC | HPV18 |
| MY47 | 10 | CATATGCTGGGGTAATCAGG | PAP88 |
| MY48 | 11 | CAGGTCTGCAGAAAAGCTGT | PAP88 |

Internal PCR Primers for Generic Probe

| Name | Seq ID No. | Sequence | Target |
|------|-----------|----------|--------|
| MY49 | 12 | TATTTGTTGGGGCAATCAG | PAP238B |
| MY50 | 13 | CTAAATCTGCAGAAAACTTTT | PAP238B |

Practice of the present invention has led to the discovery of many previously uncharacterized HPV types. These new sequences are an important aspect of the present invention, as are the probes that will hybridize to these sequences in a type-specific fashion. These new sequences are depicted below. Degenerate nucleotides are as defined above and correspond to the degenerate nucleotides in the primers used to amplify the region or to variation within the type.

The DNA Sequences of the L1 Amplified Regions of HPV

Isolates 36A - Seq. ID No. 14

| 1 | GCMCAGGGWC | ATAAYAATGG | TATATGTTGG | CACAATCAAT | TGTTTTTAAC |
|---|------------|------------|------------|------------|------------|
| 51 | AGTTGTAGAT | ACTACTCGCA | GCACCAATCT | YTCTGTGTGT | GCTTCTACTA |
| 101 | CTTCTCCTAT | TCCTAATGAA | TACACACCTA | CCAGTTTTAA | AGAATATGCC |
| 151 | AGACATGTGG | RGGAATTTGA | TTTGCAGTTT | ATAYTTCAAC | TGTGTAAAAT |
| 201 | AACWTTAACT | ACAGAGGTAA | TGTCATACAT | TCATAATATG | AATACCACTA |
| 251 | TTTTGGAGGA | TTGGAATTTT | GGTRTTACAC | CACCTCCTAC | TGCTARTTTA |
| 301 | GTTGACACAT | ACCGTTTTGT | TCAATCTGCT | GCTGTAACTT | GTCAAAAGGA |
| 351 | CACCGCACCG | CCAGTTAAAC | AGGACCCTTA | TGACAAACTA | AAGTTTTGGA |
| 401 | CTGTAAATCT | TAAGGAAAGG | TTTTCTGCAG | ATCTTGATCA | GTWTCCYYTK |
| 451 | GGACG | | | | |

Isolate 36B - Seq ID No. 15

| 1 | GCMCAGGGWC | ATAAYAATGG | TATATGTTGG | GGAAATCAGC | TATTTTTAAC |
|---|------------|------------|------------|------------|------------|
| 51 | TGTCGTTGAT | ACTACCCGTA | GTACTAACAT | GACTTTGTGY | GCCACTGCAA |
| 101 | CATCTGGTGA | TACATATACA | GCTGCTAATT | TTAAGGAATA | TTTAAGCAT |
| 151 | GCTGAAGAAT | ATGATGTGCA | ATTTATATTT | CAATTGTGTR | AAATAACATT |
| 201 | AACTGTTGAA | GTTATGTCAT | ATATACACAA | TATGAATCCT | AACATATTAG |
| 251 | AGGAGTGGAA | TGTTGGTGTT | GCACCACCAC | CTTCAGGAAC | TTTAGAAGAT |
| 301 | AGTTATAGGT | ATGTACAATC | AGAAGCTATT | CGCTGTCAGG | CTAAGGTAAC |
| 351 | AACGCCAGAA | AAAAAGGATC | CTTATTCAGA | CTTTTCCTTT | TGGGAGGTAA |
| 401 | ATTTATCTGA | AAAGTTTTCT | ACTGATTTAG | GATCAGTWTC | CYYTKGGACG |

Isolate 88 - Seq ID No. 16

| 1 | GCMCAGGGWC | ATAAYAATGG | CATATGCTGG | GGTAATCAGG | TATTTGTTAC |
|---|------------|------------|------------|------------|------------|
| 51 | TGTTGTGGAT | ACTACCAGAA | GCACCAACAT | GACTATTAAT | GCAGCTAAAA |
| 101 | GCACATTARC | TAAATATGAT | GCCCGTGAAA | TCAATCAATA | CCTTCGCCAT |
| 151 | GTGGAGGAAT | ATGAACTACA | GTTTGTGTTT | CAACTTTGTA | AAATAACCTT |
| 201 | AACTGCAGAR | GTTATGGCAT | ATTTGCATAA | TATGAATAAT | ACTTTATTRG |
| 251 | ACGATTGGAA | TATTGGCTTA | TCCCCACCAG | TTGCAACTAG | CTTAGAGGAT |
| 301 | AAATATAGGT | ATATTAAAAG | CACAGCTRTT | ACAYGTCAGA | GGGAACAGCC |
| 351 | CCCTGCAGAA | AAGCAGGATC | CCCTGGCTAA | ATATAAGTTT | TGGGAAGTTA |
| 401 | ATTTACAGGA | CAGCTTTTCT | GCAGACCTGG | GATCAGTWTC | CYYTKGGACG |

Isolate 238A - Seq ID No. 17

| 1 | GCMCAGGGWC | ATAAYAATGG | TATTTGTTGG | CATAATCART | TATTTTTAAC |
|---|------------|------------|------------|------------|------------|
| 51 | TGTTGTAGAT | ACTACTAGAA | GCACTAATTT | TTCTGTATGT | GTAGGTACAC |
| 101 | AGGCTAGTAG | CTCTACTACA | ACGTATGCCA | ACTCTAATTT | TAAGGAATAT |
| 151 | TTAAGACATG | CAGAAGAGTT | TGATTTACAG | TTTGTTYTTC | AGTTATGTAA |
| 201 | AATTAGTTTA | ACTACTGAGG | TAATGACATA | TATACATTCT | ATGAATTCTA |
| 251 | CTATATTGGA | AGAGTGGAAT | TTTGGTCTTA | CCCCACCACC | GTCAGGTACT |
| 301 | TTAGAGGAAA | CATATAGATA | TGTAACATCA | CAKGCTATTA | GTTGCCAACG |
| 351 | TCCTCAACCT | CCTAAAGAAA | CAGAGGACCC | ATATGCCAAG | CTATCCTTTT |
| 401 | GGGATGTAGA | TCTTAAGGAA | AAGTTTTCTG | CAGAATTAGA | TCAGTWTCCY |
| 451 | YTKGGACG | | | | |

Isolate 238B - Seq ID No. 18

| 1 | GCMCAGGGWC | ATAAYAATGG | TATTTGTTGG | GGCAATCAGT | TATTTGTTAC |
|---|------------|------------|------------|------------|------------|
| 51 | TGTGGTAGAT | ACCACACGTA | GTACCAATAT | GTCTGTGTGT | GCTGCAATTG |
| 101 | CAAACAGTGA | TACTACATTT | AAAAGTAGTA | ATTTTAAAGA | GTATTTAAGA |
| 151 | CATGGTGAGG | AATTTGATTT | ACRATTTATA | TTTCAGTTAT | GCAAAATAAC |

The DNA Sequences of the L1 Amplified Regions of HPV

| | | | | | |
|---|---|---|---|---|---|
| 201 | ATTATCTGCA | GACATAATGA | CATATATTCA | CAGTATGAAT | CCTGCTATTT |
| 251 | TGGAAGATTG | GAATTTTGGA | TTGACCACAC | CTCCCTCAGG | TTCTTTAGAG |
| 301 | GATACCTATA | GGTTTGTAAC | CTCACAGGCC | ATTACATGTC | AAAAARCTGC |
| 351 | CCCCCAAAAG | CCCAAGGAAG | ATCCATTTAA | AGATTATGTA | TTTTGGGAGG |
| 401 | TTAATTTAAA | AGAAAAGTTT | TCTGCAGATT | TAGATCAGTW | TCCYYTKGGA |
| 451 | CG | | | | |

Isolate 155A and 155B - Seq ID No. 19

| | | | | | |
|---|---|---|---|---|---|
| 1 | TATATGCTGG | TTTAATCAAT | TGTTTGTCAC | GGTGGTGGAT | ACCACCCGCA |
| 51 | GCACCAATTT | TACTATTAGT | GCTGCTACCA | ACACCGAATC | AGAATATAAA |
| 101 | CCTACCAATT | TTAAGGAATA | CCTAAGACAT | GTGGAGGAAT | ATGATTTGCA |
| 151 | GTTTATATTC | CAGTTGTGTA | AGGTCCGTCT | GACTCCAGAG | GTCATGTCCT |
| 201 | ATTTACATAC | TATGAATGAC | TCCTTATTAG | ATGAGTGGAA | TTTTGGTGTT |
| 251 | GTGCCCCCTC | CCTCCACAAG | TTTAGATGAT | ACCTATAGGT | ACTTGCAGTC |
| 301 | TCGCGCCATT | ACTTGCCAAA | AGGGGGCCGC | CGCCGCCAAG | CCTAAGGAAG |
| 351 | ATCCTTATGC | TGGCATGTCC | TTTTGGGATG | TAGATTTAAA | GGACAAGTTT |
| 401 | TCTACTGATT | TG | | | |

Isolate C14 - Seq ID No. 20

| | | | | | |
|---|---|---|---|---|---|
| 1 | TATTTGTTGG | CATAATCAGT | TGTTTGTTAC | TGTAGTGGAC | ACTACCCGCA |
| 51 | GTACTAATTT | AACATTATGT | GCCTCTACAC | AAAATCCTGT | GCCAAATACA |
| 101 | TATGATCCTA | CTAAGTTTAA | GCACTATAGT | AGACATGTGG | AGGAATATGA |
| 151 | TTTACAGTTT | ATTTTTCAGT | TGTGCACTAT | TACTTTAACT | GCAGAGGTTA |
| 201 | TGTCATATAT | CCATAGTATG | AATAGTAGTA | TATTGGAAAA | TTGGAATTTT |
| 251 | GGTGTACCTC | CACCACCTAC | TACAAGTTTA | GTGGATACAT | ATCGTTTTGT |
| 301 | GCAATCCGTT | GCTGTTACCT | GTCAAAAGGA | TACTACACCT | CCAGAAAAGC |
| 351 | AGGATCCATA | TGATAAATTA | AAGTTTTGGA | CTGTTGACCT | AAACCAAAAA |
| 401 | TTTTCCTCCG | ATTTG | | | |

Isolate B6062 - Seq ID No. 273

| | | | | | |
|---|---|---|---|---|---|
| 1 | GAGCTCGCAC | AGGGTCATAA | CAATGGTATC | TGTTGGGGCA | ATCAATTGTT |
| 51 | TGTTACCTGT | GTTGATACCA | CCCGCAGTAC | TAACCTTACC | ATTAGTACAT |
| 101 | TATCTGCAGC | ATCTGCATCC | ACTCCATTTA | AACCATCTGA | TTATAAACAA |
| 151 | TTTATAAGAC | ATGGCGAAGA | ATATGAATTA | CAATTTATAT | TTCAGTTGTG |
| 201 | TAAAATAACA | CTTACAACAG | ATGTTATGGC | TTACATACAT | TTAATGAATG |
| 251 | CCTCCATATT | GGAGGATTGG | AATTTTGGAC | TAACCTTACC | TCCCACTGCT |
| 301 | AGTTTGGAAG | ATGCCTATAG | GTTTATTAAA | AACTCTGCTA | CTACCTGTCA |
| 351 | GCGTAACGCC | CCTCCTGTGC | CAAAGGAAGA | TCCTTTTCAA | AAATTTAAAT |
| 401 | TTTGGGATGT | AGATTTAAAA | GAAAAATTTT | CTATTGATTT | GGATCAGTTT |
| 451 | CCCCTGGCAC | GAAGCTT | | | |

Isolate D3173 - Seq ID No. 274

| | | | | | |
|---|---|---|---|---|---|
| 1 | GAGCTCGCCC | AGGGTCATAA | TAATGGCATC | TGTTGGAACA | ATCAGTTATT |
| 51 | TGTAACTGTT | GTGGATACCA | CCAGGAATAC | AAACATGACA | CTTTCTGCAA |
| 101 | CCACACAGTC | TATGTCCACA | TATAATTCAA | AGCAAATTAA | ACAGTATGTT |
| 151 | AGACATGCAG | AGGAATATGA | ATTACAATTT | GTGTTTCAAC | TATGTAAAAT |
| 201 | ATCCCTGTCT | GCTCAGGTTA | TGGCCTATTT | ACATACTATG | AATTCTACCT |
| 251 | TACTGGAAGA | CTGGAATATA | GGTTTGTCGC | CTCCTGTTGC | CACTAGCTTA |
| 301 | GAGGACAAAT | ACAGATATGT | AAAAAGTGCA | GCTATAACCT | GTCAAAAGGA |
| 351 | TCAGCCCCCT | CCTGAAAAGC | AGGACCCACT | ATCTAAATAT | AAATTTTGGG |
| 401 | AGGTCAATTT | ACAAAACAGT | TTTTCTGCTG | ATTTGGATCA | GTATCCCCTG |
| 451 | GGACGAAGCT | T | | | |

Isolate 7552 - Seq ID No. 275

| | | | | | |
|---|---|---|---|---|---|
| 1 | GAGCTCGCCC | AGGCTCATAA | TAATGGTATT | TGTTGGTTTA | ATGAATTGTT |
| 51 | TGTAACCGTT | GTGGATACCA | CCCGCAGTAC | TAATGTAACC | ATTTGTACTG |
| 101 | CTACATCCCC | CCCTGTATCT | GAATATAAAG | CCACGAGCTT | TAGGGAATAT |
| 151 | TTGCGCCATA | CAGAAGAGTT | TGATTTGCAA | TTCATTTTTC | AGTTATGTAA |
| 201 | AATACATTTA | ACCCCTGAAA | TTATGGCCTA | CCTACATAAT | ATGAATAAAG |
| 251 | CCTTGTTGGA | TGACTGGAAC | CTTGGTGTGG | TACCTCCACC | CTCTACCAGT |
| 301 | CTAGAAGACA | CATATAGGTT | TTTGCAGTCC | AGAGCTATTA | CATGTCAGAA |
| 351 | GGGTGCTGCT | GCCCCGCCGC | CCAAGGAGGA | TCGCTATGCC | AAATTATCAT |
| 401 | TTTGGACTGT | TGATTTACGA | GACAAGTTCT | CCACTGATTT | GGATCAGTAT |
| 451 | CCCTTGGGAC | GAAGCTT | | | |

Isolate JB10 - Seq ID No. 276

| | | | | | |
|---|---|---|---|---|---|
| 1 | GAGCTCGCAC | AGGGACATAA | CAATGGCATT | TGTTGGGGCA | ACCAATTGTT |
| 51 | TGTTACTTGT | GTAGATACTA | CCCGCAGTAC | CAACCTCACT | ATTAGTACTG |
| 101 | TATCTGCACA | ATCTGCATCT | GCCACTTTTA | AACCATCAGA | TTATAAGCAG |
| 151 | TTTATAAGGC | ATGGTGAGGA | ATATGAATTA | CAGTTTATAT | TTCAATTGTG |
| 201 | TAAAATTACT | CTTACCACTG | ATGTAATGGC | CTATATCCAT | ACAATGAATT |
| 251 | CTGCTATTTT | GGAAAATTGG | AATTTTGGCC | TTACCTTGCC | TCCTACTGCT |
| 301 | AGTTTGGAAG | ATGCATATAG | GTTTATTAAA | AATTCAGCTA | CTACATGTCA |
| 351 | ACGCGATGCC | CCTGCACAGC | CCAAGGAGGA | TCCATTTAGT | AAATTAAAAT |
| 401 | TTTGGGACGT | TGATCTTAAA | CAAAAGTTTT | CTATTGATTT | AGATCAGTAT |
| 451 | CCCCTTGGAC | GAAGCTT | | | |

The DNA Sequences of the L1 Amplified Regions of HPV

Isolate Lavc5 - Seq ID No. 277

|     |            |            |            |            |            |
| --- | ---------- | ---------- | ---------- | ---------- | ---------- |
| 1   | GAGCTCGCCC | AGGGTCATAA | TAATGGTCTT | TAAAAGTGAA | AGAGGGAGGC |
| 51  | AGAAGAAGGT | GTGATAGTAT | AGGGATGTAA | AGAAGACTCA | ACCAGCCCTT |
| 101 | GCTGGTTTTG | AAGCTGGAAG | AGGGTCGTGA | GCCAAGGAAT | AAGGGCAGCC |
| 151 | TCTAAAAAGC | TGGAAAAGAT | CAGAAAATGG | TTCTCACCTA | CAGTCTCCAG |
| 201 | AAAGGAACAC | CGTCTGGCCA | ACACCTTGAT | CTTAGCCCAG | TGAGACTCAT |
| 251 | TTCTACCTTC | TGACTTCCAG | AAGTTTAAGG | TAATCAACTT | TTGTTGTTTT |
| 301 | AAGCCACTGA | GTTAATGGCA | ATTTGTTACA | ACAGCCATAG | CAAGCTAGTA |
| 351 | TACCGAGTCT | CATTCTTACC | CTTATCAGAC | CTTCCACAAT | TTCATCCCAT |
| 401 | CCAACCCACC | CAGCAATGTC | TTCTGCTTGG | GTCAGATCAG | TATCCCTTTG |
| 451 | GACGAAGCTT |            |            |            |            |

Isolate D7515 - Seq ID No. 278

|     |            |            |            |            |            |
| --- | ---------- | ---------- | ---------- | ---------- | ---------- |
| 1   | GAGCTCGCAC | AGGGACATAA | TAATGGTATA | TGCTGGGGTA | ATCAACTATT |
| 51  | TGTTACTGTT | GTAGACACTA | CACGTAGTAC | CAACATGACT | TTATGTTCTG |
| 101 | AGGAAAAATC | AGAGGCTACA | TACAAAAATG | AAAACTTTAA | GGAATACCTT |
| 151 | AGACATGTGG | AAGGATATGA | TTTGCAGTTT | ATATTTCAGC | TGTGCAAAAT |
| 201 | ATCCCTTACT | GCAAATGTTA | TGCAATACAT | ACACACCATG | AATCCAGATA |
| 251 | TATTAGAGGA | CTGGCAATTT | GGCCTTACAC | CACCTCCTTC | AGGTAATTTA |
| 301 | CAGGACACAT | ATAGATTTGT | TACCTCGCAG | GCTATTACCT | GTCAAAAAAC |
| 351 | ATCCCCTCCA | ACAGCAAAGG | AACATCCTCT | TAAAAAGTAC | AGTTTTTGGG |
| 401 | AAATCAATTT | AAAGGAAAAA | TTTTCTGCAG | ATTTAGATCA | GTATCCCCTT |
| 451 | GGACGAAGCT | T          |            |            |            |

Isolate Pap116 - Seq ID No. 279

|     |            |            |            |            |            |
| --- | ---------- | ---------- | ---------- | ---------- | ---------- |
| 1   | ACACTACACG | TAGTACTAAT | TTACATTGTC | TGCCTGCACC | GAAACAGCCG |
| 51  | TACCTGCTGT | ATATAGCCCT | ACAAAGTTTA | AGGAATATAC | TAGGCATGTG |
| 101 | GAGGAATATG | ATTTACAATT | TATATTTCAA | TTGTGTACTA | TCACATTAAC |
| 151 | TGCAGACGTT | ATGGCCTACA | TCCATACTAT | GAATCCTACA | ATTTTGGACA |
| 201 | ATTGGAATAT | AGGCGTTACC | CCTCCACCAT | CTGCAAGCTG | AGCTTGGTGG |
| 251 | ACACGTATAG | GTATTTACAA | TCAGCAGCAT | AGCATGTCAG | AAGGATGCTC |
| 301 | CTGCACCTGA | AAAAAAGGGT | CCCTATGACG | ATTTAAAATT | TTGGAATGTT |
| 351 | GATTTAAAGG | AAAAGTTTAG | TAACAGAACT | AGATCAGTAT | CCCC       |

Isolate W13b - Seq ID No. 280

|     |            |            |            |            |            |
| --- | ---------- | ---------- | ---------- | ---------- | ---------- |
| 1   | GAGCTCGCAC | AGGGACATAA | TAATGGCATT | TCGTGGAATA | ATCACGTTTT |
| 51  | TATTACTTGT | GTTGACACTC | ATAGAATGAC | CAATTTAACC | ATTACGACTC |
| 101 | GTGTTACTCA | ATCTGTTGCA | CAAACATTTA | CTCCAGCAAA | CTTTAAGCAA |
| 151 | TACATTAGGC | ATGGGGAAGA | ATATGAATTG | CAATTTATAT | TTCAATTGTG |
| 201 | TAAAATCACT | TTAACTACTG | AAATTATGGC | TTACCTGCAC | ACCATGGATT |
| 251 | CTACAATTTT | AGAACAGTGG | AATTTTGGAT | TAACCTTGCC | CCCCTCAGCT |
| 301 | AGTTTGGAGG | AGTCCTATGC | ATTTGTAAAA | AATGCACCAA | CATCCTGTCA |
| 351 | CAAGGACAGT | CCTCCACAGG | CTAAACAAGA | CCCTTTGGCA | AAATATAAAT |
| 401 | TTTGGAATGT | AGACCTTAAG | GAACGCTTTT | CTTTGGATTT | GGATCAGTTT |
| 451 | CCTTTTGGAC | GAAGCTT    |            |            |            |

Isolate Lavb24a - Seq ID No. 281

|     |            |            |            |            |            |
| --- | ---------- | ---------- | ---------- | ---------- | ---------- |
| 1   | GAGCTCGCAC | AGGGGTCATA | ATAATGGCAT | ATGCTGGGGT | AATCAGGTAT |
| 51  | TTGTTACTGT | TGTGGATACT | ACCAGAAGCA | CCAACATGAC | TATTAATGCA |
| 101 | GCTAAAAGCA | CATTAACTAA | ATATGATGCC | CGTGAAATCA | ATCAATACCT |
| 151 | TCGCCATGTG | GAGGAATATG | AACTACAGTT | TGTGTTTCAA | CTTTGTAAAA |
| 201 | TAACCTTAAC | TGCAGAAGTT | ATGGCATATT | TGCATAATAT | CAATAATACT |
| 251 | TTATTAGACG | ATTGGAATAT | TGGATTATCC | CCACCAGTTG | CAACTAGCTT |
| 301 | AGAGGATAAA | TATAGGTATA | TTAAAGCAC  | AGCTATTACA | TGTCAGAGGG |
| 351 | AACAGCCCCC | TGCAGAAAAG | CAGGATCCCC | TGGCTAAATA | TAAGTTTTGG |
| 401 | GAAGTTAATT | TACAGAACAG | CTTTTCTGCA | GACCTGGATC | AGTTTCCTTT |
| 451 | TGGACCAAGC | TT         |            |            |            |

Isolates Lavb24b and PAP291 - Seq ID No. 282

|     |            |            |            |            |            |
| --- | ---------- | ---------- | ---------- | ---------- | ---------- |
| 1   | GAGCTCGCCC | AGGGACATAA | TAATGGCATT | TGTTGGTTTA | ATGAGTTATT |
| 51  | TGTTACAGTT | GTAGATACTA | CCCGCAGTAC | CAATATTACT | ATTTCAGCTG |
| 101 | CTGCTACACA | GGCTAATGAA | TACACAGCCT | CTAACTTTAA | GGAATACCTC |
| 151 | CGCCACACCG | AGGAATATGA | CTTACAGGTT | ATATTGCAAC | TTTGCAAAAT |
| 201 | ACATCTTACC | CCTGAAATTA | TGGCATACCT | ACATAGTATG | AATGAACATT |
| 251 | TATTGGATGA | GTGGAATTTT | GGCGTGTTAC | CACCTCCTTC | CACCAGCCTT |
| 301 | GATGATACCT | ATCGCTATCT | GCAGTCCCGT | GCTATTACCT | GCCAAAAGGG |
| 351 | TCCTTCCGCC | CCTGCCCCTA | AAAAGGATCC | TTATGATGGC | CTTGTATTTT |
| 401 | GGGAGGTTGA | TTTAAAGGAC | AAACTATCCA | CAGATTTGGA | TCAGTATCCT |
| 451 | TTGGGACGAA | GCTT       |            |            |            |

Isolate B8988 - Seq ID no. 283

|     |            |            |            |            |            |
| --- | ---------- | ---------- | ---------- | ---------- | ---------- |
| 1   | GAGCTCGCAC | AGGGTCATAA | TAATGGTATT | TGTTGGCATA | ATCAATTATT |
| 51  | TCTTACTGTT | GTGGATACCA | CTCGCAGTAC | CAATTTTACT | TTGTCTACTA |
| 101 | CTACTGAATC | AGCTGTACCA | AATATTTATG | ATCCTAATAA | ATTTAAGGAA |
| 151 | TATATTAGGC | ATGTTGAGGA | ATATGATTTG | CAATTTATAT | TCAGTTGTG  |
| 201 | TACTATAACA | TTGTCAACTG | ATGTAATGTC | CTATATACAT | ACTATGAATC |
| 251 | CTGCTATTTT | GGATGATTGG | AATTTTGGTG | TTGCCCCTCC | ACCATCTGCT |

| The DNA Sequences of the L1 Amplified Regions of HPV | | | | | |
|---|---|---|---|---|---|
| 301 | AGTCTTGTAG | ATACATACCG | CTATCTGCAA | TCAGCAGCAA | TTACATGTCA |
| 351 | AAAAGACGCC | CCTGCACCTA | CTAAAAAGGA | TCCATATGAT | GGCTTAAACT |
| 401 | TTTGGAATGT | AAATTTAAAA | CAAAAGTTTA | GTTCTCAACT | GGATCAGTTT |
| 451 | CCCCTTGGAC | GAAGCTT | | | |
| | | HPV35 (SEQ ID NO: 284) | | | |
| 1 | CAACGTGCAC | AAGGCCATAA | TAATGGTATT | TGTTGGAGTA | ACCAATTGTT |
| 51 | TGTTACTGTA | GTTGATACAA | CCCGTAGTAC | AAATATGTCT | GTGTGTTCTG |
| 101 | CTGTGTCTTC | TAGTGACAGT | ACATATAAAA | ATGACAATTT | TAAGGAATAT |
| 151 | TTAAGGCATG | GTGAAGAATA | TGATTTACAG | TTTATTTTTC | AGTTATGTAA |
| 201 | AATAACACTA | ACAGCAGATG | TTATGACATA | TATTCATAGT | ATGAACCCGT |
| 251 | CCATTTTAGA | GGATTGGAAT | TTTGGCCTTA | CACCACCGCC | TTCTGGTACC |
| 301 | TTAGAGGACA | CATATCGCTA | TGTAACATCA | CAGGCTGTAA | CTTGTCAAAA |
| 351 | ACCCAGTGCA | CCAAAACCTA | AAGATGATCC | ATTAAAAAAT | TATACTTTTT |
| 401 | GGGAGGTTGA | TTTAAAGGAA | AAGTTTTCTC | CAGACTTAGA | TCAATTTCCG |
| 451 | TTGGGCCGTA | AATT | | | |
| | | HPV39 (SEQ ID NO: 285) | | | |
| 1 | CAGCTCGCCC | AGGGtCATAA | TAATGGTATA | TGTTGGCATA | ATCAATTATT |
| 51 | TCTTACTGTT | GTGgACACTA | CCCGTAGTAC | CaACTTTACA | TTATCTACCT |
| 101 | CTATAGAGTC | TTCCATACCT | TCTACATATG | ATCCTTCTAA | GTTtAAGGAA |
| 151 | TATACCAGGC | ACGTGGAGGA | GTATGATTTA | CAATTTATAT | tTCAACTGTG |
| 201 | TACTGTCACA | TTAACAACTG | ATGTTATGTC | TTATATTCAC | ACTATGAATT |
| 251 | CCTCTATATT | GGaCAAATGG | AATTTTGCTT | TAGCTCCTCC | ACCATCtGCC |
| 301 | AGTTTGGTAG | ACACTTACAG | ATACCTACAG | TCTGCACCCA | TTACATGTCA |
| 351 | AAAGGATGCT | CCAGCACCTG | AAAAGAAAGA | TCCATATGAC | GGTCTAAAGT |
| 401 | TTTGGAATGT | TGACTTAAGG | GAAAAGTTTA | GTTTGGAACT | TGATCAGTAT |
| 451 | CCctTgGGAC | GAAGCTT | | | |
| | | HPV40 (SEQ ID NO: 286) | | | |
| 1 | CAAAAGGCCC | AGGGCCATAA | CAATGGCATA | TGTTTTGGCA | ATCAGTTATT |
| 51 | TGTTACAGTT | GTAGACACCA | CTCGTAGCAC | TAATTTGACC | TTATGTGCTG |
| 101 | CCACACAGGG | CCCCACACCA | GGCCCATATA | ATAACAGTAA | TTTCAAGGAA |
| 151 | TATTTGCGTC | AGGGGGAGGA | GTTTGATTTG | CAGTTTATTT | TTCAGTTATG |
| 201 | TGTAATTACC | TTAAATGCAG | AGGTTATGAC | ATATATTCAT | GCAATGGATC |
| 251 | CTACGTTGTT | GGAGGATTGG | AACTTTAAAA | TTGCTCCTCC | AGCCTCTGCA |
| 301 | TCCTTAGAGG | ATACATATAG | GTTCCTTACC | AACAAGGCTA | TTGCCTGTCA |
| 351 | GCGCGATGCC | GCCCCCAAGG | TACGGAGGA | TCCATATAAA | AAATATAAAT |
| 401 | TTTGGGATGT | CAATTTAACA | GAAAGATTTT | CTTCCCAATT | AGATCAATTT |
| 451 | CCATTAGGAC | GTAAGTT | | | |
| | | HPV42 (SEQ ID NO: 287) | | | |
| 1 | GAGCTCGCAC | AGGGTCATAA | TAATGGTATA | TGTTGGGAA | ATCAGCTATT |
| 51 | TTTAACTGTG | GTTGATACTA | CCCGTAGTAC | TAACATGACT | TTGTGTGCCA |
| 101 | CTGCAACATC | TGGTGATACA | TATACAGCTG | CTAATTTTAA | GGAATATTTA |
| 151 | AGACATGCTG | AAGAATATGA | TGTGCAATTT | ATATTTCAAT | TGTGTAAAAT |
| 201 | AACATTAACT | GTTGAAGTTA | TGTCATATAT | ACACAATATG | AATCCTAACA |
| 251 | TATTAGAGGA | GTGGAATGTT | GGTGTTGCAC | CACCACCTTC | AGGAACTTTA |
| 301 | GAAGATAGTT | ATAGGTATGT | ACAATCAGAA | GCTATTCGCT | GTCAGGCTAA |
| 351 | GGTAACAACG | CCAGAAAAAA | AGGATCCTTA | TTCAGACTTT | TCCTTTTGGG |
| 401 | AGGTAAATTT | ATCTGAAAAG | TTTTCTACTG | ATTTAGATCA | GTATCCTCTG |
| 451 | GGACGAAGCT | T | | | |
| | | HPV45 (SEQ ID NO: 288) | | | |
| 1 | GAGCTCGCAC | AGGGTCATAA | CAATGGTATT | TGTTGGCATA | ATCAGTTGTT |
| 51 | TGTTGCTGTA | GTGGACACTA | CCCGCAGTAC | TAATTTAACA | TTATGTGCCT |
| 101 | CTACACAAAA | TCCTGTGCCA | AGTACATATG | ACCCTACTAA | GTTTAAGCAG |
| 151 | TATAGTAGAC | ATGTGGAGGA | ATATGATTTA | CAGTTTATTT | TTCAGTTGTG |
| 201 | CACTATTACT | TTAACTGCAG | AGGTTATGTC | ATATATCCAT | AGTATGAATA |
| 251 | GTAGTATATT | AGAAAATTGG | AATTTTGGTG | TCCCTCCACC | ACCTACTACA |
| 301 | AGTTTGGTGG | ATACATATCG | TTTTGTGCAA | TCAGTTGCTG | TTACCTGTCA |
| 351 | AAAGGATACT | ACACCTCCAG | AAAAGCAGGA | TCCATATGAT | AAATTAAAGT |
| 401 | TTTGGACTGT | TGACCTAAAG | GAAAAATTTT | CCTCCGATTT | GAATCAGTAT |
| 451 | CCCTTGGGAC | GAAGCTT | | | |
| | | HPV51 (SEQ ID NO: 289) | | | |
| 1 | TCCACCGTGC | GCAGGGTCAC | AATAATGGCA | TTTGCTGGAA | CAATCAGCTT |
| 51 | TTTATTACCT | GTGTTGATAC | TACCAGAAGT | ACAAATTTAA | CTATTAGCAC |
| 101 | TGCCACTGCT | GCGGTTTCCC | CAACATTTAC | TCCAAGTAAC | TTTAAGCAAT |
| 151 | ATATTAGGCA | TGGGGAAGAG | TATGAATTGC | AATTTATTT | TCAATTATGT |
| 201 | AAAATTACTT | TAACTACAGA | GGTAATGGCT | TATTTACACA | CAATGGATCC |
| 251 | TACCATTCTT | GAACAGTGGA | ATTTTGGATT | AACATTACCT | CCGTCTGCTA |
| 301 | GTTTGGAGGA | TGCATATAGG | TTTGTTAGAA | ATGCAGCTAC | TAGCTCTCAA |
| 351 | AAGGACACCC | CTCCACAGGC | TAAGCCAGAT | CCTTTGGCCA | AATATAAATT |
| 401 | TTGGGATGTT | GATTTAAAGG | AACGATTTTC | TTTAGATTTA | GACCAATTT |

The DNA Sequences of the L1 Amplified Regions of HPV

HPV52 (SEQ ID NO: 290)

| | | | | | |
|---|---|---|---|---|---|
| 1 | GAGCTCGCCC | AGGGTCATAA | TAATGGCATA | TGTTGGGGCA | ATCAGTTGTT |
| 51 | TGTCACAGTT | GTGGATACCA | CTCGTAGCAC | TAACATGACT | TTATGTGCTG |
| 101 | AGGTTAGAAA | CGAAAGCACA | TATAAAAATG | AAAATTTTAA | GGAATACCTT |
| 151 | CGTCATGGCG | AGGAATTTGA | TTTACAATTT | ATTTTTCAAT | TGTGCAAAAT |
| 201 | TACATTAACA | GCTGATGTTA | TGACATACAT | TCATAAGATG | GATGCCACTA |
| 251 | TTTTAGAGGA | CTGGCAATTT | GGCCTTACCC | CACCACCGTC | TGCATCTTTG |
| 301 | GAGGACACAT | ACAGATTTGT | CACTTCTACT | GCTATAACTT | GTCAAAAAAA |
| 351 | CACACCACCT | AAAGGAAAGG | AAGATCCTTT | AAAGGACTAT | ATGTTTTGGG |
| 401 | AGGTGGATTT | AAAAGAAAAG | TTTTCTGCAG | ATTTAAATCA | GTATCCTTTT |
| 451 | GGACCAAGCT | T | | | |

HPV53 (SEQ ID NO: 291)

| | | | | | |
|---|---|---|---|---|---|
| 1 | GAGCTCGCCC | AGGGTCATAA | TAATGGCATC | TGTTGGAACA | ATCAGTTATT |
| 51 | TGTAACTGTT | GTGGATACCA | CCAGGAATAC | AAACATGACT | CTTTCCGCAA |
| 101 | CCACACAGTC | TATGTCTACA | TATAATTCAA | AGCAAATTAA | ACAGTATGTT |
| 151 | AGACATGCAG | AGGAATATGA | ATTACAATTT | GTGTTTCAAC | TATGTAAAAT |
| 201 | ATCCCTGTCT | GCTGAGGTTA | TGGCCTATTT | ACATACTATG | AATTCTACCT |
| 251 | TACTGGAAGA | CTGGAATACA | GGTTTGTCGC | CTCCTGTTGC | CACTAGCTTA |
| 301 | GAGGACAAAT | ACAGATATGT | GAAAAGTGCA | GCTATAACCT | GTCAAAAGGA |
| 351 | TCAGCCCCCT | CCTGAAAAGC | AGGACCCACT | ATCTAAATAT | AAATTTTGGG |
| 401 | AGGTCAATTT | GCAAAACAGT | TTTTCTGCTG | ATTTGGATCA | GTATCCCCTG |
| 451 | GGACGAAGCT | T | | | |

HPV54 (SEQ ID NO: 292)

| | | | | | |
|---|---|---|---|---|---|
| 1 | GAGCTCGCAC | AGGGTCATAA | TAATGGTATT | TGTTGGGGCA | ATCAATTGTT |
| 51 | TTTAACAGTT | GTAGATACCA | CCCGTAGTAC | TAACCTAACA | TTGTGTGCTA |
| 101 | CAGCATCCAC | GCAGGATAGC | TTTAATAATT | CTGACTTTAG | GGAGTATATT |
| 151 | AGACATGTGG | AGGAATATGA | TTTACAGTTT | ACATTTCAGT | TATGTACCAT |
| 201 | AGCCCTTACA | GCAGATGTTA | TGGCCTATAT | TCATGGAATG | AATCCCACTA |
| 251 | TTCTAGAGGA | CTGGAACTTT | GGTATAACCC | CCCCAGCTAC | AAGTAGTTTG |
| 301 | GAGGACACAT | ATAGGTTTGT | ACAGTCACAG | GCCATTGCAT | GTCAAAAGAA |
| 351 | TAATGCCCCT | GCAAAGGAAA | AGGAGGATCC | TTACAGTAAA | TTTACTTTTT |
| 401 | GGACTGTTGA | CCTTAAGGAA | CGATTTTCAT | CTGACCTTGA | TCAGTATCCC |
| 451 | CTTGGACGAA | GCTT | | | |

HPV55 (SEQ ID NO: 293)

| | | | | | |
|---|---|---|---|---|---|
| 1 | GCGCAGGGCC | ACAATAATGG | TATTTGTTGG | GGGAATCAGT | TATTTGTTAC |
| 51 | TGTTGTAGAT | ACTACACGTA | GTACAAACAT | GACAATATGT | GCTGCTACAA |
| 101 | CTCAGTCTCC | ATCTACAACA | TATAATAGTA | CAGAATATAA | ACAATACATG |
| 151 | CGACATGTTG | AGGAGTTTGA | CTTACAGTTT | ATGTTTCAAT | TATGTAGTAT |
| 201 | TACCTTAACT | GCTGAGGTAA | TGGCCTATTT | ACATACCATG | AATCCTGGTA |
| 251 | TTTTGGAACA | GTGGAACTTT | GGGTTGTCGC | CACCCCCAAA | TGGTACCTTA |
| 301 | GAAGACAAAT | ACAGATATGT | GCAGTCACAG | GCCATTACAT | GTCAAAAGCC |
| 351 | TCCCCCTGAA | AAGCAAAGC | AGGACCCCTA | TGCAAAATTA | AGTTTTTGGG |
| 401 | AGGTAGATCT | CAGAGAAAAG | TTTTCTAGTG | AGTTAGATCA | ATATCCCCTT |
| 451 | GGTAG | | | | |

HPV56 (SEQ ID NO: 294)

| | | | | | |
|---|---|---|---|---|---|
| 1 | GAGCTCGCAC | AGGGACATAA | TAATGGCATT | TGCTGGGGTA | ATCAATTATT |
| 51 | TGTGACTGTA | GTAGATACTA | CTAGAAGTAC | TAACATGACT | ATTAGTACTG |
| 101 | CTACAGAACA | GTTAAGTAAA | TATGATGCAC | GAAAAATTAA | TCAGTACCTT |
| 151 | AGACATGTGG | AGGAATATGA | ATTACAATTT | GTTTTTCAAT | TATGCAAAAT |
| 201 | TACTTTGTCT | GCAGAGGTTA | TGGCATATTT | ACATAATATG | AATGCTAACC |
| 251 | TACTGGAGGA | CTGGAATATT | GGGTTATCCC | CGCCAGTGGC | CACCAGCACC |
| 301 | GAAGATAAAT | ATAGATATGT | TAGAAGCACA | GCTATAACAT | GTCAACGGGA |
| 351 | ACAGCCACCA | ACAGAAAAAC | AGGACCCATT | AGCTAAATAT | AAATTTTGGG |
| 401 | ATGTTAACTT | ACAGGACAGT | TTTTCTACAG | ACCTGGATCA | GTATCCCTTG |
| 451 | GGACGAAGCT | T | | | |

HPV57 (SEQ ID NO: 295)

| | | | | | |
|---|---|---|---|---|---|
| 1 | GCCCAGGGAC | ATAACAATGG | CATGTGCTGG | GGCAATCGGA | TCTTCCTAAC |
| 51 | AGTGGTGGAC | ACCACGCGCA | GCACAAATGT | CTCTTTGTGT | GCCACTGTAA |
| 101 | CCACAGAAAC | TAATTATAAA | GCCTCCAATT | ATAAGGAATA | CCTTAGGCAT |
| 151 | ATGGAGGAAT | ATGATTTGCA | GTTCATTTTT | CAACTGTGCA | AAATAACACT |
| 201 | CACCCCCGAG | ATAATGGCAT | ACATACATAA | CATGGATGCG | CGGTTGCTAG |
| 251 | AGGACTGGAA | CTTTGGTGTC | CCCCCACCCC | CGTCCGCCAG | CCTGCAGGAC |
| 301 | ACCTACAGGT | ATTTGCAATC | CCAAGCGATA | ACATGTCAGA | AGCCCACACC |
| 351 | CCCTAAGACC | CCTACTGATC | CCTATGCAAC | CATGACATTC | TGGGATGTGG |
| 401 | ATCTCAGTGA | AAGTTTTTCC | ATGGATCTGG | ACCAATTCCC | CCTGGGACG |

HPV59 (SEQ ID NO: 296)

| | | | | | |
|---|---|---|---|---|---|
| 1 | CACAAGGCTC | AGGGTTTAAA | CAATGGTATA | TGTTGGCACA | ATCAATTGTT |
| 51 | TTTAACAGTT | GTAGATACTA | CTCGCAGCAC | CAATCTTTCT | GTGTGTGCTC |
| 101 | TACTACTCTC | TATTCCTAAT | GTATACACAC | CTACCAGTTT | TAAAGAATAT |
| 151 | GCCAGACATG | TGGAGGAATT | TGATTTGCAG | TTTATATTTC | AACTGTGTAA |
| 201 | AATAACATTA | ACTACAGAGG | TAATGTCATA | CATTCATAAT | ATGAATACCA |

-continued

The DNA Sequences of the L1 Amplified Regions of HPV

| 251 | CTATTTTGGA | GGATTGGAAT | TTTGGTGTTA | CACCACCTCC | TACTGCTAGT |
| 301 | TTAGTTGACA | CATACCGTTT | TGTTCAATCT | GCTGCTGTAA | CTTGTCAAAA |
| 351 | GGACACCGCA | CCGCCAGTTA | AACAGGACCC | TTATGACAAA | CTAAAGTTTT |
| 401 | GGCCTGTAGA | TCTTAAGGAA | AGGTTTTCTG | CAGATCTTGA | TCAGTTTCCT |
| 451 | TTGGGACGTA | AATT | | | |

Isolate 36A is an HPV59 variant, and isolate 36B is an HPV42 variant. Isolate 238B corresponds to the HPV31 type described in the literature. A cervical carcinoma isolate, C14, is a variant of HPV45. Isolate B6062 is an HPV26, isolate D3173 is an HPV53 variant, and isolate B8988 is an HPV68.

Those skilled in the art will recognize that with the above sequence information, primers and probes for amplifying and detecting these new HPV isolates can be obtained. In addition, these sequences enable one to isolate the entire virus from samples containing the virus. The discovery of these new HPV isolates led to the creation of additional L1 consensus oligonucleotide probes for use in conjunction with FS10 (Seq ID No. 21), MY18 (Seq ID No. 106), and MY19 (Seq ID No. 271). These L1 consensus probes are depicted below under the FS10 (Seq ID No. 21) probe sequence to demonstrate the similarity to the FS 10 (Seq ID No. 21) sequence. L 1 consensus probe WD 147 (Seq ID No. 27) will hybridize to HPV45 DNA. MY46 (Seq ID No. 28) is a combination of FS10 (Seq ID No. 21) and MY19 (Seq ID No. 271). In one embodiment, a consensus L1 probe can be an equimolar mixture of MY18 (Seq ID No. 106), MY46 (Seq ID No. 28), MY57 (Seq ID No. 26), and WD147 (Seq ID No. 27).

| | Seq ID No. | Sequence |
|---|---|---|
| FS10 | 21 | 5' C T G T G G T A G A T A C C A C A C G C A G T A C |
| MY66 | 22 | — A — — T — — — — — — — T — — T — — — — — — C — — |
| MY55 | 23 | — — — — — T — — — — — — T — — C — — T — — — — — — |
| MY39 | 24 | — — — — T — — G — — — — T — — C A — A — — C — — |
| MY56 | 25 | — — — — T — — — — — — — T — — T A — A — — C — — |
| MY57 | 26 | — — — — — — — — — — — — — — — — — — T — — — — — — |
| WD147 | 27 | — — — — — A — — G — — C — — T — — C — — — — — — — |
| MY46 | 28 | — — — — — — — — — — — — — — — — W — — — — — — — — |

Example 4, below, describes the creation of an alternate long generic probe with enhanced detection capabilities. In particular, the long generic probe described in Example 4 has the ability to detect HPV51.

The present invention provides a number of probes for typing amplified DNA produced from L1 consensus primers. While most probes for typing HPV hybridize to known HPV types, others specifically detect previously uncharacterized HPV types and hybridize to novel HPVs identified in clinical samples as a result of use of the present methods. These type-specific probes are depicted below in Tables 5 and 5a.

TABLE 5

HPV Typing Probes For Use with L1 Consensus Primers

| Probe | Sequence ID No. | Specificity | Sense | Sequence | Genome Position | 5' Biotinylated Versions |
|---|---|---|---|---|---|---|
| MY12 | 142 | HPV6 | + | CATCCGTAACTACATCTTCCA | 6813 | MY134 |
| MY62 | 143 | HPV6 | + | CTCCTGAAAAGGAAAAGCCA | 7068 | |
| MY63 | 144 | HPV6 | − | TGGCTTTTCCTTTTCAGGAG | 7068 | MY135 |
| MY125 | 145 | HPV6/HPV11 | + | ACAATGAATCCYTCTGTTTTGG | 6950/6935 | MY138 |
| MY126 | 146 | HPV6/HPV11 | + | ATCGCCTCCMCCAAATG | 6991/6976 | |
| MY13 | 147 | HPV11 | + | TCTGTGTCTAAATCTGCTACA | 6800 | MY136 |
| MY61 | 148 | HPV11 | + | CACACCTGAAAAAGAAAAACAG | 7051 | |

TABLE 5-continued

HPV Typing Probes For Use with L1 Consensus Primers

| Probe | Sequence ID No. | Specificity | Sense | Sequence | Genome Position | 5' Biotinylated Versions |
|---|---|---|---|---|---|---|
| MY65 | 149 | HPV11 | − | CTGTTTTTCTTTTTCAGGTGTG | 7051 | MY137 |
| WD150 | 150 | HPV11 | + | CAGAAACCCACACCTGAAAAAGA | 7059 | |
| WD151 | 151 | HPV11 | + | AGAAACCCACACCTGAAAAAGAA | 7058 | |
| MY14 | 152 | HPV16 | + | CATACACCTCCAGCACCTAA | 6926 | MY14 |
| MY58 | 153 | HPV16 | + | TTGTAACCCAGGCAATTGCT | 6895 | |
| MY71 | 154 | HPV16 | + | ACATACACCTCCAGCACCTA | 6923 | |
| MY72 | 155 | HPV16 | + | CATACACCTCCAGCACCTA | 6924 | |
| MY95 | 156 | HPV16 | − | GATATGGCAGCACATAATGAC | 6685 | MY139 |
| MY96 | 157 | HPV16 | − | AGTTTCTGAAGTAGATATGGCA | 6674 | |
| MY97 | 158 | HPV16 | − | CTGAAGTAGATATGGCAGCAC | 6670 | |
| MY133 | 159 | HPV16 | + | GTAACATCCCAGGCAATTG | 6897 | MY140 |
| WD152 | 160 | HPV16 | + | TTTGTAACCCAGGCAATTGCT | 6894 | |
| WD153 | 161 | HPV16 | + | GTTTGTAACCCAGGCAATTGCT | 6893 | |
| MY60 | 162 | HPV18 | + | CAGTCTCCTGTACCTGGG | 6657 | |
| MY73 | 163 | HPV18 | + | GATGCTGCACCGGCTGAA | 6906 | |
| MY107 | 164 | HPV18 | − | GCCCAGGTACAGGAGAC | 6659 | |
| MY130 | 165 | HPV18 | + | GGGCAATATGATGCTACCAAT | 6672 | MY142 |
| MY131 | 166 | HPV18 | + | GTACCTGGGCAATATGATG | 6666 | |
| MY132 | 167 | HPV18 | + | TCTCCTGTACCTGGGCAA | 6660 | |
| WD74 | 168 | HPV18 | + | GGATGCTGCACCGGCTGA | 6905 | MY141 |
| WD75 | 169 | HPV18 | − | TCAGCCGGTGCAGCATCC | 6905 | |
| WD126 | 170 | HPV31 | + | CCAAAAGCCCAAGGAAGATC | 6851 | |
| WD127 | 171 | HPV31 | + | CAAAAGCCCAAGGAAGATC | 6852 | |
| WD128 | 172 | HPV31 | + | TTGCAAACAGTGATACTACATT | 6597 | MY143 |
| MY109 | 173 | HPV31 | − | GAGGGAGGTGTGGTCAAT | 6769 | |
| MY110 | 174 | HPV31/HPV31B | − | AAGAACCTGAGGGAGGT | 6778 | |
| MY92 | 175 | HPV31/HPV31B | + | CCAAAAGCCYAAGGAAGATC | 6853 | MY144 |
| MY127 | 176 | HPV31/HPV31B | + | ACCACACCTCCCTCAG | 6773 | |
| MY128 | 177 | HPV31/HPV31B | + | ACAGGCCATTACATGTCAA | 6823 | |
| MY16 | 178 | HPV33 | + | CACACAAGTAACTAGTGACAG | 6628 | MY145 |
| MY59 | 179 | HPV33 | + | AAAAACAGTACCTCCAAAGGA | 6877 | |
| MY64 | 180 | HPV33 | − | TCCTTTGGAGGTACTGTTTTT | 6877 | MY146 |
| MY115 | 181 | HPV35 | + | CTGCTGTGTCTTCTAGTGACAG | | |
| MY116 | 182 | HPV35 | + | TGCACCAAAACCTAAAGATG | | |
| MY117 | 183 | HPV35 | − | ATCATCTTTAGGTTTTGGTGC | | |
| MY89 | 184 | HPV39 | + | TAGAGTCTTCCATACCTTCTAC | | MY147 |
| MY90 | 185 | HPV39 | + | CTGTAGCTCCTCCACCATCT | | MY148 |
| MY91 | 186 | HPV39 | + | AGACACTTACAGATACCTACAG | | |
| MY118 | 187 | HPV40 | + | CACACCAGGCCCATATAAT | | |
| MY119 | 188 | HPV40 | + | CCAAGGTACGGGAGGATC | | |
| MY120 | 189 | HPV40 | − | GATCCTCCCGTACCTTG | | |
| MY121 | 190 | HPV42 | + | CACTGCAACATCTGGTGAT | | |
| MY122 | 191 | HPV42 | − | TCACCAGATGTTGCAGTG | | |
| MY33 | 192 | HPV42 | − | GGCGTTGTTACCTTAGCC | | |
| MY34 | 193 | HPV42 | + | GGCTAAGGTAACAACGCC | | |
| MY68 | 194 | HPV45 | + | GGATACTACACCTCCAG | | |
| MY69 | 195 | HPV45 | + | ATACTACACCTCCAGAAAAGC | | MY149 |
| MY70 | 196 | HPV45 | + | TAGTGGACACTACCCGCAG | | |
| MY98 | 197 | HPV45 | − | GCACAGGATTTTGTGTAGAGG | | |
| MY99 | 198 | HPV45 | − | TGTATTTGGCACAGGATTTTG | | |
| MY100 | 199 | HPV45 | − | CAGGATTTTGTGTAGAGGCA | | |
| MY108 | 200 | HPV45 | + | CAAATCCTGTGCCAGGTAC | | |
| MY129 | 201 | HPV45 | − | GCACAGGATTTTGTGTAGAG | | MY150 |
| MY87 | 202 | HPV51 | + | TATTAGCACTGCCACTGCTG | | |
| MY88 | 203 | HPV51 | + | CCCAACATTTACTCCAAGTAAC | | |
| MY80 | 204 | HPV52 | + | CTGAGGTTAGAAAGGAAAGCA | | |
| MY81 | 205 | HPV52 | + | CACTTCTACTGCTATAACTTGT | | |
| MY82 | 206 | HPV52 | + | ACACACCACCTAAAGGAAAGG | | |
| MY101 | 207 | HPV53 | + | CGCAACCACACAGTCTATGT | | |
| MY102 | 208 | HPV53 | + | TTCTACCTTACTGGAAGACTGG | | |
| MY103 | 209 | HPV53 | + | GGAGGTCAATTTGCAAAAC | | |
| MY111 | 210 | HPV54 | − | TGCAGGGGCATTATTCTTT | | |
| MY112 | 211 | HPV54 | + | TACAGCATCCACGCAG | | |
| MY113 | 212 | HPV54 | + | CACGCAGGATAGCTT | | |
| MY114 | 213 | HPV54 | + | CCACGCAGGATAGCTT | | |
| MY151 | 214 | HPV55 | + | GTGCTGCTACAACTCAGTCT | | |
| MY152 | 215 | HPV55 | + | GCTACAACTCAGTCTCCATC | | |
| MY153 | 216 | HPV55 | − | TGCCTTTTCAGGGGGAG | | |
| MY154 | 217 | HPV57 | + | AATGTCTCTTTGTGTGCCAC | | |
| MY155 | 218 | HPV57 | + | GTGTGCCACTGTAACCACA | | |
| MY156 | 219 | HPV57 | − | GGATCAGTAGGGGTCTTAGG | | |
| MY93 | 220 | HPV58 | + | GCACTGAAGTAACTAAGGAAGG | | |
| MY94 | 221 | HPV58 | + | AGCACCCCTAAAGAAAAGGA | | |
| MY123 | 222 | HPV59 | + | GCCAGTTAAACAGGACCC | | |

TABLE 5-continued

HPV Typing Probes For Use with L1 Consensus Primers

| Probe | Sequence ID No. | Specificity | Sense | Sequence | Genome Position | 5' Biotinylated Versions |
|---|---|---|---|---|---|---|
| MY124 | 223 | HPV59 | − | CATAAGGGTCCTGTTTAACTG | | |
| MY83 | 224 | PAP88 | + | ATTAATGCAGCTAAAAGCACATT | | |
| MY84 | 225 | PAP88 | + | GATGCCCGTGAAATCAATCAA | | |
| MY86 | 226 | PAP155 | + | TACTTGCAGTCTCGCGCCA | | |
| MY85 | 227 | PAP155 | + | CCAACACCGAATCAGAATATAAA | | |
| MY104 | 228 | PAP238A | + | GTAGGTACACAGGCTAGTAGCTC | | |
| MY105 | 229 | PAP238A | + | GCTCTACTACAACGTATGCCA | | |
| MY106 | 230 | PAP238A | + | AGTTGCCAACGTCCTCAAC | | |

TABLE 5A

Additional HPV Type Probes for Use With L1 Consensus Primers

| Probe | Seq. ID No. | HPV Type | Sequence |
|---|---|---|---|
| MYB186 | 29 | HPV26 | GCTGACAGGTAGTAGCAGAGTT |
| MYB187 | 30 | HPV26 | GCCATAACATCTGTTGTAAGTG |
| MYB188 | 31 | HPV26 | GAGTGGATGCAGATGCTG |
| MYB189 | 32 | HPV26 | CTAATGGTAAGGTTAGTACTGCG |
| MYB202 | 33 | HPV26 | CAGCATCTGCATCCACTC |
| MYB168 | 34 | HPV35 | ACCCAGTGCACCAAAACC |
| MYB169 | 35 | HPV35 | CCAAAACCTAAAGATGATCCAT |
| MYB174 | 36 | HPV40 | CACCAGGCCCATATAATAACAG |
| MYB175 | 37 | HPV40 | TGTCAGCGCGATGCC |
| MYB182 | 38 | HPV53 | GCAACCACACAGTCTATGTC |
| MYB159 | 39 | HPV53 | GACTCTTTCCGCAACCACAC |
| MYB160 | 40 | HPV54 | CAGCATCCACGCAGGATAG |
| MYB161 | 41 | HPV54 | GAATAATGCCCCTGCAAAG |
| MYB170 | 42 | HPV55 | CAAATACAGATATGTGCAGT |
| MYB151 | 43 | HPV55 | GTGCTGCTACAACTCAGTCT |
| MYB171 | 44 | HPV55 | CCCTGAAAAGGCAAAGCAG |
| MYB196 | 45 | HPV56 | GCTAACCTACTGGAGGACTGG |
| MYB197 | 46 | HPV56 | GCACAGCTATAACATGTCAACG |
| MYB198 | 47 | HPV56 | CCTCCACATGTCTAAGGTACTG |
| MYB199 | 48 | HPV56 | CAGTTAAGTAAATATGATGCACG |
| MYB172 | 49 | HPV59 | ACACCSCACCGCCAGTT |
| MYB173 | 50 | HPV59 | TTAAACAGGACCCTTATGACA |
| MYB162 | 51 | HPV59 | CCTAATGWATACACACCTACCAG |
| MYB176 | 52 | HPV40 | CCCAAGGTACGGAGGATCC |
| MYB191 | 66 | HPV68 | CATACCGCTATCTGCAATCAG |
| MYB192 | 53 | HPV68 | GATGGCTTAAACTTTTGGAATG |
| MYB193 | 54 | HPV68 | CAATCAGCAGCAATTACATG |
| MYB194 | 67 | HPV68 | CTACTACTGAATCAGCTGTACC |
| MYB195 | 55 | HPV68 | CATGTAATTGCTGCTGATTG |
| MYB177 | 56 | PAP88 | TCCCCACCAGTTGCAACTAG |
| MYB178 | 57 | PAP88 | CATGTCAGAGGGAACAGCC |
| MYB163 | 58 | PAP155 | GTTGTGCCCCCTCCCTCCA |
| MYB179 | 59 | PAP251 | GACATTATGCACTGAAGTAACTAAG |
| MYB166 | 60 | PAP291 | GGCTAATGAATACACAGCCTC |
| MYB167 | 61 | PAP291 | TCCTTCCACCAGCCTTGAT |
| MYB180 | 62 | PAP291 | CGCTATCTGCAGTCCCGTGC |
| MYB181 | 63 | PAP291 | CTGCAGTCCCGTGCTATTACC |
| MYB164 | 64 | W13B | CTCAATCTGTTGCACAAACA |
| MYB165 | 65 | W13B | TAACCTTGCCCCCCTCAG |

In another aspect of the invention, improved primers are provided for amplification of HPV-51. Consensus L1 primers MY09 (Seq ID No. 269) and MY11 (Seq ID No. 267) are suitable for amplifying the L1 region of any HPV type present in a sample. However, MY09 (Seq ID No. 269) preferentially binds to HPV-51 at an internal site approximately 200 base pairs upstream of the expected MY09 (Seq ID No. 269) binding site. This can cause less efficient amplification of the HPV-51 450 bp product compared to other HPVs, and thus, lead to a false negative result. To produce a full length (450 bp) PCR product for HPV-51 with efficiency comparable to other HPV targets, a primer specific for HPV-51 is desirable in combination with the consensus primers MY09 (Seq ID No. 269) and MY 11 (Seq ID No. 267). For example, CEG05 (Seq. ID No. 94), HMB01 (Seq ID No. 95), HMB02 (Seq ID No. 96), HMB03 (Seq ID No. 97), and HMB04 (Seq ID No. 98) are oligonucleotides that are analogous to MY09 (Seq ID No. 269) and promote the amplification of the HPV-51 450 bp L1 PCR product. These sequences are provided below.

| CEG05 | Seq. ID No. 94 | CGACCCAATGCAAATTGGTC |
|---|---|---|
| HMB01 | Seq. ID No. 95 | GCGACCCAATGCAAATTGGT |
| HMB02 | Seq. ID No. 96 | TGCGACCCAATGCAAATTGG |
| HMB03 | Seq. ID No. 97 | CTTGCGACCCAATGCAAATT |
| HMB04 | Seq. ID No. 98 | GACCCAATGCAAATTGGTCT |

By adding any of the above primers to MY09/MY11 (Seq ID No. 269/Seq ID No. 267) the sensitivity of the L1 PCR system is substantially increased for HPV-51, and false negatives are avoided.

Following amplification of HPV-51 DNA, the PCR product can be detected by a type-specific probe or by use of labeled primers to generate a detectable nested product. For example, primers CEG03 (Seq ID No. 99) and CEG04 (Seq ID No. 100) are internal to the L1 consensus primers HMB01/MY11 (Seq ID No. 95/Seq ID No. 267) and generate a detectable HPV-51 product 412 bp in size.

| CEG03 | Seq ID No. 99 | CATTTGCTGGAACAATCAG |
|---|---|---|
| CEG04 | Seq ID No. 100 | TAAATCTAAAGAAAATCGTTCCT |

E6 Region

The present invention also provides consensus primers and HPV typing probes specific for the E6 region of genital HPVs. These probes are particularly preferred, because in some cancers, the HPV genome is partially deleted or rearranged such that only E6- and E7-related sequences are present. The E6 consensus primer pairs of the invention comprise primer pairs in which one primer is complementary to sequences near the border of the URR and E6 regions and the other primer is complementary to sequences in either the E7 region near the E6-E7 border (the E6 and E7 open reading frames overlap) or in the E6 region. These E6 consensus primers are depicted below in Tables 6a, 6b, and 6c. The use of E6 region as a second site for detection and typing may allow detection of integrated HPVs. The smaller E6 PCR products also increase the likelihood of detecting HPV sequences in archival tissues where DNA may be too fragmented to serve as a template for long PCR products.

E6 consensus primers, consensus probes, and type-specific probes are suitable for detecting and typing HPV nucleic acids, either alone or in conjunction with L1 primers and probes. In one embodiment of the invention, the E6 gene was chosen as a site for a second consensus primer set and type specific probes. While it is not an essential aspect of the present invention, the use of two sites allows rapid confirmation of typing results, thereby increasing the confidence level of the data. The use of a second site also circumvents the prospect of false negativity as a consequence of sequence variation in one of the primer binding sites.

TABLE 6a

E6 Consensus Primers
URR/E6 Consensus Positive Strand Primers

| | | | | | | | | | | | | | | | | | | | |
|---|---|---|---|---|---|---|---|---|---|---|---|---|---|---|---|---|---|---|---|
| WD73 (Seq ID No. 123) | 5' | C | G | G | T | T | S | A | | A | C | C | G | A | A | A | A | C | G | G |
| WD72 (Seq ID No. 124) | 5' | C | G | G | T | C | G | G | G | A | C | C | G | A | A | A | A | C | G | G |
| WD76 (Seq ID No. 125) | 5' | C | G | G | T | T | S | A | | A | C | C | G | A | A | A | M | C | G | G |
| WD77 (Seq ID No. 126) | 5' | C | G | G | T | T | C | A | | A | C | C | G | A | A | A | M | C | G | G |
| HPV6 43 | 5' | C | G | G | T | T | C | A | | A | C | C | G | A | A | A | A | C | G | G |
| HPV11 43 | — | — | — | — | — | — | — | | — | — | — | — | — | — | — | — | — | — | — |
| HPV16 43 | | — | — | — | — | — | G | — | | — | — | — | — | — | — | — | C | — | — | — |
| HPV18 43 | | — | — | — | — | C | G | G | G | — | — | — | — | — | — | — | — | — | — | — |
| HPV31 45 | | G | T | — | G | — | G | — | | — | — | — | — | — | — | — | — | — | — | — |
| HPV33 65 | | — | — | — | — | — | — | — | | — | — | — | — | — | — | — | — | — | — | — |

The URR/E6 positive strand primers are used as mixtures:
WD72 (Seq ID No. 124) and WD73 (Seq ID No. 123);
WD72 (Seq ID No. 124) and WD76 (Seq ID No. 125); and
WD72 (Seq ID No. 124) and WD77 (Seq ID No. 126).

TABLE 6b

E7 Consensus Negative Strand Primer

| | | | | | | | | | | | | | | | | | | | | |
|---|---|---|---|---|---|---|---|---|---|---|---|---|---|---|---|---|---|---|---|---|
| WD70 (Seq ID No. 127) | | G | C | R | C | A | G | A | T | G | G | G | R | C | A | C | A | C | | | |
| WD71 (Seq ID No. 128) | | G | C | A | C | A | C | C | A | C | G | G | A | C | A | C | A | C | | | |
| HPV06 813 | | G | C | G | C | A | G | A | T | G | G | G | A | C | A | C | A | C | | | |
| HPV11 813 | | — | — | — | — | — | — | — | — | — | — | — | — | — | — | — | — | — | | | |
| HPV16 845 | | — | A | A | — | — | — | — | — | — | — | — | G | — | — | — | — | — | | | |
| HPV18 894 | | — | — | A | — | — | C | C | A | C | — | — | — | — | — | — | — | — | | | |
| HPV33 856 | | — | — | A | — | — | — | G | — | A | — | — | G | — | — | — | — | — | | | |
| WD68 (Seq ID No. 128) | 5' | C | A | C | A | C | A | A | T | D | Y | Y | Y | A | G | T | G | T | G | C | C | C |
| WD69 (Seq ID No. 129) | 5' | C | A | C | A | C | A | A | A | G | G | A | C | A | G | G | G | T | G | T | T | C |
| HPV06 801 | 5' | C | A | C | A | C | T | A | T | G | T | T | T | A | G | T | G | T | T | C | C | C |
| HPV11 801 | | — | — | — | — | — | A | — | — | A | — | — | — | — | — | — | — | — | G | — | — | — |
| HPV16 833 | | — | — | — | — | — | A | — | — | T | C | C | — | — | — | — | — | — | G | — | — | — |
| HPV18 882 | | — | — | — | — | — | A | — | A | — | G | A | C | — | — | G | — | — | G | T | T | — |
| HPV33 844 | | — | — | — | — | — | A | — | — | A | — | — | C | — | C | — | — | — | G | — | — | — |

The E7 negative strand primers are used as mixtures:
WD70 (Seq ID No. 127) and WD71 (Seq ID No. 128); and
WD68 (Seq ID No. 128) and WD69 (Seq ID No. 129).

TABLE 6c

E6 Consensus Negative Strand Primer

| | | | | | | | | | | | | | | | | | | |
|---|---|---|---|---|---|---|---|---|---|---|---|---|---|---|---|---|---|---|
| WD67 (Seq ID No. 130) | W | G | C | A | W | A | T | G | G | A | W | W | G | C | Y | G | T | C | T | C |
| WD66 (Seq ID No. 131) | A | G | C | A | T | G | C | G | G | T | A | T | A | C | T | G | T | C | T | C |
| WD154 (Seq ID No. 132) | T | C | C | G | T | G | G | G | T | G | T | G | T | C | G | T | C | C | C |
| WD155 (Seq ID No. 133) | W | S | C | A | W | A | T | G | G | W | W | W | G | Y | C | G | T | C | Y | C |
| WD163 (Seq ID No. 134) | W | G | C | A | W | A | T | G | G | A | W | W | G | Y | Y | G | T | C | Y | C |
| WD164 (Seq ID No. 135) | W | S | C | A | W | A | T | G | G | W | D | W | G | Y | Y | G | T | C | Y | C |
| HPV6 286 | T | G | C | A | T | A | T | G | G | A | T | A | G | C | C | G | C | C | T | C |
| HPV11 286 | — | — | — | — | A | — | G | — | — | — | A | — | — | T | T | — | T | — | — | — |
| HPV16 286 | A | — | — | — | — | — | — | — | — | — | T | T | — | — | — | A | T | — | — | — |
| HPV18 292 | A | — | — | — | — | G | C | — | — | — | T | A | T | A | — | T | — | T | — | — | — |

TABLE 6c-continued

| | E6 Consensus Negative Strand Primer |
|---|---|
| HPV31 | — C — G — G — — — T G T — T — — T — C — |
| HPV33 390 | — C — — — A — — — — — T T — — C T — — — — |
| HPV43 | A — — A A — C — — — — — T — — — — T — G — |
| HPV44 | — — — — A — T — — — — A — — T T T — — — — — |
| HPV56 | — — — — — — A — — — — A — A T — A T — C — |

The E6 negative strand primers are used as mixtures; WD66 (Seq ID No. 131), WD67 (Seq ID No. 130) and WD155 (Seq ID No. 133); or WD66 (Seq ID No. 131), WD67 (Seq ID No. 130), and WD163 (Seq ID No. 134); WD66 (Seq ID No. 131), WD67 (Seq ID No. 130), and WD164 (Seq ID No. 135), or most preferably, WD66 (Seq ID No. 131), WD67 (Seq ID No. 130), and WD154 (Seq ID No. 132). The negative strand primer WD154 (Seq ID No. 132) was designed to hybridize to HPV31 DNA. Amplification of E6 sequences from HPV31 nucleic acids is improved when WD154 (Seq ID No. 132) is included.

Additional E6 consensus negative strand primers located in a region of the gene approximately 50 bp distal from WD66 (Seq ID No. 131), WD67 (Seq ID No. 130), and WD154 (Seq ID No. 132) are provided below. The primers are used in pairs as shown below and amplify a 300 bp region. The three primer sets shown, WD157/WD160 (Seq ID No. 68/Seq ID No. 69); WD158/WD161 (Seq ID No. 70/Seq ID No. 71); and WD159/WD162 (Seq ID No. 72/Seq ID No. 73), which are HPV18 specific, each correspond to the same genomic HPV region, but they differ in length.

Those skilled in the art will recognize that the E6 consensus primers of the invention amplify a sequence that comprises a portion of E7 DNA.

| | Seq ID No. | Sequence |
|---|---|---|
| WD157 | 68 | TTCTAMTGTWGTTSCATAYACASHATA |
| WD160 | 69 | CCAATGTGTCTCCATACACAGAGTC |
| WD158 | 70 | CTAMTGTWGTTSCATAYACASHATA |
| WD161 | 71 | AATGTGTCTCCATACACAGAGTC |
| WD159 | 72 | TAMTGTWGTTSCATAYACASHATA |
| WD162 | 73 | ATGTGTCTCCATACACAGAGTC |

Predicted Sizes of Products from E6 Consensus Primers

| URR/E6 Primer | Downstream Primer | Product Size for HPV Type | | | | |
|---|---|---|---|---|---|---|
| | | HPV6 | HPV11 | HPV16 | HPV18 | HPV33 |
| WD72 and WD73 | WD70 and WD71 | 770 | 770 | 802 | 844 | 791 |
| WD72 and WD76 | WD70 and WD71 | 770 | 770 | 802 | 844 | 791 |
| WD72 and WD77 | WD70 and WD71 | 770 | 770 | 802 | 844 | 791 |
| WD72 and WD73 | WD68 and WD69 | 758 | 758 | 790 | 832 | 779 |
| WD72 and WD76 | WD68 and WD69 | 758 | 758 | 790 | 832 | 779 |
| WD72 and WD77 | WD68 and WD69 | 758 | 758 | 790 | 832 | 779 |
| WD72 and WD73 | WD66 and WD67 | 243 | 243 | 242 | 242 | 225 |
| WD72 and WD76 | WD66 and WD67 | 243 | 243 | 242 | 242 | 225 |
| WD72 and WD77 | WD66 and WD67 | 243 | 243 | 242 | 242 | 225 |
| WD72 and WD76 | WD66, WD67, and WD154 | 243 | 243 | 242 | 242 | 225 |

To determine if amplification has occurred using the E6 consensus primers, E6 consensus probes are provided. E6 consensus probes WD136 (5'-GAGGTATWTGAHTTTGC [Seq ID No. 297]) and WD135 (5'-GAGATWTATKCATATGC [Seq ID No. 105]) are positive strand oligonucleotides directed to the small E6 amplification product and are used together as a mixture. The E6 consensus probes can also be used as E6 consensus positive strand primers. WD135 (Seq ID No. 105) will hybridize to HPV6 and HPV11 DNA. WD136 (Seq ID No. 297) is complementary to HPV types 16, 18, 33, and 39. When used as E6 consensus primers, the E6 consensus probes are used in the following combinations: WD65 (Seq ID No. 136) and WD64 (Seq ID No. 139); WD83 (Seq ID No. 137) and WD64 (Seq ID No. 139); and WD84 (Seq ID No. 138) and WD64 (Seq ID No. 139). The E6 consensus probes to two regions are depicted in Table 7.

TABLE 7

| E6 Consensus Probes for E6/E7 Product |
|---|
| WD65 (Seq ID No. 136)   M G A G A C R G C W W T C C A T W T G |
| WD83 (Seq ID No. 137)   M G A G A C R G S W W T C C A T W T G |

TABLE 7-continued

| | | | | | | | | | | | | | | | | | | | |
|---|---|---|---|---|---|---|---|---|---|---|---|---|---|---|---|---|---|---|---|
| WD84 (Seq ID No. 138) | M | G | A | G | A | C | R | G | V | W | W | T | C | C | A | T | W | T | G |
| WD64 (Seq ID No. 139) | A | G | A | G | A | C | A | G | T | A | T | A | C | C | G | C | A | T | G |
| HPV6 267 | C | G | A | G | G | C | G | G | C | T | A | T | C | C | A | T | A | T | G |
| HPV11 267 | — | — | — | — | A | — | A | A | — | — | T | — | — | — | C | — | T | — | — |
| HPV16 266 | A | — | — | — | A | T | — | — | G | A | — | — | — | — | — | — | — | — | — |
| HPV18 273 | A | — | — | — | A | — | A | — | T | A | T | A | — | — | G | C | — | — | — |
| HPV33 271 | A | — | — | — | A | G | — | — | A | A | — | — | — | — | — | — | T | — | — |
| Consensus Probes for Detection of Small E6 Product | | | | | | | | | | | | | | | | | | | |
| MY135 (Seq ID No. 140) | G | A | G | A | T | W | T | A | T | K | C | A | T | A | T | G | C | | |
| HPV6 225 | G | A | G | A | T | T | T | A | T | T | C | A | T | A | T | G | C | | |
| HPV11 225 | — | — | — | — | — | A | — | — | — | G | — | — | — | — | — | — | — | | |
| MY136 (Seq ID No. 272) | G | A | G | G | T | A | T | W | T | G | A | H | T | T | T | G | C | | |
| HPV16 224 | G | A | G | G | T | A | T | A | T | G | A | C | T | T | T | G | C | | |
| HPV18 231 | — | — | — | — | — | — | — | T | — | — | — | A | — | — | — | — | — | | |
| HPV33 229 | — | — | — | — | — | — | — | — | — | — | — | T | — | — | — | — | — | | |
| HPV39 | — | — | — | — | — | — | — | — | — | — | — | A | — | — | — | — | — | | |
| HPV45 | — | — | — | — | — | — | — | — | — | — | — | A | — | — | — | — | — | | |

To determine the type of the HPV present in a sample amplified using the E6 consensus primers, E6 type-specific probes are provided. These probes are depicted in Tables 8 and 8A. Using URR/E6 consensus primers comprising positive strand primers of Table 6 with WD70 (Seq ID No. 127) and WD71 (Seq ID No. 128) or WD68 (Seq ID No. 128) and WD69 (Seq ID No. 129), any of the HPV typing probes of Table 8 or Table 8A will be effective. These typing probes are also useful when E1 negative strand primers are used for amplification with the URR/E6 positive strand consensus primers.

primers WD76 and WD72 (Seq ID No. 125 and Seq ID No. 124) with WD67 (Seq ID No. 130), WD66 (Seq ID No. 131) and WD154 (Seq D No. 132); WD157 (Seq ID No. 68) and WD160 (Seq ID No. 69); WD158 (Seq ID No. 70) and WD161 (Seq ID No. 71); WD159 (Seq ID No. 72) and WD162 (Seq ID No. 73); WD66 (Seq ID No. 131) and WD155 (Seq ID No. 133); WD66 (Seq ID No. 131) and WD163 (Seq ID No. 134); and WD66 (Seq ID No. 131) and WD164 (Seq ID No. 135). These primer pairs produce a small E6 amplification product of approximately 250 base pairs in length.

TABLE 8

HPV Typing Probes for Use with E6/E7 Amplified Sequences

| Probe | Sequence ID No. | Specificity | Sequence | Genome Position |
|---|---|---|---|---|
| WD78 | 74 | HPV6 | 5' CGAAGTGGACGGACAAGAT | 643 |
| WD79 | 75 | HPV11 | 5' CAAGGTGGACAAACAAGACG | 643 |
| WD80 | 76 | HPV16 | 5' GAACACGTAGAGAAACCCAG | 534 |
| WD81 | 77 | HPV18 | 5' CAACCGAGCACGACAGGA | 530 |
| WD82 | 78 | HPV33 | 5' GAGGTCCCGACGTAGAGAA | 534 |

TABLE 8A

HPV Typing Probes for Use with Small E6 Amplified Sequences

| Probe | Sequence ID No. | Specificity | Sequence | Genome Position |
|---|---|---|---|---|
| WD165 | 79 | HPV31 | AAATCCTGCAGAAAGACCTC | 116 |
| WD166 | 80 | HPV31 | CCTACAGACGCCATGTTCA | |
| WD167 | 81 | HPV39 | CCTTGCAGGACATTACAATAG | |
| WD168 | 82 | HPV39 | CAGACGACCACTACAGCAA | |
| WD169 | 83 | HPV42 | GGTGCAAAAAGCACTTAACAG | |
| WD102 | 84 | HPV18 | ACAGTATTGGAACTTACAG | 213 |
| WD103 | 85 | HPV16 | CAACAGTTACTGCGACG | 206 |
| WD104 | 86 | HPV33 | GCAGTAAGGTACTGCAC | 88 |
| WD132 | 87 | HPV18 | GACAGTATTGGAACTTACAG | 213 |
| WD133 | 88 | HPV6 | ACACCTAAAGGTCCTGTTTC | 248 |
| WD134 | 89 | HPV11 | ACACTCTGCAAATTCAGTGC | 175 |
| RR1 | 90 | HPV33 | GTACTGCACGACTATGT | 96 |
| WD171 | 91 | HPV45 | ACAAGACGTATCTATTG | |
| WD170 | 92 | HPV18 | GCAAGACATAGAAATAA | 178 |
| RR2 | 93 | HPV33 | ACCTTTGCAACGATCTG | 213 |

The typing probes of Table 8A are useful for typing a sample amplified using positive strand URR/E6 consensus The newly discovered nucleotide sequence of the E6, E7, and part of the E1 region of the JB8 and JB10 isolates is provided below (Seq ID No. 141). The JB8 and JB 10 isolates are from an unidentified HPV type that was found in a oral/laryngeal dysplasia. The sequence of the L1 region of the JB10 isolate is provided above.

No. 110) and TYP05 (Seq ID No. 111) and TYP06 (Seq ID No. 112) with TYN07 (Seq ID No. 119) and TYN08 (Seq ID No. 120). Note that TYP03 (Seq ID No. 109) is similar to

| JB 8 AND 10 E6, E7, and Partial E1 (Seq ID No. 141) | | | | | |
|---|---|---|---|---|---|
| 1 | GGATCCCCGG | GCGAGCTCCA | CTTCAGTATT | GCCATACCCG | CTGTCCGGAA |
| 51 | CACTGTCCAC | TGCTCTCCTT | TTAGCCTGTA | AATTGTTTAC | TTCGTCTGTG |
| 101 | CTCTGCTGAC | TGTTGCTTTG | ATTTGTTATG | TCTTGCAACG | GGCTGTTCTG |
| 151 | ACTACCTAGT | AACTTTCGTT | TTAATGCACG | CACTGCCTTC | TTATTTGCTT |
| 201 | GTGTTTCTTG | TGCCTGAAAC | AATGCCTGCG | CTACCTGTTG | CTCTGCCCCA |
| 251 | TCACTAATAT | TACTATCATC | TATAAATCCA | ATTAGGTCTG | ATCCTGTATC |
| 301 | GCTACTATAC | TCTATTTCAT | CTTCTAATAT | TGTGTCTCCT | GTATGTTTTT |
| 351 | CTACTATTGC | TTCTACTGAA | AACCACCCTG | TACACCCCAA | CCCCTCCCCA |
| 401 | TCTGTACCTT | CGCAGTCCAT | TGCAGGTTTA | GTATGTAGCA | CACTGGTGGC |
| 451 | ACACCAAACT | CACGTCGCCC | ATCAGCAGCT | GCTCCACCGC | TCGGACGTTC |
| 501 | TGTCGACTGC | TTAGTACAGC | TAGCTGCACT | ATACTATTAC | ATACACAACA |
| 551 | TTCCGCTTCT | ATTCTATAAC | ACGCTTCTTG | TTCAGCTTGT | CTGGCTTGCT |
| 601 | GGTTACGCAC | ATTATCTGTT | TCATCCTCCT | CTGAGCTGTC | AAATTGTTCA |
| 651 | TAGTCCWATT | GTTCGTAACA | CTGTAGGTCA | ATTTCGGGTT | GCGGCACCAA |
| 701 | ATCTAATATA | ACATCCTGTA | TATTAATTGT | GTCTCCATGC | ATTGTTATTT |
| 751 | ATACTTGTGT | TTCTGTTGCT | TCGCGCCTTG | GTCTCCAGCA | GTTTGTGCAC |
| 801 | AACCCTTTCC | AGTACCCTGC | TATTTCATGG | AACCGTCGCT | TTTCATCCAC |
| 851 | AATTCTCTGT | TTTTCTTCCG | GTCCCAATGG | TATTTGGCAT | CTATGACACC |
| 901 | TTATTAACAA | ATTATACAAA | CTTCGTTTAG | TACGCGCTTC | CAGTGTTGCA |
| 951 | CCATACACAG | ACGATGTGTA | GCGTCTATAT | TCTATTATTT | TTGAATAGAA |
| 1001 | TATTATACAT | TTTTTACATG | CACCATATGC | ACTATCATTT | CTATACACTA |
| 1051 | TTTTTAAATC | ACATATTGCA | AAGTTATATA | CATCTGCCCA | TTCTAATGTT |
| 1101 | TTCTTGCAAT | ATACACACTG | TACCTGCAAA | GATTGCAAAG | GTGTATTCAA |
| 1151 | AGCTTCACAT | AGTTCATGTA | TCGTTCGTGG | TCTTTCTCTG | GGATCTTGAA |
| 1201 | ACATAGCTGT | TTTTGTGTAT | GGCTGTGTCT | TTTACTTTTA | TATGCACCGT |
| 1251 | TTTCGG-TTC | AACCGGAATT | C | | |

E1 Region

The present invention also provides primers that are complementary to sequences in the HPV E1 region. The E1 negative strand primers can be used with E1 positive strand primers to amplify only E1 region sequences or can be used in conjunction with E6/E7 positive strand primers to amplify sequences from E6, E7, E1, and combinations of these three regions. These E1 primers are shown below in Table 9.

both TYP02 (Seq ID No. 108) and TYP01 (Seq ID No. 107) and can be omitted from the amplification.

The E1 region is highly conserved among HPVs, however, and although typing of the sample is possible with an E1 amplification, typing is more readily accomplished when the E1 primers are used in conjunction with E6 or E7 primers, as follows. For instance, one can amplify the E6/E7 region using the following E1 and E6/E7 primers: (1) WD72

TABLE 9

| | Seq ID No. | Sequence |
|---|---|---|
| | | E1 POSITIVE STRAND PRIMERS |
| TYP01 | 107 | A T G G C K G A Y C C T G M A G G T A C |
| TYP02 | 108 | — — — — — — — — — G A T T C — — — — — — |
| TYP03 | 109 | — — — — — — — — — C C T T C — — — — — — |
| TYP04 | 110 | T G T A M W G G M T G G T T T T A T G T |
| TYP05 | 111 | — — — — — — — — — — — — — — — G A G — — |
| TYP06 | 112 | — — — — — — — — — — — — — — — A T G — — |
| | | E1 NEGATIVE STRAND PRIMERS |
| TYN01 | 113 | G T A C C T K C A G G R T C M G C C A T |
| TYN02 | 114 | — — — — — — G A A T C — — — — — — — — — |
| TYN03 | 115 | — — — — — — G A A G G — — — — — — — — — |
| TYN04 | 116 | A C A T A A A A C C A K C C W K T A C A |
| TYN05 | 117 | — — C T C — — — — — — — — — — — — — — — |
| TYN06 | 118 | — — C A T — — — — — — — — — — — — — — — |
| TYN07 | 119 | T C C A C T T C A G W A T T G C C A T A |
| TYN08 | 120 | — — — — — — — — — — — — Y A — — — — — — |

These E1 primers can be used in a variety of embodiments of the present invention. For instance, amplifications wholly within the E1 region can be performed using the following primers: (1) TYP01 (Seq ID No. 107) and TYP02 (Seq ID No. 108) and TYP03 (Seq ID No. 109) with TYN07 (Seq ID No. 119) and TYN08 (Seq ID No. 120); (2) TYP04 (Seq ID (Seq ID No. 124) and WD76 (Seq ID No. 125) with TYN01 (Seq ID No. 113) and TYN02 (Seq ID No. 114) and TYN03 (Seq ID No. 115); (2) WD64 (Seq ID No. 139) and WD65 (Seq ID No. 136) with TYN01 (Seq ID No. 113) and TYN02 (Seq ID No. 114) and TYN03 (Seq ID No. 115); (3) WD72 (Seq ID No. 124) and WD76 (Seq ID No. 125) with TYN04

(Seq ID No. 116) TYN05 (Seq ID No. 117) and TYN06 (Seq ID No. 118); (4) WD64 (Seq ID No. 139) and WD65 (Seq ID No. 136) with TYN04 (Seq ID No. 116) and TYN05 (Seq ID No. 117) and TYN06 (Seq ID No. 118); (5) WD72 (Seq ID No. 124) and WD76 (Seq ID No. 125) with TYN07 (Seq ID No. 119) and TYN08 (Seq ID No. 120); and (6) WD64 (Seq ID No. 139) and WD65 (Seq ID No. 136) with TYN07 (Seq ID No. 119) and TYN08 (Seq ID No. 120). In these latter amplifications, the entire E7 region is amplified. Thus, these amplification products can be detected with the E7 consensus probes depicted below:

C. Cervicovaginal lavage samples were stored frozen in 0.9% saline. For PCR the samples, as 1 ml aliquots, were thawed and mixed gently. Fifty microliters of sample was removed with a disposable pipet and added to 50 µl of 2× digestion solution in a labeled tube. The digestion solution was prepared fresh (1× digestion solution comprises 200 µg/ml proteinase-K, 1% Laureth-12, 20 mM Tris-HCl pH 8.5, and 0.4 mM EDTA). The samples were incubated for one hour at 55° C., spun briefly, and placed at 95° C. for 10 minutes to heat inactivate the protease. The samples were again spun briefly and 5–10 µl of each sample was added to a PCR mix for a 1130 µl PCR reaction.

| TYP09 | Seq ID No. 121 | 5' | G | A | G | C | A | A | T | T | A | G | W | A | G | A | C |
|-------|----------------|----|---|---|---|---|---|---|---|---|---|---|---|---|---|---|---|
| TYP12 | Seq ID No. 122 |    | — | — | — | — | — | — | — | — | — | A | R | Y | — | — | — |

The examples provided below merely illustrate the invention and in no way limit the scope of the accompanying claims.

EXAMPLE 1

PCR-Based Detection and Typing of HPV

Preparation of Clinical Samples for PCR

The disclosed methods for detecting and typing HPV in a clinical sample are suitable for use with any sample that is suspected of containing HPV nucleic acids. It will be apparent to one of ordinary skill in the art that sample preparation procedures vary according to sample source. Specific examples are provided for sample preparation from a variety of sources.

A. Samples collected in ViraPap™ (Digene Diagnostics, Silver Springs, Md.) collection tubes were digested according to manufacturer's instructions. Samples were handled with extreme care to avoid cross-contamination (Kwok, 1989, Nature 339:237–238). Two hundred microliters of each sample was removed for PCR analysis with a disposable piper, precipitated at –20° C. overnight with 2M ammonium acetate and 70% ethanol, dried, and resuspended in 20 µl TE (10 mM Tris-HCl, pH 7.5, 1 mM EDTA). Two µl and 5 µl aliquots were used for each amplification reaction. ViraPap™ collection tubes containing known amounts of purified human genomic DNA from the K562 cell line (ATCC ™CCL243), which does not contain HPV DNA, were processed with each batch of 20 samples to monitor possible contamination in sample processing. The K562 cell line provided a negative control.

B. Freshly collected cells from clinical swabs were suspended in 1 ml of saline, pelleted by centrifugation, and the supernatant discarded. If cell suspensions were to be stored for a period of time before the test, antibiotics were generally added to the suspension (a commercially available antibiotic, such as Fungi Bact Solution, is suitable for this purpose). The cell number was estimated, and if blood was present in the sample, the cells were suspended in 1 ml of TE buffer to lyse the red blood cells and then repelleted. About $10^2$–$10^4$ cells were used for each PCR. The cells were first suspended in 100 µl of buffer containing 50 mM Tris, pH 8.5; 1 mM EDTA; 1% Laureth-12; and 200 µg/ml proteinase K. This mixture was incubated at 55 degrees C. for about 1 hour, and then the proteinase K was heat-inactivated by incubating the mixture at 95 degrees C. for 10 minutes. Aliquots containing $10^2$–$10^4$ cells were used per 100 µl of mixture containing proteinase K treated cells.

D. The method of the present invention will often be used to determine whether tissue sections in paraffin contain HPV. To prepare such a tissue section, typically 5–10 µM in width, for use in the present method, the following procedure was employed. The tissue section was extracted twice with 1 ml of octane to remove the paraffin. Each extraction was for about one-half hour. The tissue section was then rinsed twice with 100% ethanol to remove the extracting agent and dried. The section was then suspended in buffer with detergents and proteinase K (200 µg/ml proteinase-K, 1% Laureth-12, 50 mM Tris-HCl pH 8.5, and 1 mM EDTA) at 95° C. for 10 minutes and incubated at 55° C. for 2–4 hours. After heat inactivation of the proteinase K, the suspension was centrifuged to pellet debris, and about 1–20 µl of the supernatant were used for each PCR reaction.

Control DNAs

HPV DNAs used in control amplifications were either recombinant plasmids containing HPVs (6, 11, 16, 18, 31, 33, 39, and 45) or DNA from cell lines containing HPVs (HPV16: SiHa [ATCC No. HTB35] or Caski [ATCC No.CRL 1550]; and HPV18: HeLa [ATCC No. CCL2]). DNA from the K562 cell line (ATCC No. CCL243) served as an HPV-negative control. Cellular DNA (3 to 15 ng) or plasmid DNA (1–10 pg) was used in control amplifications. Products from these amplifications were used to assess the specificity of type-specific probes.

PCR Protocols

All PCR protocols were carried out using a Perkin-Elmer (Norwalk, Conn.) TC480 Thermal Cycler instrument. A typical reaction mixture contained 50 pmoles each L1 consensus primer MY09 (Seq ID No. 269) and MY11 (Seq ID No. 267); 2.5 units of Taq polymerase; 10 µl of 10× PCR buffer (0.5M KCl 100 mM Tris, pH 8.5; 40 mM $MgCl_2$); 0.2 mM of each dNTP; 1–20 µl of each clinical, cell, or paraffin sample; and deionized water to 100 µl. A 100 µl mineral oil overlay was added to each reaction to avoid evaporation. When an amplification control was included in the reaction, 5 picomoles of each β-globin primer (PC04 [Seq ID No. 102] and GH20 [Seq ID No. 104]) was added to the reaction mix.

Because of the extreme sensitivity of PCR, the potential exists for false positive results arising from sample cross-contamination or PCR product carry-over. Extreme care was taken to prevent contamination. Only disposable or positive displacement pipets were used in sample handling and PCR set-up. In addition, pre- and post-PCR samples and reagents were kept separated throughout all stages of the work. The extensive use of negative controls support the conclusion that contamination did not occur at any point in sample handling and all positive results represent true vital presence.

The clinical or cell sample aliquot was added immediately before temperature cycling. Tubes containing the K562 negative control DNA or no added DNA were included. PCR reaction times for use with clinical samples were as follows. The machine was heated to 85° C. before the samples were placed into the machine. The machine was then programmed to execute the following temperature changes: 35 cycles of 60 seconds at 95° C., 60 seconds at 55° C. and 60 seconds at 72° C.; 5 minutes at 72° C; and then hold at 15° C.

For paraffin sections, the machine was programmed to reach 85° C. and execute temperature changes as follows: forty cycles of 60 seconds at 95° C., 60 seconds at 55° C., and 2 minutes at 72° C.; then 5 minutes at 72° C.; and then hold at 15° C. The MY09 (Seq ID No. 269), MY11 (Seq ID No. 267) PCR product is less than 600 base pairs; however, if alternative primers were used and the PCR product was expected to be longer than 600 base pairs, the machine was programmed to execute temperature changes as follows: 1 minute at 85° C.; forty cycles of a 50 second ramp to 95° C., 50 seconds at 95° C., a 50 second ramp to 55° C., 50 seconds at 55° C., a 50 second ramp to 72° C., and 2 minutes at 72° C.; 5 minutes at 72° C.; and then hold at 15° C.

Following amplification, 5 µl of each completed reaction was electrophoresed on a 7% polyacrylamide gel, ethidium bromide stained, and photographed. Dot blots of each PCR amplification reaction were prepared.

Generic HPV Probe

A generic HPV probe was synthesized from 450 bp L1 PCR fragments of HPV16 (Caski), HPV18 (HeLa), PAP238B (a cloned clinical sample identified as HPV31) and a highly divergent, unidentified HPV sequence that was previously isolated and cloned from clinical specimens and is referred to here in as PAP88. PCR amplifications were performed separately using nested primers MY74/MY75 (Seq ID No. 6/Seq ID No. 7) for HPV16; MY76/MY77 (Seq ID No. 8/Seq ID No. 9) for HPV18; MY47/MY48 (Seq ID No. 10/Seq ID No. 11) for PAP88; and MY49/MY50 (Seq ID No. 12/Seq ID No. 13) for PAP238B. The L1 amplification products were used as the templates for preparing the generic probes. The buffer and enzyme conditions were used as described above except that the final 50 µl PCR contained 50 µM each dNTP, 62.5 pmol (50 µCi) each $\alpha$-$^{32}$P-labeled dNTP, and 20 picomoles of each primer. The mineral oil overlay was omitted and the PCR cycling program was as follows: 30 seconds at 95° C., 30 seconds at 55° C., 1 minute at 72° C. for 25 cycles with a final 5 minute extension at 72° C. The PCR products from identical unlabeled reactions were visualized using electrophoresis and ethidium bromide staining. The labeled ~400 bp fragments were purified using a G50 Sephadex column, and the cpm of the probes was determined using a scintillation counter. The four probes were denatured at 95° C. for 10 minutes in the presence of sheared salmon sperm DNA, then rapidly cooled in a dry ice/ethanol bath before addition to the hybridization solution. Membranes were hybridized with a mixture of 1.0–1.5 ×10$^5$ cpm/ml of each probe.

Hybridization Analysis of PCR Products

To determine if amplification had occurred the following protocol was used. About 2 µl of each reaction mixture were added to 100 µl of denaturing solution (0.4M NaOH and 25 mM EDTA) for each replicate dot and spotted onto replicate, positively-charged, nylon membranes (such as Genetran 45, Biodyne B Membrane [Pall], or Biotran from ICN) using a dot-blot or slot blot apparatus. The resulting dot was rinsed once with 200 µl of 20×SSC. The membrane was then removed from the blotter, air-dried, and exposed to ultra-violet light (with the DNA facing the light) to covalently attach the DNA to the membrane by using a commercial UV crosslinking apparatus (50 mjoules). Amplified L1 fragments from HPV types 6, 11, 16, 18, 31, 33, 35, 39, and 45 were spotted onto each membrane as positive controls to assess cross-hybridization and optimize exposure times.

The membrane was pre-hybridized at least 30 minutes at 65° C. in a water bath or air incubator. The pre-hybridization solution contained 6×SSC, 5× Denhardt's solution, and 0.1% SDS and 100 µl g/ml denatured salmon sperm DNA. Alternatively, the membranes can merely be rinsed with pre-hybridization solution. $^{32}$P-labeled consensus probes (1.0–1.5×10$^5$ cpm/ml of hybridization mix) were added to each filter and allowed to hybridize at 55° C. for 60–90 minutes. After the hybridization, the hybridization mix was decanted and the membrane was washed twice for 10 minutes in 2×SSC and 0.1% SDS at 56° C. for the HPV generic and β-globin probes. The membrane was then air-dried and allowed to expose X-ray film from 7 to 48 hours. Background was defined by negative controls which included amplified human genomic DNA.

To determine the HPV type of amplified DNA, PCR reaction mixtures were hybridized to type-specific probes as described above. The only significant difference in the procedure was that the final wash of the filter was done at a temperature very near the T$_m$ of the particular type-specific probe. Filters hybridized to different type-specific probes were not washed together. Specifically, membranes were hybridized individually with probes for HPV types 6/11, 16, 18, 31, 33, 39, 45, 51, 52, and 53, and PAP88, PAP 155, and PAP251 as listed below. Type-specific oligonucleotide probes were $^{32}$P-labeled using a standard kinase reaction (Maniatis et al. eds. Molecular Cloning, 1982, Cold Spring Harbor, N.Y.). Membranes were pre-hybridized hybridized and hybridized as described above, then washed as follows:

| Seq ID No. | Probe | Target | Wash Temperature |
|---|---|---|---|
| 142 | MY12 | HPV6 | 57° C. |
| 147 | MY13 | HPV11 | 57° C. |
| 152 | MY14 | HPV16 | 59° C. |
| 168 | WD74 | HPV18 | 59° C. |
| 170 | WD126 | HPV31 | 57° C. |
| 172 | WD128 | HPV31 | 57° C. |
| 178 | MY16 | HPV33 | 57° C. |
| 179 | MY59 | HPV33 | 57° C. |
| 184 | MY89 | HPV39 | 58° C. |
| 185 | MY90 | HPV39 | 58° C. |
| 196 | MY70 | HPV45 | 59° C. |
| 197 | MY98 | HPV45 | 59° C. |
| 202 | MY87 | HPV51 | 58° C. |
| 203 | MY88 | HPV51 | 58° C. |
| 205 | MY81 | HPV52 | 57° C. |
| 206 | MY82 | HPV52 | 57° C. |
| 207 | MY101 | HPV53 | 58° C. |
| 208 | MY102 | HPV53 | 58° C. |
| 209 | MY103 | HPV53 | 58° C. |
| 224 | MY83 | PAP88 | 58° C. |
| 225 | MY84 | PAP88 | 58° C. |
| 226 | MY86 | PAP155 | 58° C. |
| 220 | MY93 | PAP251 | 58° C. |
| 221 | MY94 | PAP251 | 58° C. |

Autoradiogram exposures that gave an intensity comparable to the generic probe were analyzed using the same standards described above. The sensitivity of this method was copies of cloned HPV16 DNA or 10 HeLa cells containing 100–500 copies of HPV18, per 1 ml collection tube when 2–5% was analyzed.

EXAMPLE 2

Dual Amplification Of Archival Samples

A second set of consensus primers was designed to amplify a region of the E6 gene approximately 246 bp in length. These consensus primers were used in addition to the L1 consensus primers described in Example 1. The second set provides a means to generate corroborative HPV typing data and focuses on a gene which is consistently retained and expressed in tumors (Yee et al., 1985, Am. J. Pathol. 116:361–366; Seedorf et al., 1987, EMBO 6:139–144; and Broker et al., In Cancer Cells: Molecular Diagnostics of Human Cancer, vol. 7, Cold Spring Harbor, N.Y., 1989, pp. 197–208).

Archival tissue sections, which included 33 cases of cervical carcinoma, were subjected to PCR amplification with the L1 and E6 primer sets. The resulting products were analyzed by dot blot hybridization with consensus and type-specific oligonucleotide probes to illustrate the efficacy of the two site amplification strategy in the detection and typing of genital HPVs.

Tumor Samples

Sections from 48 paraffin-embedded tissue blocks representing 33 cases of cervical carcinoma and 7 HPV-negative control tissues were acquired from the pathology archives at the University of Amsterdam, the University of California at San Francisco, and the University of California at Davis. The case dates ranged from 1979 to 1988. Five micron sections were cut from tissue blocks with a microtome and the microtome blade was thoroughly cleaned with xylene between each specimen to minimize cross-contamination of samples. Dry sections were transferred to Eppendorf tubes for PCR analysis and immediately adjacent sections were mounted and stained with hematoxylin and eosin for independent histological characterization. Preparation of DNA from tissue sections for PCR was done as described in Example 1.

HPV-negative tissues were interspersed with tumor samples during tissue preparation to detect any possible contamination during sample manipulation. The prepared samples were used immediately for PCR amplification, although storage at –20° C. for up to two weeks resulted in only a nominal loss in specific amplification product yield. Control DNAs, described in Example 1, were included as specified below in the section "Dot Blot Hybridization of PCR Products."

PCR Amplification

L1 and E6 amplification reactions were performed using 1 and 10 μl (0.5% and 5%) of each prepared sample. In addition to HPV-negative and HPV-positive control samples, "no DNA" controls were included during each amplification series to detect contamination during reaction set-up. Furthermore, only positive displacement pipets and disposable pipets were used in the assembly of amplification reactions to minimize possible contamination.

Each L1 amplification reaction contained 50 pmoles each of the L1 degenerate primers MY11 (Seq ID No. 267) and MY09 (Seq ID No. 269) as described (Example 1) and 5 pmoles each of the following β-globin primers:

| GH20 | Seq ID No. 104 | GAAGAGCCAAGGACAGGTAC and |
|------|----------------|--------------------------|
| PC04 | Seq ID No. 105 | CAACTTCATCCACGTTCACC) |

The β-globin were included for the simultaneous amplification of a human β-globin product of 260 bp which served as an internal control.

The E6 reactions included 10 pmoles WD72 (Seq ID No. 124) and 40 pmoles WD76 (Seq ID No. 125) (the positive strand primers) and 10 pmoles WD66, 40 pmoles WD67 (Seq ID No. 130), and 10 pmoles WD154 (Seq ID No. 134) (the negative strand primers) in a buffer containing 50 mM KCl, 10 mM Tris (8.3), 4 mM $MgCl_2$, 200 μM of each dNTP and 2.5 units of the recombinant AmpliTaq® polymerase (manufactured and developed by Hoffmann-La Roche and marketed by Perkin Elmer, Norwalk, Conn.).

Each reaction was subjected to forty amplification cycles in a DNA Thermal Cycler (Perkin Elmer, Norwalk, Conn.) using thermocycle step parameters of 95° C. for 1 minute, 55° C. for 1 minute and 72° C. for 2 minutes. An additional five minutes was included at the final 72° C. elongation cycle. Thirty cycles were used in the amplification of HPV positive control DNA. Amplification products (1/20 of the reaction) were separated by electrophoresis using 7% polyacrylamide gels and visualized by UV illumination following ethidium bromide staining.

Probes

Oligonucleotide probes used for the dot blot hybridizations were labeled to a specific activity of $0.3–1\times10^7$ cpm/pmole with $\alpha$-$^{32}$P ATP using T4 polynucleotide kinase (NENuclear/du Pont).

The consensus L1 probe was an equimolar mixture of the following four oligonucleotides corresponding to a conserved region located 50 base pairs (bp) from the 5' end of amplified region:

| MY18 | Seq ID No. 106 | 5'CTGTTGTTGATACTACACGCAGTAC; |
|------|----------------|------------------------------|
| MY46 | Seq ID No. 28  | 5'CTGTGGTAGATACCACWCGCAGTAC; |
| MY57 | Seq ID No. 26  | 5'CTGTGGTAGATACCACACGTAGTAC; and |
| WD147 | Seq ID No. 27 | 5'CTGTAGTGGACACTACCCGCAGTAC. |

L1 type-specific probes were MY12 (Seq ID No. 142) for HPV6, MY13 (Seq ID No. 147) for HPV11, MY14 (Seq ID No. 152) for HPV16, WD74 (Seq ID No. 168) for HPV18, WD126 (Seq ID No. 170) and WD128 (Seq ID No. 172) for HPV31, MY16 (Seq ID No. 178) and MY59 (Seq ID No. 179) for HPV33 and MY70 (Seq ID No. 196) for HPV45. MY12 (Seq ID No. 142) and MY13 (Seq ID No. 147) were used together as a mixture to detect both HPV6 and 11. In clinical practice it is not necessary to separate HPV6 and HPV11 type specific probes because these HPVs are highly related in sequence and in pathogenic potential. HPV6 and HPV11 are most often associated with benign lesions.

The use of two type specific probes for each HPV type provides additional assurance that all HPV DNAs will be typed correctly including variants, where nucleotide changes in the region of one type specific probe have occurred, will not be mistyped. Probes WD126 (Seq ID No. 170), WD128 (Seq ID No. 172), and WD170 (Seq ID No. 92) were designed using sequence information generated from amplification products of clinical isolates which were subsequently identified as HPV31 and HPV45. WD128 (Seq ID No. 172) and WD126 (Seq ID No. 170) reside in separate domains on the L1 product. WD128 (Seq ID No. 172) detects both HPV31 and a variant referred to as HPV31b. The sequence of the HPV31b L1 product contains a restriction site not present in the archetypic HPV31. PC03 (Seq ID No. 103) was used to identify the β-globin product according to Example 1.

Oligonucleotide probes designed to distinguish E6 products were: WD 133 (Seq ID No. 88) for HPV6, WD134 (Seq ID No. 89) for HPV11, WD103 (Seq ID No. 85) for HPV16, WD132 (Seq ID No. 87) and WD170 (Seq ID No. 92) for HPV18, WD165 (Seq ID No. 79) and WD166 (Seq ID No. 80) for HPV31, RR1 (Seq ID No. 90) and RR2 (Seq ID No. 93) for HPV33, and WD171 (Seq ID No. 91) for HPV45.

The sequence of the HPV45 E6/E7 region was determined from pHPV45 kindly provided by K. Shah (Johns Hopkins University).

Dot Blot Hybridization Of PCR Products

Replicate dot blots were prepared using 1/50 (2 µl) of each amplification reaction. Additionally, control reactions (HPV positive SiHa DNA, HPV negative K562, and "no DNA") from each amplification series were included. Two µl of each reaction were denatured in 100 µl of 0.4N NaOH, 25 mM EDTA for each dot, applied to a Gentran 45 membrane (Plasco, Inc), and covalently bound by UV linking using a Stratalinker (Stratagene, Inc.) at 400 (×100) µJoules. The filters were washed in 0.1×SSC, 0.5% SDS at 60° C. for 30 minutes, followed by prehybridization for 15 minutes at 55° C. with 6× SSC, 5× Denhardt's solution 0.5% SDS, 100 g/ml single-stranded sheared salmon sperm DNA.

Replicate filters were separately hybridized with $^{32}$P-labeled type-specific and generic oligonucleotide probes (1–200,000 cpm/ml) in 6× SSC, 5× Denhardt's solution 0.5% SDS, 100 µg/ml single-stranded sheared salmon sperm DNA for 1 hour at 55° C. Probes WD170 (Seq ID No. 92) and WD171 (Seq ID No. 91) required hybridization at 45° C.

Filters were rinsed briefly in 2×SSC, 0.1% SDS at room temperature and then twice for 10 minutes at 45° C. (WD170 [Seq ID No. 92] and WD171 [Seq ID No. 91]); 50°–52° C. (WD132 [Seq ID No. 87], RR1 [Seq ID No. 90] and RR2 [Seq ID No. 93]); 55°–56° C. (the consensus L1 probe mix, WD103 [Seq ID No. 85], WD132 [Seq ID No. 132], WD165 [Seq ID No. 79], and WD166 [Seq ID No. 60]); 56°–57° C. (MY12/MY13 [Seq ID No. 142/Seq ID No. 147], WD126 [Seq ID No. 170], MY16 [Seq ID No. 178], MY70 [Seq ID No. 196], and WD133/WD134 [Seq ID No. 88/Seq ID No. 89]); or 58°–59° C. (MY14 [Seq ID No. 152], WD128 [Seq ID No. 172], MY59/MY64 [Seq ID No. 179/Seq ID No. 180], MY70 [Seq ID No. 196], and WD74 [Seq ID No. 168]). The membranes were subjected to autoradiography using Kodak XAR-5 film. L1 and E6 dot blot results were scored independently. The results indicated that for HPV45, MY69 (Seq ID No. 195) may be a preferred type-specific probe, because MY70 (Seq ID No. 196) has some sequence similarity to other HPVs.

Bands of predicted size for E6 or L1 were not detected in reactions from the normal cervical tissues nor an appendix. PCR products of the expected size for an L1 product were observed in all tumor samples with the exception of one of the older samples in the collection. Typing results with the E6 and L1 products were in complete agreement in all cased examined, except for one specimens which failed to produce an L1 PCR product. The single L1-negative specimen found in this study illustrates the value of a strategy based on two site analysis.

Other modifications of the embodiments of the invention described above that are obvious to those of ordinary skill in the areas of molecular biology, medical diagnostic technology, biochemistry, virology, genetics and related disciplines are intended to be within the scope of the accompanying claims.

EXAMPLE 3

Preparation of the Biotinylated Long Probes

In a non-isotopic detection format, Bio-11 (dUTP) (Sigma #B7645) was incorporated into the long L1 probe instead of $^{32}$P dNTP. Subsequent detection of the probe utilized a SA-HRP binding step and development of signal with Amersham's Enhanced ChemiLuminescence (ECL) system.

All reactions contained 2 µl of a 1:100 or 1:1000 dilution of the appropriate MY09/MY11 (Seq ID No. 269/Seq ID No. 267) generated L1 PCR product, 50 mM KCL, 10 mM Tris, pH 8.5, 2.5 units Taq polymerase, 200 µM dATP, dCTP, dGTP, 100 µM dTTP and 100 µM Bio-11 dUTP. The primer and MgCl$_2$ concentrations varied as follows: MY47 (Seq ID No. 10) and MY48 (Seq ID No. 11), 10 picomoles per primer and 4 mM MgCl$_2$; MY49 (Seq ID No. 12) and MY50 (Seq ID No. 13), 10 picomoles each primer and 6 mM MgCl$_2$; MY74 (Seq ID No. 6) and MY75 (Seq ID No. 7), 10 picomoles each primer and 4 mM MgCl$_2$; MY76 (Seq ID No. 8) and MY77 (Seq ID No. 9), 50 picomoles each primer and 8 mM MgCl$_{12}$. Each reaction was 200 µl in volume with a 100 µl mineral oil overlay. Thermal cycling parameters were 30 seconds at 95° C., 30 seconds at 55° C. and 1 minute at 72° C. with a five minute extension at 72° C. at the end of 30 cycles. The biotinylated PCR product was purified using a G50 Sephadex column (eluted with TE and 0.2% SDS) or an isopropanol, 2M ammonium acetate precipitation. Aliquots of both biotinylated and non-biotinylated long probes were electrophoresed on 7% acrylamide gels, ethidium bromide stained, and photographed under UV light. The non-biotinylated probe migrated further than the biotinylated probe.

The hybridization protocol using biotinylated probes was as described in Example I. Amersham's ECL system was used for detection according to the manufacture's instructions; however, the amount of SA-HRP used at the binding step was titrated for each lot of reagent.

Other modifications of the embodiments of the invention described above, that are obvious to those of ordinary skill in the areas of molecular biology, medical diagnostic technology, biochemistry, virology, genetics, and related disciplines, are intended to be within the scope of the invention and the accompanying claims.

EXAMPLE 4

HPV Typing Assay

An HPV typing assay incorporating detection by probe hybridization in a dotblot format is described in the protocol below. In the dot blot format, a small portion of the amplified DNA is denatured, applied to nylon membranes, and immobilized. Each membrane is then immersed in a probe solution to allow hybridization to the labeled probe. Replicate membranes are hybridized with either probes for one HPV type or a generic HPV probe. Probes can be radioactively labeled, as described above, or covalently conjugated to horseradish peroxidase (HRP) to provide a means of nonisotopic detection in the presence of a chromogenic or chemiluminescent substrate.

Samples are collected and prepared, and the PCR amplification is carried out essentially as described in Example 1, above. The reaction mixture described in Example 1 is modified by the addition of 5 pmoles of HMB01 (Seq ID No. 95) and 2 units UNG (developed and manufactured by Hoffmann-La Roche and marketed by Perkin Elmer, Norwalk, Conn.), and 0.6 mM dUTP is added in place of 0.2 mM dTTP. No mineral overlay is used. Reactions are carded out in a TC9600 Thermal Cycler (Perkin Elmer, Norwalk, Conn.).

The reaction mixtures are incubated prior to amplification at 50° C. for 2 minutes to allow for UNG-catalyzed degradation of any contaminating oligonucleotide transcripts from previous reactions that contain dUMP. The temperature profile for the amplification reaction consists of 35 cycles of 95° C. for 20 seconds, 55° C. for 30 seconds, and 72° C. for 30 seconds. The reaction mixture is incubated at 72° C. for 5 minutes and then either held at 72° C. or the amplified DNA is denatured immediately.

Generic HPV Probe

A biotinylated generic HPV probe is synthesized as a mixture of 450 base pair PCR amplification products from the amplifications of the L1 region of HPV 16 (Caski), HPV 18 (HeLa), HPV51, and PAP88. Separate PCR amplifications are performed using biotinylated primers MY74 (Seq ID No. 6) and MY75 (Seq ID No. 7) for the amplification of HPV 16, MY76 (Seq ID No. 8) and MY77 (Seq ID No. 9) for the amplification of HPV8, MY47 (Seq ID No. 10) and MY48 (Seq ID No. 11) for the amplification of PAP88, and CEG03 (Seq ID No. 99) and CEG04 (Seq ID No. 100) for the amplification of HPV51.

DNA from each HPV listed above is amplified using the primers MY09 (Seq ID No. 269) and MY11 (Seq ID No. 267) as described above. A 1:100 to 1:1000 dilution of the amplification products is then used in the type-specific amplifications. The type-specification amplifications are carried out in 100 µl reactions essentially as described in Example 1, above. Each reaction contains the following reagents.

1–2 µl of target nucleic acid
50 mM KCL
10 mM Tris-HCl, pH 8.5
2.5 U Taq DNA polymerase
200 µM each dATP, dCTP, and dGTP
100 µM dTTP
100 µM dUTP

* Developed and manufactured by Hoffmann-La Roche and marketed by Perkin Elmer, Norwalk, CT Additionally, the individual reactions contain primers and MgCl2 at the following concentrations.

HPV16 amplification reaction
0.1 µM (10 pmol) each MY74 (Seq ID No. 6) and MY75 (Seq ID No. 7)
4 mM MgCl2

HPV18 amplification reaction
0.5 µM (50 pmol) each MY76 (Seq ID No. 8) and MY77 (Seq ID No. 9)
8 mM $MgCl_2$ PAP88 amplification reaction
0.1 µM (10 pmol) each MY47 (Seq ID No. 10) and MY48 (Seq ID No. 11)
4 mM $MgCl_2$ HPV51 amplification reaction
0.5 µM (50 pmol) each CEG03 (Seq ID No. 99) and CEG04 (Seq ID No. 100)
4 mM $MgCl_2$ The biotinylated amplification products are purified by isopropanol precipitation. To each reaction is added 0.4 volumes 5M ammonium acetate and 2 volumes isopropanol. The amplification product is resuspended in TE buffer. Before hybridization, the probe is denatured at 95° C. for 10 minutes in the presence of 2 µg/ml salmon sperm DNA. The optimal ratio and concentration of probe fragments to be used in the hybridization are determined empirically.

Dot Blot Hybridization Analysis of PCR Products

The amplification product is analyzed by hybridization to probes essentially as described in Example 1. Biodyne B nylon membranes (ICN, Irvine, Calif.) are pretreated by incubating for at least 30 minutes in 0.1× SSPE and 0.5% SDS at 65° C. About 3 µl of each amplification reaction mixture is added to 100 µl of denaturing solution (0.4N NaOH and 25 mM EDTA) and spotted onto a membrane. The resulting dot is rinsed with 400 µl of 20× SSC. Amplified L1 fragments from HPV types 6, 11, 16, 18, 26, 31, 33, 35, 39, 40, 42, 45, 51–59, 68, and clinical samples P88, P155, P238A, P291, and W13B are spotted onto each membrane as positive controls to assess cross-hybridization and optimize exposure times. Duplicate membranes are created for hybridization with probes for each of the HPV types described below and the generic HPV probe.

Membranes are "pre-hybridized" by soaking in hybridization buffer (5× SSPE and 0.1% SDS) at 65° C. for at least 30 minutes. Biotinylated consensus probes are added to each filter and allowed to hybridize at 55° C. for at least 90 minutes. The hybridization mix is decanted and the membrane is washed twice at 56° C. for 10 minutes in 2× SSPE and 0.1% SDS.

The ECL detection protocol (Amersham, Arlington Heights, Ill.) is used for visualization of the hybridized probes. Membranes hybridized to different type-specific probes are treated separately. The membranes are submerged in 250 ml of wash solution containing streptavidin-horseradish peroxidase (SA-HRP) at a concentration of 30 ng/ml for membranes hybridized with the generic probe mix and 40 ng/ml for membranes hybridized with the type-specific probes. The membranes are kept in the solution with gentle agitation at room temperature for 15 minutes to allow binding of the SA-HRP to the biotin probe label. The SA-HRP solution is drained and the membrane is washed twice in a large volume of 2×SSPE and 0.1% SDS with vigorous mixing for 10 minutes. The ECL development is carried out according to the manufacturer's instructions. The membrane is exposed to X-ray film at room temperature for 2 hours.

The HPV type is determined essentially as described in Example 1, except that the type-specific probes listed below are used. The set of type-specific probes listed below are all washed at the same temperature, 56° C.

| HPV Type | Probe | Seq ID No. |
|---|---|---|
| HPV6/11 | MYB12 | 142 |
|  | MYB13 | 147 |
|  | MYB125 | 145 |
| HPV16 | MYB95 | 156 |
|  | MYB133 | 159 |
| HPV18 | MYB130 | 165 |
|  | WDB74 | 168 |
| HPV26 | MYB186 | 29 |
|  | MYB187 | 30 |
| HPV31 | MYB92 | 175 |
|  | WD128 | 172 |
| HPV33 | MYB16 | 178 |
|  | MYB64 | 180 |
| HPV35 | MYB115 | 181 |
|  | MYB117 | 183 |
| HPV39 | MYB89 | 184 |
|  | MYB90 | 185 |
| HPV40 | MYB176 | 45 |
| HPV42 | MYB34 | 193 |
|  | MYB121 | 190 |
| HPV45 | MYB69 | 195 |
|  | MYB129 | 201 |
| HPV51 | MYB87 | 202 |
|  | MYB88 | 203 |
| HPV52 | MYB81 | 205 |
|  | MYB82 | 206 |
| HPV53 | MYB102 | 208 |
|  | MYB182 | 38 |
| HPV54 | MYB160 | 40 |

-continued

| HPV Type | Probe | Seq ID No. |
|---|---|---|
| | MYB161 | 41 |
| HPV55 | MYB151 | 43 |
| | MYB171 | 44 |
| HPV56 | MYB197 | 46 |
| | MYB199 | 48 |
| HPV57 | MYB154 | 217 |
| | MYB156 | 219 |
| HPV59 | MYB123 | 222 |
| | MYB162 | 51 |
| Isolate Pap 88 | MYB83 | 224 |
| | MYB178 | 57 |
| Isolate Pap 155 | MYB85 | 227 |
| | MYB163 | 58 |
| Isolate Pap 251 | MYB94 | 221 |
| | MYB179 | 59 |
| Isolate Pap 238A | MYB104 | 228 |
| | MYB106 | 230 |
| Isolate Pap 291 | MYB166 | 60 |
| | MBY167 | 61 |
| Isolate W13B | MYB164 | 64 |
| | MYB165 | 65 |
| HPV68 | MYB191 | 66 |
| | MYB194 | 67 |

Nonspecific hybridization to nonspecifically amplified genomic DNA can be assessed using a standard generated from the amplification of a sample consisting of 15,000 spleen cell equivalents. Any signal generated from the unknown sample which is equal to or lower than the signal generated from the spleen cell sample cannot be distinguished from background signal and should not be considered HPV positive.

EXAMPLE 5

Reverse Dot Blot Format

An alternate hybridization format is the reverse dot blot format in which the probes are fixed to discrete locations on a membrane and then the entire membrane is immersed in a solution containing the amplified target DNA to allow hybridization to the membrane-bound probes. The reverse dot blot process is described in copending application Ser. Nos. 197,000 and 347,495; in Saiki et al., 1989, Proc. Natl. Acad. Sci. USA 86:6230–6234; and in the AmpliType DQalpha DNA typing kit developed and manufactured by Hoffmann-La Roche Inc. and available through Perkin Elmer, each of which is incorporated herein by reference.

In one embodiment, the amplification primers are biotinylated, as described in Levenson and Chang, 1989, supra, so that any amplified DNA that hybridizes to the membrane bound probes can be easily detected. Detection is carried out by reacting streptavidin conjugated horseradish peroxidase (SA-HRP) with the amplified DNA hybridized to the fixed probe. The HRP thus becomes bound through the SA-biotin interaction to the amplified DNA and can be used to generate a signal by a variety of well known means, such as the generation of a colored compound, e.g., by the oxidation of tetramethylbenzidine (see U.S. Pat. No. 4,789, 630, incorporated herein by reference). Probes are immobilized on a nylon membrane as described in Saiki et al., 1989, supra.

One of skill in the art will recognize that the hybridization and wash conditions must be optimized for each set of probes and targets used. The following conditions are intended as suggested starting conditions to be then optimized.

Amplified PCR products are denatured by heating to 95° C. for 3 to 10 minutes, and 40 µl of the denatured PCR product are added to each probe panel for hybridization. Hybridization is carried out at the hybridization temperature (for example, 56° C.) for 20 minutes in a shaking water bath in a hybridization buffer composed of 0.5× SSC, 0.25% SDS, and 5× Denhardt's solution. The hybridization buffer is replaced with 3 ml of a solution consisting of 25 µl of SA-HRP, developed and manufactured by Hoffmann-La Roche Inc. and commercially available from Perkin Elmer (Norwalk, Conn.), in 3.1 ml of hybridization buffer, and incubated for 20 minutes at 57° C. in a shaking water bath.

Washing is carried out in a wash buffer of 2× SSC and 0.1% SDS. After a brief rinse of the membrane in 10 ml of wash buffer, a 12 minute stringent wash in 10 ml of buffer is done at the hybridization temperature (for example, 56° C.). Another 5 minute room temperature wash is then carded out, followed by a 5 minute wash in 10 ml of 0.1M sodium citrate, pH 5.0.

Chromogen binding is carried out in 5 ml of chromogen solution consisting of 5 ml of 0.1M sodium citrate, 5 µl of 3% hydrogen peroxide, and 0.25 ml of chromogen (TMB, developed and manufactured by Hoffmann-La Roche Inc. and commercially available from Perkin Elmer (Norwalk, Conn.) for 25–30 minutes at room temperature. Three 10 minute washes in distilled water are carded out at room temperature. A post-wash of 1× PBS at room temperature for 30 minutes can enhance signal quality. During steps in which chromogen is present, the membrane should be shielded from light by an aluminum foil covering. The developed membrane should be photographed for a permanent record.

EXAMPLE 6

Microwell Plate Assay for the Detection Of HPV

In this embodiment of the invention, the probes are fixed to a well of a microwell plate and the amplified target DNA is hybridized to the bound probes. As in the previous example, the amplification primers are biotinylated to allow detection of amplified DNA that hybridizes to the bound probes.

The probes are immobilized on the plastic surface of a microwell plate as follows. One hundred µl of a solution of 1M CH3COONH4 containing each probe at a concentration of 0.03–2 nanogram/µl are added into each well of a microwell plate (preferably Immulon II from Dynatech, Chantilly, Va). The plate is incubated at 37° C. for 10 to 20 hours (overnight) and then rinsed with PBS/EDTA (PBS is 2.68 mM KCL, 137 mM NaCl 1.47 mM KH2PO4, and 8.03 mM Na2HPO4). The wells are then blocked with protein, such as BSA. Alternatively, probes conjugated to bovine serum albumin (BSA) are allowed to adsorb to the plastic surface of the individual wells. Preferably, 96 well plates available from Corning are used for immobilizing BSA-conjugated probes. Amplification is carried out as described above. One hundred microliters of denaturation solution (0.4M NaOH; 80 mM EDTA and 0.005% Thymol blue) are added to each PCR tube. A new pipette tip is used for each tube. In one embodiment, detection may not be performed immediately, in which case the PCR tubes are stored overnight at 2° C. to 8° C. Because denatured amplification reactions become viscous upon storage at 2° C. to 8° C., tubes are briefly warmed at 25° C. to 30° C. prior to opening.

The appropriate number of eight well microwell plate strips (minimally 2 strips) are removed and set into the microwell plate frame. One hundred µl of hybridization/neutralization buffer was pipetted into each well of the microwell plate. Hybridization/neutralization buffer contains 2.5M NaSCN, 80 mM NaH2PO4, 10 mM NaH2PO4, and 0.125% Tween 20. Before use the pH is checked to be 5.0±0.2.

Using plugged tips with a multi channel pipetter, 25 μl of the denatured amplification reaction from each PCR tube in the tray is pipetted to the corresponding well position in the microwell plate. The plate is covered with the microwell plate lid and gently tapped on the side 10 to 15 times. Wells in which proper reagent pipetting has been done will turn light yellow in color. No change or only a slight change in blue color indicates that excess amplified product has been added. This will not affect the assay results, however. The addition of excess amplified product will increase positive OD values but negative OD values will not be affected. The plate is incubated for 60 minutes at 37° C. to allow hybridization.

Following incubation the plate is washed five times with a 1× PCR wash buffer. A 10× concentrate of PCR wash buffer contains 9.94 grams per liter of sodium phosphate dibasic, 4.41 grams per liter sodium phosphate (monobasic), 3.722 grams per liter EDTA, 87.66 grams per liter sodium chloride, 13.7 grams per liter of Tween 20, and 10 grams per liter of Pro Clin 300 (Rohm and Haas, Philadelphia, Pa.). The pH of the solution is adjusted with phosphoric acid (pH 6.5–7.1 is preferred). Washing of the plate may be performed manually or with an automated microwell plate washer programmed accordingly.

For manual washing the contents of the plate are emptied and tapped dry. Three hundred μl of wash solution are added to each well in the plate being tested, and the plate is allowed to soak for 15 to 30 seconds. The plate is again emptied and tapped dry. This wash process is repeated four additional times.

For an automated microplate washer, the following procedure is used. The contents of the wells are aspirated. The washer is programmed to add 350 microliters of working wash solution to each well in the plate being tested, soak for 30 seconds, and aspirate. The steps are repeated four additional times. The plate is then tapped dry.

Avidin-HRP conjugate is prepared as follows. A diluent is prepared that contains 0.1 molar; 0.25% emulsion 25 (DKS International, Inc., Tokyo, Japan); 1.0% Kathon CG (Rohm and Haas, Philadelphia, Pa.); 0.1% phenol; 1.0% bovine gamma globulin. The pH of the diluent solution is adjusted to 7.3 with concentrated HCl. To this diluent, 10 nM of conjugated avidin (Vector Labs, Burlingame, Calif.) is added. One hundred μl of avidin-HRP conjugate is added to each well in the plate being tested. The plate is then covered and incubated 15 minutes at 37° C. and again washed as described above.

A working substrate is prepared by mixing 2.0 ml of substrate A (3 mM hydrogen peroxide, 6.5 mM citrate, and 0.1% Kathon CG) and 0.5 ml of Substrate B (4.2 mM 3,3',5,5' tetramethylbenzidine and 40% dimethylformamide) for each multiple of two 8 well microwell plate strips (16 tests). The working substrate is prepared no more than three hours before use and stored away from direct sunlight. One hundred μl of working substrate (substrate A and B mixture) are added to each well of the plate being tested. The plate is then covered and incubated in the dark for 10 minutes at room temperature (20° C. to 25° C.).

One hundred μl of Stop Reagent (5% $H_2SO_4$) is added to each well being tested. The absorbance of each well of 450 nanometers is read within one hour of adding the Stop Reagent.

EXAMPLE 7

Detection of Oncogenic vs. Non-Oncogenic HPV Genotypes

An important application of HPV typing is the determination of whether an infected patient is at a low or high risk of developing cervical carcinoma. For this purpose, it is not necessary to determine the specific HPV type, only whether the HPV type is oncogenic or non-oncogenic. The assay described herein differentiates oncogenic HPV types and non-oncogenic types of HPV. The HPV types detected which are currently believed to be oncogenic are types 16, 18, 31, 33, 35, 39, 45, 51, 52, 53, 54, 55, 56, 58, 59, and 68. The HPV types detected which are currently believed to be non-oncogenic are types 6, 11, 26, 40, 42, 43, and 44. The classification of HPV into oncogenic and non-oncogenic categories is preliminary because of the scarcity of dam. As more information becomes available, the categories will likely be redefined. It will be clear to one of skill in the art that the exemplified probe panels can be reorganized to accommodate any redefinition of the HPV categories. The assay includes amplification of nucleic acid from all HPV types using consensus primers and subsequent classification of type by hybridization with pools of type-specific probes.

Sample Preparation

Samples are collected with and prepared as described in Example 1.

PCR Amplification

A segment of the L1 region of the HPV genome is amplified in a model 9600 Thermal Cycler, available commercially from Perkin Elmer, Norwalk, Conn., essentially as described in Example 1. The L1 consensus primers MYB09 (Seq ID No. 269), MYB11 (Seq ID No. 267), and HMBB01 (Seq ID No. 95) are biotinylated versions of MY09 (Seq ID No. 269), MY11 (Seq ID No. 267), and HMB01 (Seq ID No. 95). Reactions are carried out in a 100 μl total reaction volume containing the following reagents:

50 pmols each MYB09 (Seq ID No. 269) and MYB11 (Seq ID No. 267)

5 pmols of HPV type 51-specific biotinylated primer HMBB01 (Seq ID No. 95)

10 μl 10× reaction buffer (100 mM Tris-HCL, pH 8.3; and 500 mM KCl)

24 μl MgCl2

0.2 mM each dATP, dCTP, and dGTP 0.6 mM dUTP, 2.5 units Taq* DNA polymerase 2 units UNG* deionized water

* developed and manufactured by Hoffmann-La Roche and marketed by Perkin Elmer (Norwalk, CT).

The thermal cycler is preheated to 50° C. The clinical sample is added immediately before temperature cycling. The temperature profile for the amplification reaction is 50° C. for 2 minutes; 35 cycles of 95° C. for 20 seconds, 55° C. for 30 seconds, 72° C. for 30 seconds; and 72° C. for between 5 minutes and overnight. Reaction products should not be allowed to cool to 50° C., because residual UNG activity may begin to destroy the newly synthesized product. If analysis of the amplified product is to be delayed, the reactions can be stably stored by first incubating at 72° C. for at least 12 hours and then immediately freezing at −20° C.

Amplification with the biotinylated primers MYB09 (Seq ID No. 269) and MYB11 (Seq ID No. 267) generates a double stranded, 450 base pair product which contains a biotin label at the 5' termini of each strand. Following amplification, the amplified product is denatured by incubation in 100 μl of denaturation buffer (0.4% NaOH, 80 mM EDTA, and 0.005% Tymol Blue) at room temperature for at least 10 minutes.

Detection

The amplified product is detected and classified using type-specific probes. Detection is carded out using a microwell plate format as described in Example 6. Alternatively, detection can be carded out using a reverse dot blot format as described in Example 5. One set of proms is used to detect oncogenic HPV types and a second set of probes is used to detect non-oncogenic HPV types. The microwell plates are coated passively at 3–200 ng/well of each probe.

Each of the type-specific proms shown contains two hybridizing sequences specific to each of the two hypervariable regions in the L1 region. The number of probes which can be attached to a microwell plate is limited; having two hybridizing regions on each prom effectively doubles the number of probes which can be attached to the microwell plate. The two hybridizing regions of most of the proms shown are specific for the same type. However, because of possible problems with secondary structure, each of the type 53/54 probes, TYZ021 (Seq ID No. 247) and TYZ022 (Seq ID No. 248), and the type 51/54 probes, TYZ028 (Seq ID No. 249) and TYZ029 (Seq ID No. 250) contains one hybridizing region for each of the two types. The probe hybridization sequences are provided below.

Because, in this embodiment, the HPV type is only being classified as one of two groups, oncogenic and non-oncogenic, probes for multiple HPV types may pooled and bound to the same location in the microwell plate. In one embodiment, probes are bound to the microwell plate in two wells, one containing a pool of probes specific for the major oncogenic HPV types, types 16, 18, 31, 33, 35, 39, 45, 51, 52, 53, 54, 55, 56, 58, 59, and 68; and the other containing a pool of probes specific for the major non-oncogenic HPV types, types 6, 11, 26, 40, 42, 43, and 44. In other embodiments, additional wells are utilized to decrease the number of probes per well and increase the number of each probe present to insure adequate sensitivity or to provide more detailed type information. It may be desirable to use an equal amount of each probe to equalize sensitivity across types. In this case, because there are more oncogenic types than non-oncogenic types, more wells are required to detect oncogenic types. For example, if no more than 4 probes are put in each well, 4 wells are required for detection of the oncogenic types and two wells are required for the non-oncogenic types. Ideally, the one-well/pool embodiment described above is used.

In general, it may be possible to bind more probes to a membrane as described in Example 5 than to a microwell plate as described in Example 6. A larger amount of total probe also allows increasing the probe pool size while maintaining a sufficient number of each probe to insure adequate sensitivity. On the other hand, the microwell plates have advantages in lower cost and ease of handling.

Linked Oligonucleotide Probes

| Probe | HPV Type | Seq ID No. | Sequence |
|---|---|---|---|
| TYZ001 | HPV6/11 | 231 | CATCCGTAACTACATCTTCCAACAATGAATCCYTCTGTTTTGG |
| TYZ002 | HPV11/40 | 232 | TCTGTGTCTAAATCTGCTACACCCAAGGTACGGGAGGATCC |
| TYZ003 | HPV26 | 233 | GCTGACAGGTAGTAGCAGAGTTGCCATAACATCTGTTGTAAGTG |
| TYZ004 | HPV42 | 234 | GGCTAAGGTAACAACGCCCACTGCAACATCTGGTGAT |
| TYZ005 | HPV16 | 235 | GATATGGCAGCACATAATGACGTAACATCCCAGGCAATTG |
| TYZ006 | HPV18 | 236 | GGGCAATATGATGCTACCAATGGATGCTGCACCGGCTGA |
| TYZ007 | HPV31 | 237 | CCAAAAGCCYAAGGAAGATCTTGCAAACAGTGATACTACATT |
| TYZ008 | HPV33 | 238 | CACACAAGTAACTAGTGACAGTCCTTTGGAGGTACTGTTTTT |
| TYZ009 | HPV35 | 239 | CTGCTGTGTCTTCTAGTGACAGATCATCTTTAGGTTTTGGTGC |
| TYZ010 | HPV39 | 240 | TAGAGTCTTCCATACCTTCTACAGACACTTACAGATACCTACAG |
| TYZ011 | HPV45 | 241 | ATACTACACCTCCAGAAAAGCGCACAGGATTTTGTGTAGAG |
| TYZ013 | HPV52 | 242 | CACTTCTACTGCTATAACTTGTACACACCACCTAAAGGAAAGG |
| TYZ016 | HPV55 | 243 | GTGCTGCTACAACTCAGTCTCCCTGAAAAGGCAAAGCAG |
| TYZ017 | HPV56 | 244 | GCACAGCTATAACATGTCAACGCAGTTAAGTAAATATGATGCACG |
| TYZ018 | HPV58 | 245 | AGCACCCCCTAAAGAAAAGGAGACATTATGCACTGAAGTAACTAAG |
| TYZ019 | HPV59 | 246 | GCCAGTTAAACAGGACCCCCTAATGWATACACACCTACCAG |
| TYZ021 | HPV53/54 | 247 | TTCTACCTTACTGGAAGACTGGCAGCATCCACGCAGGATAG |
| TYZ022 | HPV53/54 | 248 | GCAACCACACAGTCTATGTCGAATAATGCCCCTGCAAAG |
| TYZ028 | HPV51/68 | 249 | CCCAACATTTACTCCAAGTAACCATACCGCTATCTGCAATCAG |
| TYZ029 | HPV51/68 | 250 | CTACTACTGAATCAGCTGTACCTATTAGCACTGCCACTGCTG |

EXAMPLE 8

Consensus Probes

Additional consensus probes that hybridize to the L1 region are provided below. These probes may be used to detect amplification products from the amplification of HPV nucleic acid using primers pairs MY09/MY 11 (Seq ID No. 269/Seq ID No. 267) or PEG01/PEG02.

Consensus Probes

| Probe | Seq ID No. | Sequence |
|---|---|---|
| CEG14 | 251 | TTTTGGGAKGTKRAYTTAMARGAAAAGTTTTC |
| CEG15 | 252 | TTTTGGRAKGTKRAYTTAAARGAAARRTTTTC |
| CEG16 | 253 | GAGGARTWTGATTTRCARTTTATWTTTCA |
| CEG17 | 254 | GARGARTWTGATTTRCAGTTTATWTTTCAR |
| CEG18 | 255 | ATTTGTTGGYRYAATCARYTRTTTGTTAC |
| CEG19 | 256 | ATWTGYTGGGGYAATCARTTRTTTGTTAC |
| CEG20 | 257 | TTTTGGGAKGTWAATTTAMWAGAAAARRTTTTC |
| CEG21 | 258 | TTTTGGRAKGTKRAYTTAAAGGAAARGTTTTC |
| CEG22 | 259 | GAAGARTWTGATTTRCAATTTATWTTTCARTTRTGT |
| CEG23 | 260 | GARGARTWTGATTTACARTTTATWTTTCAR |
| CEG24 | 261 | ATWTGTTKGGGMAATCAMYTRTTTGTTAC |
| CEG25 | 262 | ATTTGYTGGSRYAATCARTTRTTTGTTAC |

We claim:

1. A purified sequence-specific oligonucleotide probe, wherein said probe consists of a nucleotide sequence which hybridizes under sequence-specific hybridization condition to a human papillomavirus (HPV) nucleic acid sequence, wherein said nucleic acid sequence is selected from the group consisting of SEQ ID NO: 16 or the sequence fully complementary thereto, which is from HPV isolate 88;

SEQ ID NO: 17 or the sequence fully complementary thereto, which is from HPV isolate 238A;

SEQ ID NO: 19 or the sequence fully complementary thereto, which is from HPV isolate 55A or 55B;

SEQ ID NO: 276 or the sequence fully complementary thereto, which is from HPV isolate JB10;

SEQ ID NO: 277 or the sequence fully complementary thereto, which is from HPV isolate Lavc5;

SEQ ID NO: 278 or the sequence fully complementary thereto, which is from HPV isolate D7515;

SEQ ID NO: 280 or the sequence fully complementary thereto, which is from HPV isolate W13b;

SEQ ID NO: 282 or the sequence fully complementary thereto, which is from HPV isolate Lavb24b or PAP291;

and wherein said probe does not hybridize to a genomic sequence from HPV types 6, 11, 16, 18, and 33 under said conditions.

* * * * *